US010774046B2

(12) United States Patent
Telang et al.

(10) Patent No.: US 10,774,046 B2
(45) Date of Patent: Sep. 15, 2020

(54) INHIBITORS FOR THE TREATMENT OF CANCER AND RELATED METHODS

(71) Applicant: UNIVERSITY OF LOUISVILLE RESEARCH FOUNDATION, INC., Louisville, KY (US)

(72) Inventors: Sucheta Telang, Louisville, KY (US); Jason Chesney, Louisville, KY (US); John O. Trent, Louisville, KY (US); Joseph A. Burlison, Louisville, KY (US); Nagaraju Miriyala, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 10 days.

(21) Appl. No.: 16/170,391

(22) Filed: Oct. 25, 2018

(65) Prior Publication Data

US 2019/0127329 A1 May 2, 2019

Related U.S. Application Data

(60) Provisional application No. 62/577,659, filed on Oct. 26, 2017.

(51) Int. Cl.
| | | |
|---|---|---|
| *C07D 215/46* | (2006.01) | |
| *C07D 215/42* | (2006.01) | |
| *A61P 35/00* | (2006.01) | |
| *A61K 45/06* | (2006.01) | |
| *A61K 31/4706* | (2006.01) | |

(52) U.S. Cl.
CPC ........ *C07D 215/46* (2013.01); *A61K 31/4706* (2013.01); *A61K 45/06* (2013.01); *A61P 35/00* (2018.01); *C07D 215/42* (2013.01)

(58) Field of Classification Search
None
See application file for complete search history.

(56) References Cited

U.S. PATENT DOCUMENTS

| | | | |
|---|---|---|---|
| 4,035,367 A | 7/1977 | Simpson | |
| 7,759,392 B2 | 7/2010 | Soldato | |
| 8,088,385 B2 | 1/2012 | Chesney et al. | |
| 8,283,332 B2 | 10/2012 | Telang et al. | |
| 2010/0267815 A1 | 10/2010 | Telang et al. | |
| 2010/0273841 A1* | 10/2010 | Okuno | C07D 231/38 514/367 |
| 2013/0289083 A1 | 10/2013 | Mautino et al. | |
| 2015/0376132 A1* | 12/2015 | Lee | A61K 31/496 514/157 |

FOREIGN PATENT DOCUMENTS

| | | |
|---|---|---|
| WO | 2014/134705 A1 | 9/2014 |
| WO | 2015/040169 A1 | 3/2015 |
| WO | 2016/172499 A1 | 10/2016 |

OTHER PUBLICATIONS

Madrid et al, Bioorganic & Medicinal Chemistry Letters, 15(4), 1015-1018 (Year: 2005).*
Okuno et al, Chemical Abstracts 153:580355 (Abstract of US 20100273841) (Year: 2010).*
U.S. Appl. No. 15/568,751 Restriction Requirement dated May 22, 2018, 8 pages.
U.S. Appl. No. 15/568,751 Response to Restriction Requirement dated Sep. 22, 2018, 6 pages.
U.S. Appl. No. 15/568,751 nonfinal Office action dated Dec. 19, 2018, 23 pages.
U.S. Appl. No. 15/568,751 Response to nonfinal Office action dated Apr. 10, 2019, 16 pages.
U.S. Appl. No. 15/568,751 final Office action dated May 3, 2019, 20 pages.
U.S. Appl. No. 15/568,751 Response to final Office action dated Aug. 1, 2019, 19 pages.
CAS database RN 1329224-26-1, 1 page. (2011).
PubChem Substance record SID 4060327, 1 page. (2005).
Solomon et al. (2011) "Quinoline as a Privileged Scaffold in Cancer Drug Discovery" Current Medicinal Chemistry, vol. 18, No. 10, pp. 1488-1508.
Telang et al. (2015) "Targeting 6-Phosphofructo-2-kInase/Fructose-2,6-BIsphosphatase-4 (PFKFB4) in Cancer" FASEB abstract, vol. 29, No. 1 supplement, Abstract 725.29 (1 page).
_PCT/US2016/028868 ISR mailed Jul. 26, 2016, 3 pages.
_PCT/US2016/028868 Written Opinion dated Jul. 26, 2016, 9 pages.
Chenna et al., "Multiple sequence alignment with the Clustal series of programs" Nucleic Acids Res (2003) vol. 31, No. 13, pp. 3497-3500.
Chesney et al., "Fructose-2,6-bisphosphate synthesis by 6-phosphofructo-2-kinase/fructose-2,6-bisphosphatase 4 (PFKFB4) is required for the glycolytic response to hypoxia and tumor growth" Oncotarget (2014) vol. 5, No. 16, pp. 6670-6686.

(Continued)

*Primary Examiner* — Zinna Northington Davis
(74) *Attorney, Agent, or Firm* — ALGM LLP; Harry J. Guttman

(57) ABSTRACT

Some embodiments of the invention include inventive compounds. Other embodiments include compositions (e.g., pharmaceutical compositions) comprising the inventive compound. Still other embodiments of the invention include compositions (e.g., pharmaceutical compositions) for treating, for example, certain diseases using the compounds. Some embodiments include methods of using the inventive compound (e.g., in compositions or in pharmaceutical compositions) for administering and treating (e.g., diseases such as cancer). Further embodiments include methods for making the inventive compounds. Other embodiments include PFKFB4 inhibitors and methods of using the same that can target neoplastic cells, including, such as, mechanisms within those cells that relate to the use of the glycolytic pathway. In other embodiments, small molecule PFKFB4 inhibitors are used to disrupt the kinase domain of PFKFB4 and, in some instances, decrease the glucose metabolism and growth of human cancers. Additional embodiments of the invention are also discussed herein.

24 Claims, 39 Drawing Sheets

(56) References Cited

OTHER PUBLICATIONS

Chesney et al., "Targeting the sugar metabolism of tumors with a first-in-class 6-phosphofructo-2-kinase (PFKFB4) inhibitor" Oncotarget (2015) vol. 6, No. 20, pp. 18001-18011.

Colosia et al., "Isolation of a cDNA clone for rat liver 6-phosphofructo 2-kinase/fructose 2,6-bisphosphatase" Biochem Biophys Res Commun (1987) vol. 143, No. 3, pp. 1092-1098.

El-Maghrabi et al., "Tissue distribution, immunoreactivity, and physical properties of 6-phosphofructo-2-kinase/fructose-2,6-bisphosphatase" Proc Natl Acad Sci USA (1986) vol. 83, No. 14, pp. 5005-5009.

Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRI0-18): a randomised phase 2 study" Lancet Oncol (2015) vol. 16, No. 1, pp. 25-35.

Ghosh et al., "Discovery of 4-(4-(2-((5-Hydroxy-1,2,3,4-tetrahydronaphthalen-2-yl)(propyl)amino )ethyl)piperazin-1-yl)quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease" J. Med. Chem. (2010) vol. 53, pp. 2114-2125.

Goidts et al., "RNAi screening in glioma stem-like cells identifies PFKFB4 as a key molecule important for cancer cell survival" Oncogene (2012) vol. 31, No. 27, pp. 3235-3243.

Hasemann et al., "The crystal structure of the bifunctional enzyme 6-phosphofructo-2-kinase/fructose-2,6-bisphosphatase reveals distinct domain homologies" Structure (1996) vol. 4, No. 9, pp. 1017-1029.

Jain "Surflex: fully automatic flexible molecular docking using a molecular similarity-based search engine" J Med Chem (2003) vol. 46, No. 4, pp. 499-511.

Johnson et al., "Relationships between drug activity in NCI preclinical in vitro and in vivo models and early clinical trials" British Journal of Cancer (2001) vol. 84, No. 10, pp. 1424-1431.

Kemp et al., "Allosteric regulatory properties of muscle phosphofructokinase" Mol Cell Biochem (1983) vol. 57, No. 2, pp. 147-154.

Kemp et al., "Evolution of the allosteric ligand sites of mammalian phosphofructo-1-kinase" Biochemistry (2002), vol. 41, No. 30, pp. 9426-9430.

Minchenko et al., "Hypoxic regulation of the 6-phosphofructo-2-kinase/fructose-2,6-bisphosphatase gene family (PFKFB-1-4) expression in vivo" FEBS letters (2003) vol. 554, No. 3, pp. 264-270.

Mlakar et al., "Citrate inhibition-resistant form of 6-phosphofructo-1-kinase from Aspergillus niger" Appl Environ Microbiol (2006) vol. 72, No. 7, pp. 4515-4521.

Perez et al., "N-Cinnamoylated Chloroquine Analogues as Dual-Stage Antimalarial Leads" J. Med. Chem. (2013) vol. 56, pp. 556-567.

PubChem Substance record SID 35997106 (2007), 5 pages (last accessed Jul. 7, 2017).

PubChem Substance record SID 128585143 (2011), 7 pages (last accessed Jul. 7, 2017).

PubChem Substance record SID 236909839 (2015), 7 pages (last accessed Jul. 7, 2017).

PubChem Substance record SID 236984397 (2015), 7 pages (last accessed Jul. 7, 2017).

Ros et al., "Functional metabolic screen identifies 6-phosphofructo-2-kinase/fructose-2,6-biphosphatase 4 as an important regulator of prostate cancer cell survival" Cancer Discov (2012) vol. 2, No. 4, pp. 328-343.

Sakata et al., "Molecular cloning of the DNA and expression and characterization of rat testes fructose-6-phosphate,2-kinase: fructose-2,6-bisphosphatase" J Biol Chem (1991) vol. 266, No. 24, pp. 15764-15770.

Sali et al., "Comparative protein modeling by satisfaction of spatial restraints" J Mol Biol (1993) vol. 234, No. 3, pp. 779-815.

Sasaki et al., "The cell cycle associated change of the Ki-67 reactive nuclear antigen expression" J Cell Physiol (1987) vol. 133, No. 3, pp. 579-584.

Sausville, et al., "Contributions of Human Tumor Xenografts to Anticancer Drug Development" Cancer Res. (2006) vol. 66, No. 7, pp. 3351-3354.

Van Schaftingen et al., "A kinetic study of pyrophosphate: fructose-6-phosphate phosphotransferase from potato tubers. Application to a microassay of fructose 2,6-bisphosphate" Eur J Biochem (1982) vol. 129, No. 1, pp. 191-195.

Yalcin et al., "6-Phosphofructo-2-kinase (PFKFB3) promotes cell cycle progression and suppresses apoptosis via Cdk1-mediated phosphorylation of p27" Cell death & disease (2014) No. 5, Article e1337, 10 pages.

Ziakas et al., "Nitric oxide releasing derivatives of tolfenamic acid with anti-inflammatory activity and safe gastrointestinal profile" Bioorg. Med. Chem. (2005) vol. 13, pp. 6485-6492.

U.S. Appl. No. 15/568,751 nonfinal Office action dated Sep. 19, 2019, 18 pages.

Minchenko et al., "6-Phosphofructo-2-kinase/fructose-2,6-bisphosphatase gene family overexpression in human lung tumor" Ukr Biokhim Zh (2005) vol. 77, No. 6, pp. 46-50.

Minchenko et al., "Expression and hypoxia-responsiveness of 6-phosphofructo-2-kinase/fructose-2,6-bisphosphatase 4 in mammary gland malignant cell lines" Acta biochimica Polonica (2005) vol. 52, No. 4, pp. 881-888.

Minchenko et al., "Overexpression of 6-phosphofructo-2-kinase/fructose-2,6-bisphosphatase-4 in the human breast and colon malignant tumors" Biochimie (2005) vol. 87, No. 11, pp. 1005-1010.

Van Schaftingen et al., "Fructose 2,6-bisphosphate, the probably structure of the glucose- and glucagon-sensitive stimulator of phosphofructokinase" Biochem J (1980), vol. 192, No. 3, pp. 897-901.

Van Schaftingen et al., "Synthesis of a stimulator of phosphofructokinase, most likely fructose 2,6-bisphosphate, from phosphoric acid and fructose 6-phosphoric acid" Biochem Biophys Res Commun (1980) vol. 96, No. 4, 1524-1531.

Williams et al., Faye's Principles of Medicinal Chemistry, 5th edition, pp. 50 and 59-61, 2002.

Yalcin et al., "Nuclear targeting of 6-phosphofructo-2-kinase (PFKFB3) increases proliferation via cyclin-dependent kinases" J Biol Chem (2009) vol. 284, No. 36, 24223-24232.

Yalcin et al., "Regulation of glucose metabolism by 6-phosphofructo-2-kinase/fructose-2,6-bisphosphatases in cancer" Exp Mol Pathol (2009) vol. 86, No. 3, pp. 174-179.

* cited by examiner

A

B

C

D

A

B

E

F

C

D

F

G

H

A

B

C

D

E

A

B

C

D

A

B

A

B

A

B

A

B

A

INHIBITORS FOR THE TREATMENT OF CANCER AND RELATED METHODS

CROSS-REFERENCE TO RELATED APPLICATIONS

This application claims the benefit of U.S. Provisional Application No. 62/577,659, filed Oct. 26, 2017, entitled "Inhibitors for The Treatment of Cancer", which is herein incorporated by reference in its entirety.

U.S. Provisional Application No. 62/152,239, filed Apr. 24, 2015 entitled "Selective PFKFB4 Inhibitors for The Treatment of Cancer" is herein incorporated by reference in its entirety.

PCT Application No. PCT/US2016/028868, filed Apr. 22, 2016 entitled "Selective PFKFB4 Inhibitors for The Treatment of Cancer" is herein incorporated by reference in its entirety.

U.S. Provisional Application No. 62/552,716, filed Aug. 31, 2017, entitled "Inhibitors for The Treatment of Cancer" is herein incorporated by reference in its entirety.

U.S. application Ser. No. 15/568,751, with a 371(c) date of Oct. 23, 2017, entitled "Selective PFKFB4 Inhibitors for The Treatment of Cancer" is herein incorporated by reference in its entirety.

PCT Application No. PCT/US2018/048660, filed Aug. 30, 2018 entitled "Compounds, Compositions, Methods For Treating Diseases, And Methods For Preparing Compounds" is herein incorporated by reference in its entirety.

GOVERNMENT RIGHTS

This invention was made with government support under U01 HL127518 awarded by the National Institutes of Health. The government has certain rights in the invention.

BACKGROUND

Neoplastic cells utilize glycolysis to satisfy their increased needs for energy and biosynthetic precursors. The PFKFB enzymes (PFKFB1-4) synthesize fructose-2,6-bisphosphate (F2,6BP). F2,6BP activates 6-phosphofructo-1-kinase (PFK-1), a control point in the glycolytic pathway. Broadly, there remains a need to find better treatments for cancer, including but not limited to those that use PFKFB4 inhibitors.

Certain embodiments of the invention address one or more of the deficiencies described above. Some embodiments of the invention include inventive compounds. Other embodiments include compositions (e.g., pharmaceutical compositions) comprising the inventive compound. Still other embodiments of the invention include compositions (e.g., pharmaceutical compositions) for treating, for example, certain diseases using the compounds. Some embodiments include methods of using the inventive compound (e.g., in compositions or in pharmaceutical compositions) for administering and treating (e.g., diseases such as cancer). Further embodiments include methods for making the inventive compounds. Other embodiments include PFKFB4 inhibitors and methods of using the same that can target neoplastic cells, including, such as, mechanisms within those cells that relate to the use of the glycolytic pathway. In other embodiments, small molecule PFKFB4 inhibitors are used to disrupt the kinase domain of PFKFB4 and, in some instances, decrease the glucose metabolism and growth of human cancers. In other embodiments, the PFKFB4 inhibitors are selective for PFKFB4, and should not directly inhibit PFKFB1, PFKFB2, and PFKFB3. In yet other embodiments, the PFKFB4 inhibitor can have good oral bioavailability while sometimes reducing or avoiding toxicity. Additional embodiments of the invention are also discussed herein.

SUMMARY

Some embodiments of the presently disclosed subject matter relate to a compound selected from a compound of Formula (IX),

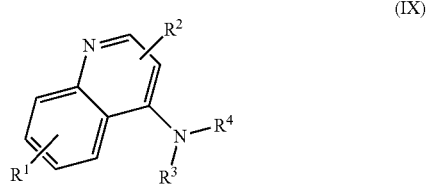

(IX)

and
salts, optical isomers, geometric isomers, salts of isomers, and derivatives thereof, where $R^1$ is a monovalent H, carboxy (—$CO_2H$), nitro (—$NO_2$), nitrate (—$ONO_2$), sulfo (—$SO_3H$), halogen, $C_1$-$C_8$ alkyl, $C_2$-$C_8$ alkenyl, $C_2$-$C_8$ alkynyl, or $C_1$-$C_7$ alkoxy, which $C_1$-$C_8$ alkyl, $C_2$-$C_8$ alkenyl, $C_2$-$C_8$ alkynyl, or $C_1$-$C_7$ alkoxy can optionally be substituted with one or more of halogen, hydroxy (—OH), $C_1$-$C_3$ alkyl, $C_1$-$C_2$ alkoxy, methanoly (—COH), carboxy (—$CO_2H$), nitro (—$NO_2$), nitrate (—$ONO_2$), cyano (—CN), amino (—$NH_2$), carbamoyl (—$CONH_2$), ethynyl (—CCH), or sulfo (—$SO_3H$); $R^2$ is a monovalent H, carboxy (—$CO_2H$), nitro (—$NO_2$), nitrate (—$ONO_2$), sulfo (—$SO_3H$), halogen, $C_1$-$C_8$ alkyl, $C_2$-$C_8$ alkenyl, $C_2$-$C_8$ alkynyl, or $C_1$-$C_7$ alkoxy, which $C_1$-$C_8$ alkyl, $C_2$-$C_8$ alkenyl, $C_2$-$C_8$ alkynyl, or $C_1$-$C_7$ alkoxy can optionally be substituted with one or more of halogen, hydroxy (—OH), $C_1$-$C_3$ alkyl, $C_1$-$C_2$ alkoxy, methanoly (—COH), carboxy (—$CO_2H$), nitro (—$NO_2$), nitrate (—$ONO_2$), cyano (—CN), amino (—$NH_2$), carbamoyl (—$CONH_2$), ethynyl (—CCH), or sulfo (—$SO_3H$); $R^3$ is a monovalent $C_1$-$C_{10}$ alkyl, $C_2$-$C_{10}$ alkenyl, $C_2$-$C_{10}$ alkynyl, or $C_1$-$C_9$ alkoxy, which $C_1$-$C_{10}$ alkyl, $C_2$-$C_{10}$ alkenyl, $C_2$-$C_{10}$ alkynyl, or $C_1$-$C_9$ alkoxy can optionally be substituted with one or more of halogen, hydroxy (—OH), $C_1$-$C_3$ alkyl, $C_1$-$C_2$ alkoxy, methanoly (—COH), —CO($C_1$-$C_3$ alkyl), carboxy (—$CO_2H$), —$CO_2$($C_1$-$C_6$ alkyl), nitro (—$NO_2$), nitrate (—$ONO_2$), cyano (—CN), amino (—$NH_2$), —N($C_1$-$C_6$ alkyl)H, —N($C_1$-$C_6$ alkyl)($C_1$-$C_6$ alkyl), carbamoyl (—$CONH_2$), ethynyl (—CCH), sulfo (—$SO_3H$), —$SO_3$($C_1$-$C_6$ alkyl) (e.g., —$SO_3$—$CH_3$),

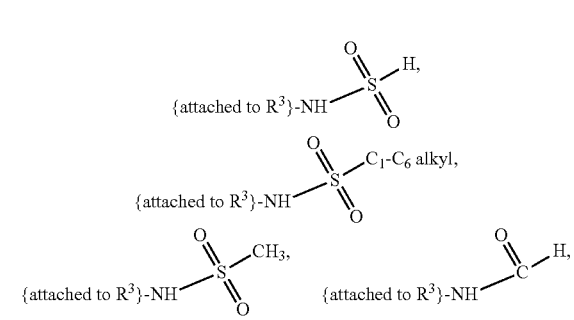

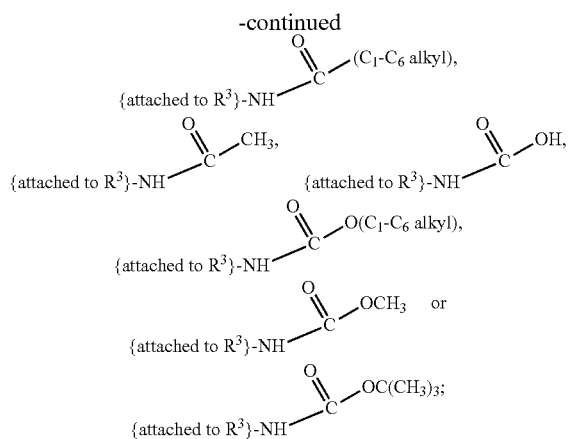

$R^4$ is a monovalent H, carboxy (—$CO_2H$), nitro (—$NO_2$), sulfo (—$SO_3H$), halogen, $C_1$-$C_8$ alkyl, $C_2$-$C_8$ alkenyl, $C_2$-$C_8$ alkynyl, or $C_1$-$C_7$ alkoxy, which $C_1$-$C_8$ alkyl, $C_2$-$C_8$ alkenyl, $C_2$-$C_8$ alkynyl, or $C_1$-$C_7$ alkoxy can optionally be substituted with one or more of halogen, hydroxy (—OH), $C_1$-$C_3$ alkyl, $C_1$-$C_2$ alkoxy, methanoly (—COH), carboxy (—$CO_2H$), nitro (—$NO_2$), nitrate (—$NO_3$), cyano (—CN), amino (—$NH_2$), carbamoyl (—$CONH_2$), ethynyl (—CCH), or sulfo (—$SO_3H$); $R^1$ can be attached to any position on the quinoline ring but is not attached to the nitrogen; $R^2$ can be attached to any position on the quinoline ring including being attached to the nitrogen; and if $R^3$ comprises a substitution with one or more of methanoly (—COH), —CO($C_1$-$C_3$ alkyl), carboxy (—$CO_2H$), —$CO_2$($C_1$-$C_6$ alkyl) (e.g., —$CO_2(CH_3)$), amino (—$NH_2$), —N($C_1$-$C_6$ alkyl)H, —N($C_1$-$C_6$ alkyl)($C_1$-$C_6$ alkyl), carbamoyl (—$CONH_2$), ethynyl (—CCH), sulfo (—$SO_3H$), —$SO_3$($C_1$-$C_6$ alkyl), —$SO_3$—$CH_3$,

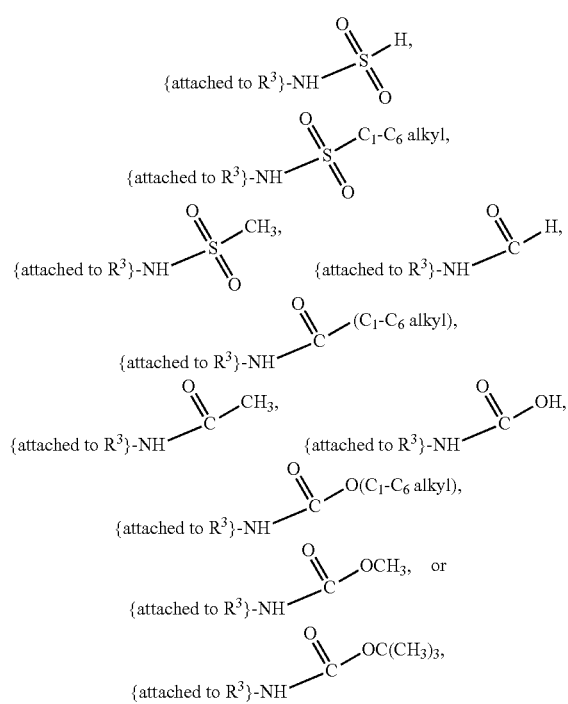

then each of methanoly (—COH), —CO($C_1$-$C_3$ alkyl), carboxy (—$CO_2H$), —$CO_2$($C_1$-$C_6$ alkyl) (e.g., —$CO_2(CH_3)$), amino (—$NH_2$), —N($C_1$-$C_6$ alkyl)H, —N($C_1$-$C_6$ alkyl)($C_1$-$C_6$ alkyl), carbamoyl (—$CONH_2$), ethynyl (—CCH), sulfo (—$SO_3H$), —$SO_3$($C_1$-$C_6$ alkyl), —$SO_3$—$CH_3$,

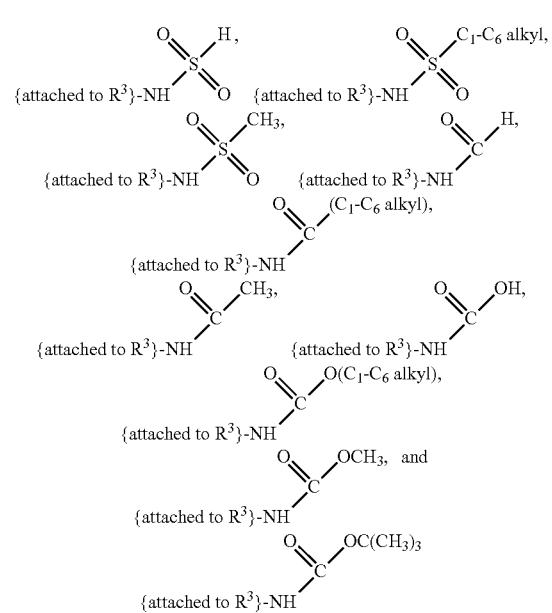

can be independently and optionally substituted with one or more of halogen, hydroxy (—OH), $C_1$-$C_4$ alkyl, $C_2$-$C_4$ alkenyl, $C_2$-$C_4$ alkynyl, $C_1$-$C_4$ alkoxy, methanoly (—COH), carboxy (—$CO_2H$), nitro (—$NO_2$), nitrate (—$ONO_2$), cyano (—CN), amino (—$NH_2$), —NH($C_1$-$C_4$ alkyl), —N($C_1$-$C_4$ alkyl)($C_1$-$C_4$ alkyl), carbamoyl (—$CONH_2$), ethynyl (—CCH), or sulfo (—$SO_3H$).

In other embodiments, the compound of Formula (IX) has $R^1$ is H, $C_1$-$C_5$ alkoxy or halogen; $R^2$ is H or $C_1$-$C_5$ alkyl; $R^2$ is attached to the nitrogen of the quinoline ring; or $R^3$ is $C_1$-$C_6$ alkyl substituted with one or more of hydroxyl, nitro, nitrate, carboxy (—$CO_2H$), —$CO_2$($C_1$-$C_6$ alkyl), —$CO_2(CH_3)$,

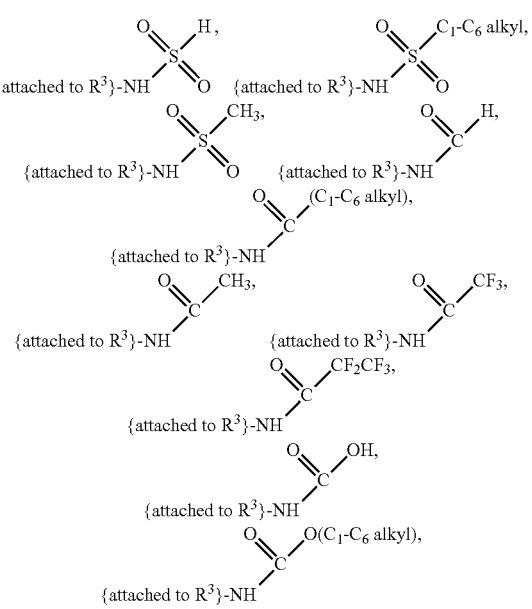

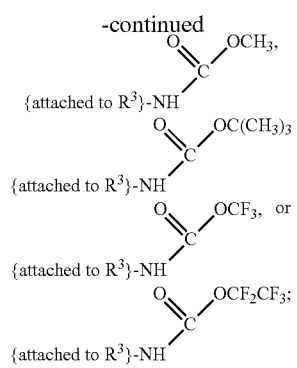
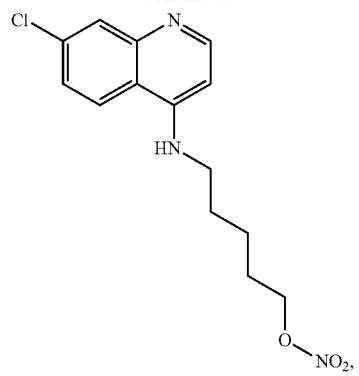
or $R^4$ is H; or a combination thereof.
In yet other embodiments, the compound of Formula (IX) is selected from
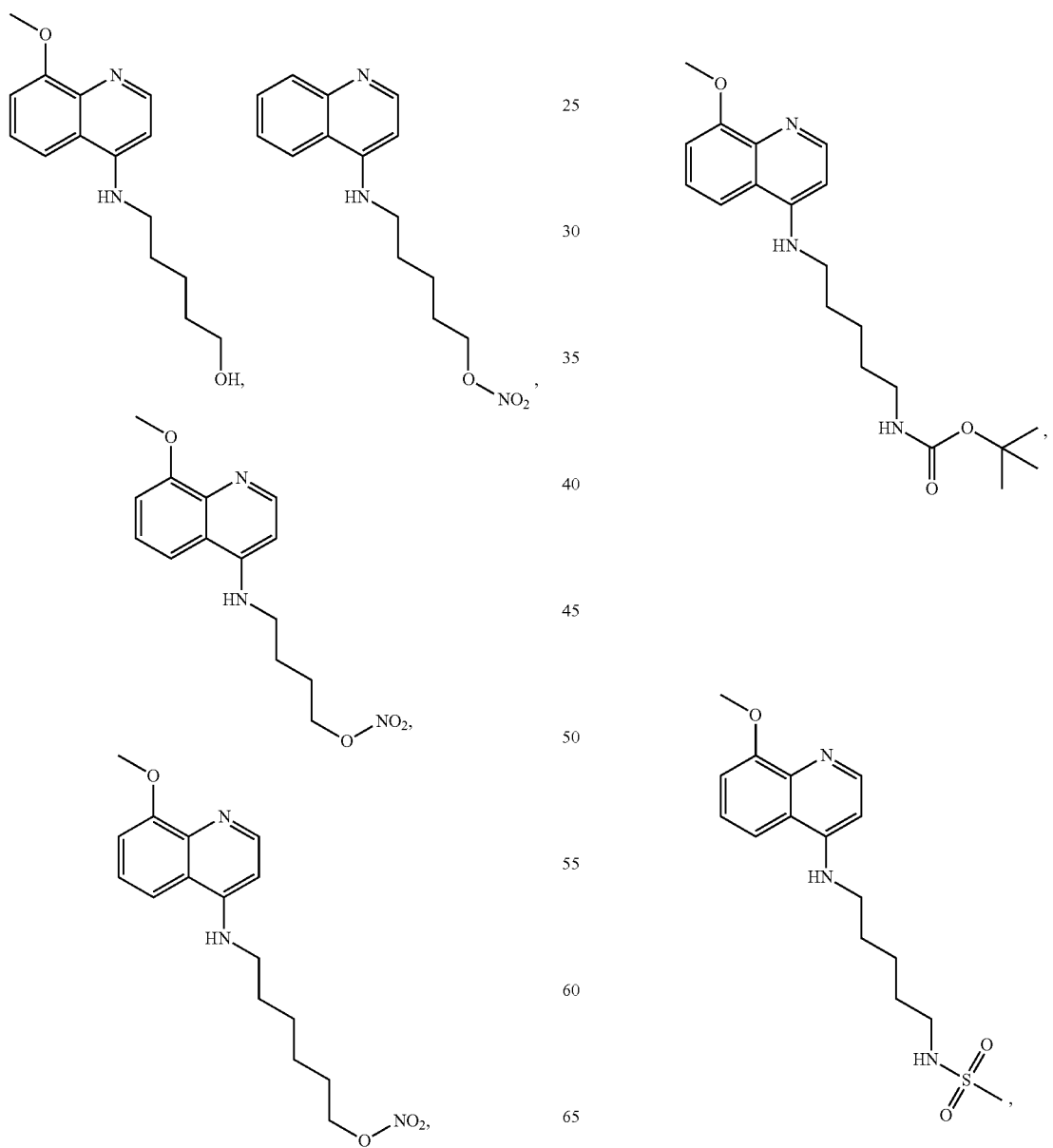

-continued

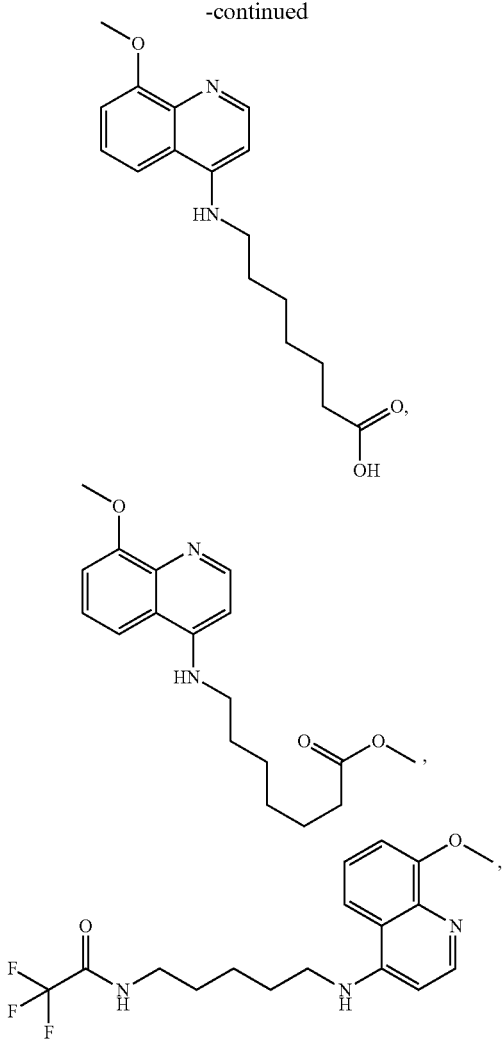

5MPN, and MPN-2.

Some embodiments of the invention include a compound of Formula (X)

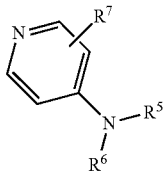

(X)

and salts, optical isomers, geometric isomers, salts of isomers, and derivatives thereof, where $R^5$ is a monovalent H, carboxy (—CO$_2$H), nitro (—NO$_2$), sulfo (—SO$_3$H), halogen, $C_1$-$C_8$ alkyl, $C_2$-$C_8$ alkenyl, $C_2$-$C_8$ alkynyl, or $C_1$-$C_7$ alkoxy, which $C_1$-$C_8$ alkyl, $C_2$-$C_8$ alkenyl, $C_2$-$C_8$ alkynyl, or $C_1$-$C_7$ alkoxy can optionally be substituted with one or more of halogen, hydroxy (—OH), $C_1$-$C_3$ alkyl, $C_1$-$C_2$ alkoxy, methanoly (—COH), carboxy (—CO$_2$H), nitro (—NO$_2$), nitrate (—ONO$_2$), cyano (—CN), amino (—NH$_2$), carbamoyl (—CONH$_2$), ethynyl (—CCH), or sulfo (—SO$_3$H); $R^6$ is a monovalent $C_1$-$C_8$ alkyl, $C_2$-$C_8$ alkenyl, $C_2$-$C_8$ alkynyl, or $C_1$-$C_7$ alkoxy, which $C_1$-$C_8$ alkyl, $C_2$-$C_8$ alkenyl, $C_2$-$C_8$ alkynyl, or $C_1$-$C_7$ alkynyl, or $C_1$-$C_7$ alkoxy can optionally be substituted with one or more of halogen, hydroxy (—OH), $C_1$-$C_3$ alkyl, $C_1$-$C_2$ alkoxy, methanoly (—COH), carboxy (—CO$_2$H), nitro (—NO$_2$), nitrate (—ONO$_2$), cyano (—CN), amino (—NH$_2$), carbamoyl (—CONH$_2$), ethynyl (—CCH), or sulfo (—SO$_3$H); $R^7$ is a monovalent H, carboxy (—CO$_2$H), nitro (—NO$_2$), nitrate (—ONO$_2$), sulfo (—SO$_3$H), halogen, $C_1$-$C_8$ alkyl, $C_2$-$C_8$ alkenyl, $C_2$-$C_8$ alkynyl, or $C_1$-$C_7$ alkoxy, which $C_1$-$C_8$ alkyl, $C_2$-$C_8$ alkenyl, $C_2$-$C_8$ alkynyl, or $C_1$-$C_7$ alkoxy can optionally be substituted with one or more of halogen, hydroxy (—OH), $C_1$-$C_3$ alkyl, $C_1$-$C_2$ alkoxy, methanoly (—COH), carboxy (—CO$_2$H), nitro (—NO$_2$), nitrate (—ONO$_2$), cyano (—CN), amino (—NH$_2$), carbamoyl (—CONH$_2$), ethynyl (—CCH), or sulfo (—SO$_3$H); and $R^7$ can be attached to any position on the ring including being attached to the nitrogen. In other embodiments, of the compound of Formula (X) $R^5$ is H or nitro; $R^6$ is $C_1$-$C_6$ alkyl, $C_1$-$C_6$ alkyl substituted with a nitro, $C_1$-$C_6$ alkyl substituted with nitro at a terminal methyl group, $C_1$-$C_6$ alkyl substituted with a nitrate, or $C_1$-$C_6$ alkyl substituted with nitrate at a terminal methyl group; $R^7$ is H, halogen, hydroxy (—OH), $C_1$-$C_3$ alkyl, or $C_1$-$C_2$ alkoxy; or $R^7$ is not attached to the nitrogen; or a combination thereof.

Other embodiments of the invention include a composition comprising a compound of Formula (IX), salts, optical isomers, geometric isomers, salts of isomers, or derivatives thereof, or a compound of Formula (X), salts, optical isomers, geometric isomers, salts of isomers, or derivatives thereof. In some embodiments, the composition comprises an amount of the compound from about 0.0001% (by weight total composition) to about 99%. In additional embodiments, the composition further comprises a formulary ingredient, an adjuvant, or a carrier.

Other embodiments of the invention include a pharmaceutical composition comprising a compound of Formula (IX), salts, optical isomers, geometric isomers, salts of isomers, or derivatives thereof, or a compound of Formula (X), salts, optical isomers, geometric isomers, salts of isomers, or derivatives thereof. In some embodiments, the pharmaceutical composition comprises an amount of the compound from about 0.0001% (by weight total composition) to about 50%. In other embodiments, pharmaceutical composition further comprised a formulary ingredient, an adjuvant, or a carrier.

Some embodiments of the invention include a method of treating cancer in a subject in need of treatment thereof, the method comprising administering to the subject an effective amount of (a) any compound disclosed herein, (b) any composition disclosed herein, or (c) any pharmaceutical composition disclosed herein. In other embodiments, the administration is at a dosage effective for specifically inhibiting 6-phosphofructo-2-kinase/fructose-2,6-bisphophatase 4 (PFKFB4). In yet other embodiments, the administration is administered orally or the administration is administered intravenously. In some embodiments, the subject is substantially free of signs of toxicity. In yet other embodiments, the subject is a mammal. In still other embodiments, the cancer is selected from breast cancer, lung cancer, colon cancer, and prostate cancer. In some embodiments, the method further comprises administering to the subject one or more additional therapeutic compounds. In other embodiments, the one or more additional therapeutic compounds comprises one or more of a PFKFB3 inhibitor, a PFKFB2 inhibitor, and a PFKFB1 inhibitor.

Some embodiments of the invention include a method of inhibiting PFKFB4 in a cell, the method comprising contacting the cell with an effective amount of (a) any compound disclosed herein, (b) any composition disclosed herein, or (c) any pharmaceutical composition disclosed herein. In other embodiments of the method, PFKFB4 is specifically inhibited. In still other embodiments, the cell is a mammalian cell. In yet other embodiments, the cell is a cancer cell. In some embodiments, the cell is or is derived from a cell line comprising H460, H1299, H441, H522, DAOY, D283, SKBR3, JURKAT, B16F10, A549, MDA-MB-231, LNCaP, HCT116, or LLC cell lines.

Some embodiments of the invention include a method of inhibiting PFKFB4 in a subject, the method comprising administering to the subject (a) any compound disclosed herein, (b) any composition disclosed herein, or (c) any pharmaceutical composition disclosed herein. In some embodiments, the administering is at a dosage effective for specifically inhibiting PFKFB4. In other embodiments, the administering is orally or is intravenously. In yet other embodiments, the subject remains substantially free of signs of toxicity.

Some embodiments of the invention include a method of reducing glycolytic flux in a cell, the method comprising contacting the cell with an effective amount of (a) any compound disclosed herein, (b) any composition disclosed herein, or (c) any pharmaceutical composition disclosed herein. In other embodiments, the cell is a mammalian cell. In yet other embodiments, the cell is a cancer cell. In still other embodiments, the cell is or is derived from a cell line comprising H460, H1299, H441, H522, DAOY, D283, SKBR3, JURKAT, B16F10, A549, MDA-MB-231, LNCaP, HCT116, or LLC cell lines.

Some embodiments of the invention include a method of reducing proliferative capacity of a cell, the method comprising contacting the cell with an effective amount of (a) any compound disclosed herein, (b) any composition disclosed herein, or (c) any pharmaceutical composition disclosed herein. In some embodiments, the cell is contacted with (a) any compound disclosed herein, (b) any composition disclosed herein, or (c) any pharmaceutical composition disclosed herein, at a dosage effective for specifically inhibiting PFKFB4. In other embodiments, the cell is a mammalian cell. In yet other embodiments, the cell is a cancer cell. In still other embodiments, the cell is or is derived from a cell line comprising H460, H1299, H441, H522, DAOY, D283, SKBR3, JURKAT, B16F10, A549, MDA-MB-231, LNCaP, HCT116, or LLC cell lines.

Some embodiments of the invention include a method of reducing fructose-2,6-bisphosphate (F2,6BP) in a cell, the method comprising contacting the cell with an effective amount of (a) any compound disclosed herein, (b) any composition disclosed herein, or (c) any pharmaceutical composition disclosed herein. In other embodiments, the cell is a mammalian cell. In yet other embodiments, the cell is a cancer cell.

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 7 shows the results of H460 NSCLC cells treated with DMSO±the indicated concentrations of two compounds of Formula IV at the indicated doses. Specifically, FBR1-02 corresponds to

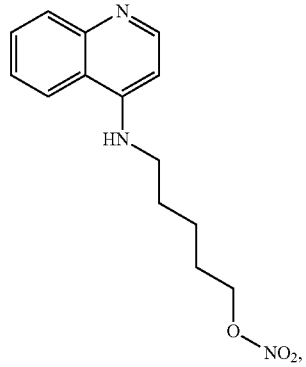

while FBR1-12 corresponds to

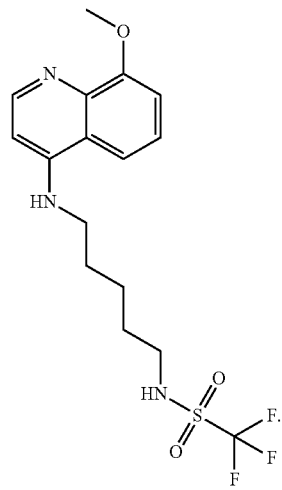

Figure 8:
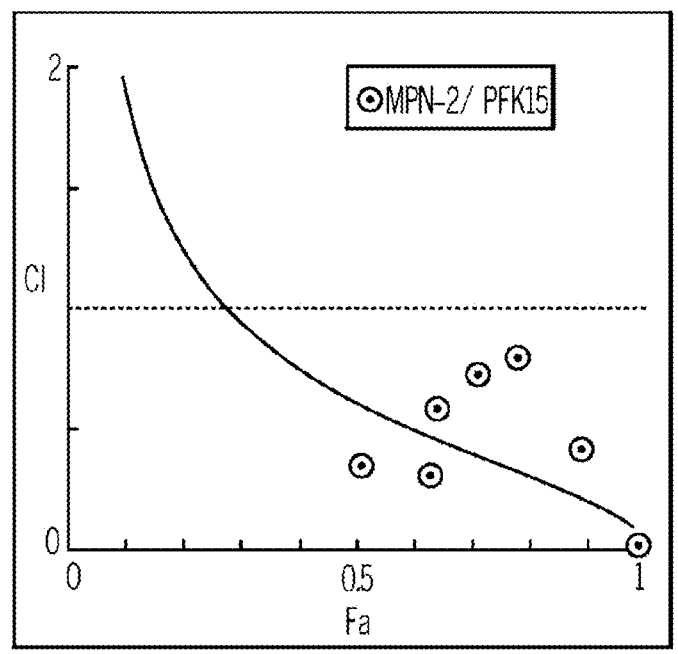
Figure 8:
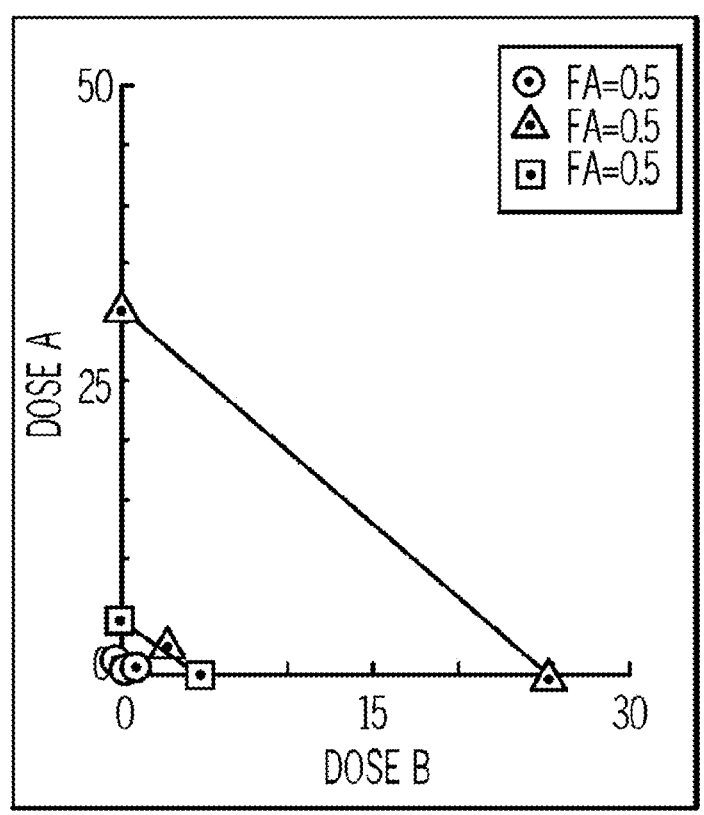

FIG. 8. Dual PFKFB4 and PFKFB3 inhibition with MPN-2 and PFK15, respectively, causes a synergistic increase in cell death. Panel (A) shows the Fa-CI combination index plot, while Panel (B) shows the isobologram.

Figure 9:
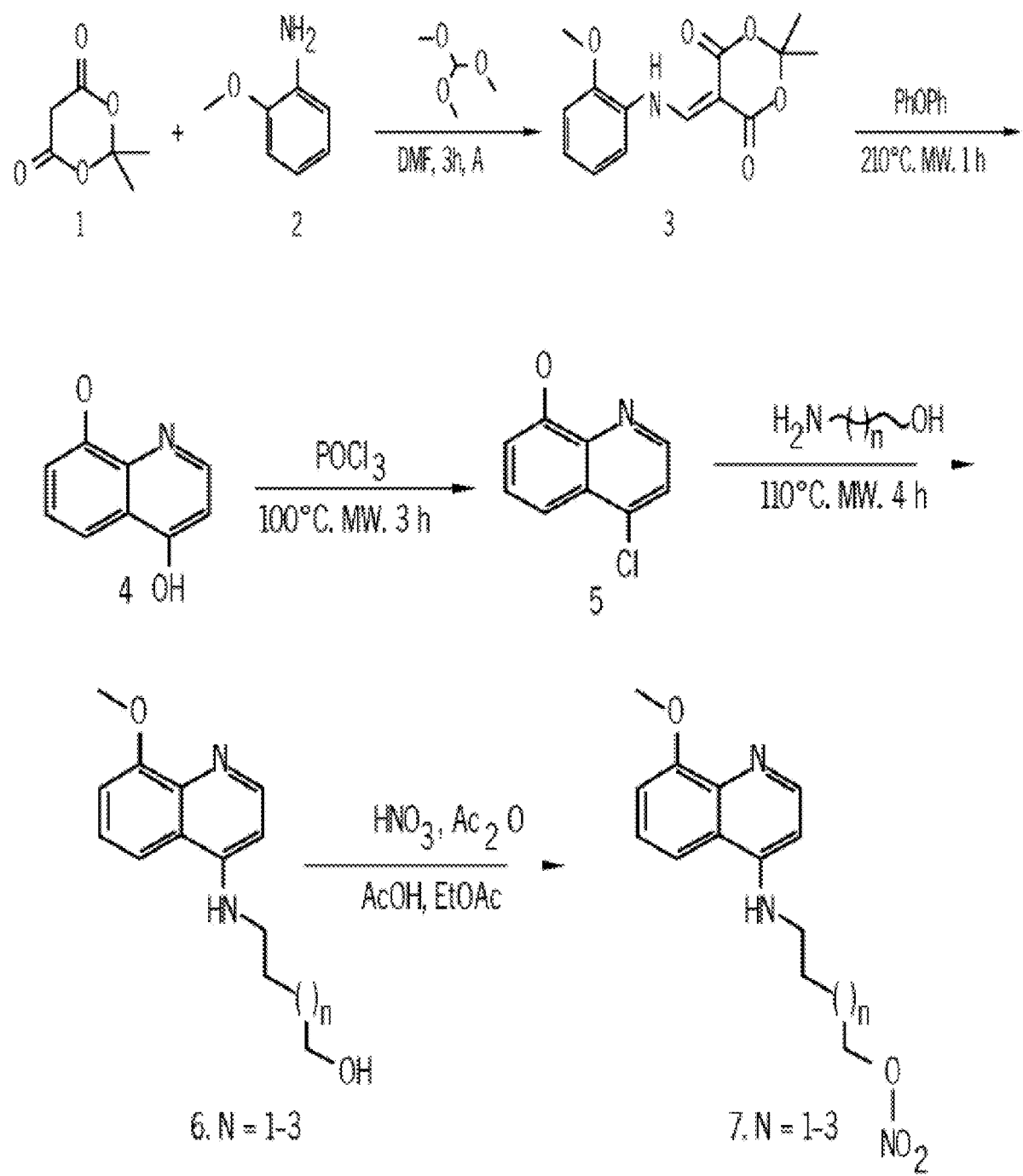

FIG. 9. Synthesis pathway of the small molecule antagonists of the kinase domain of PFKFB4. FIG. 9 shows a synthesis pathway used to create various compounds of Formulae (I), (II), and (III), (IV), (V), (VI), and (VII)).

Figure 10:
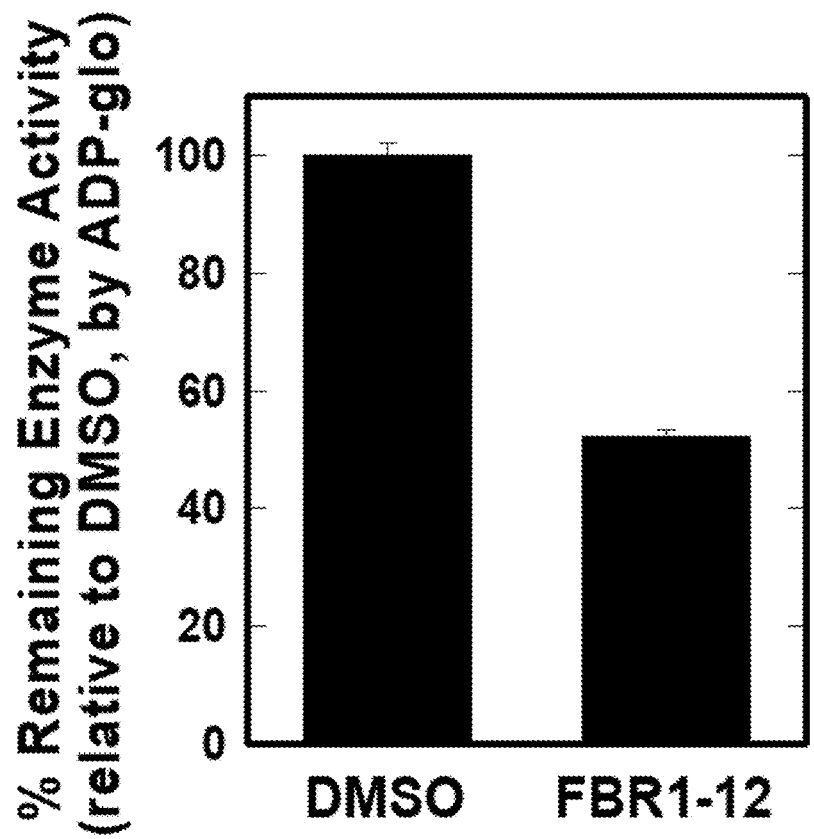

FIG. 10. Inhibiting 6-phosphofructo-2-kinase/fructose-2,6,biphosphate 4 (PFKFB4) activity by Formula (VIII) (also referred to as FBR1-12).

Figure 11:
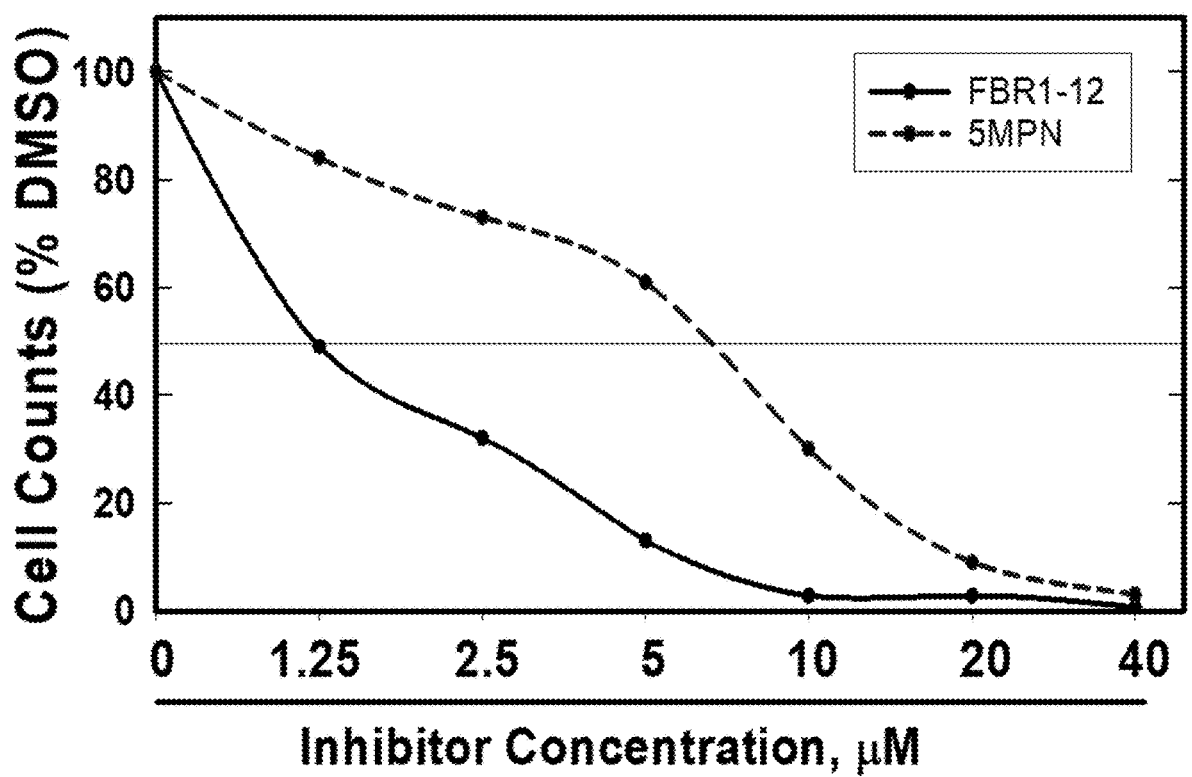

FIG. 11. Decrease in cell proliferation by Formula (VIII).

Figure 12:
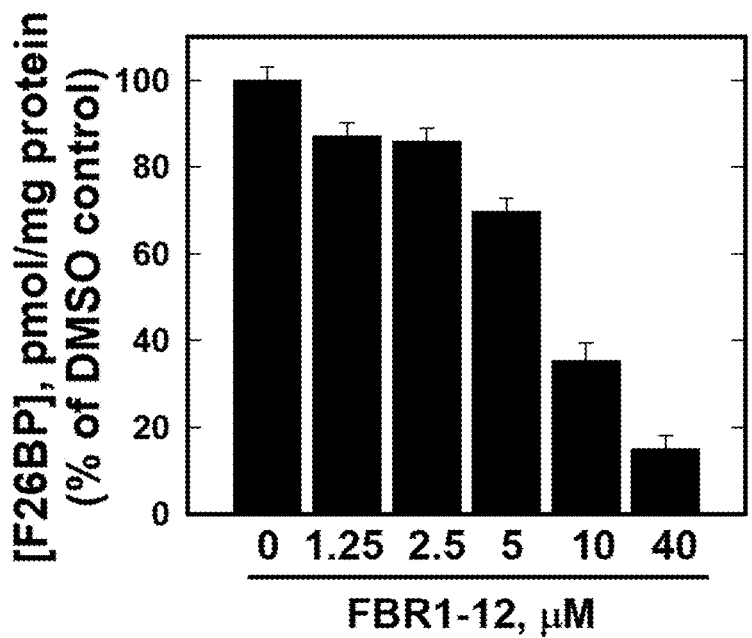
Figure 12:
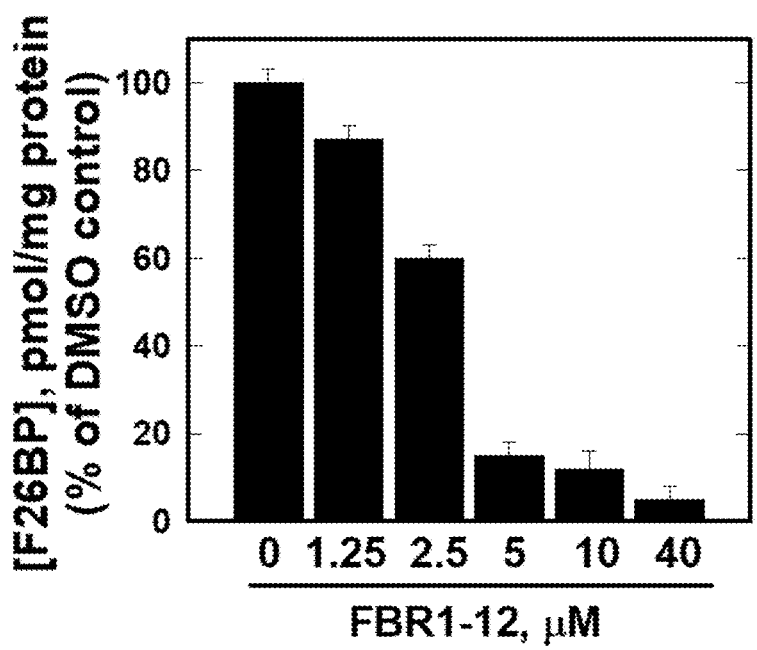

FIG. 12. Decrease in fructose-2,6-bisphosphate (F26BP) in cells by Formula (VIII).

Figure 13:
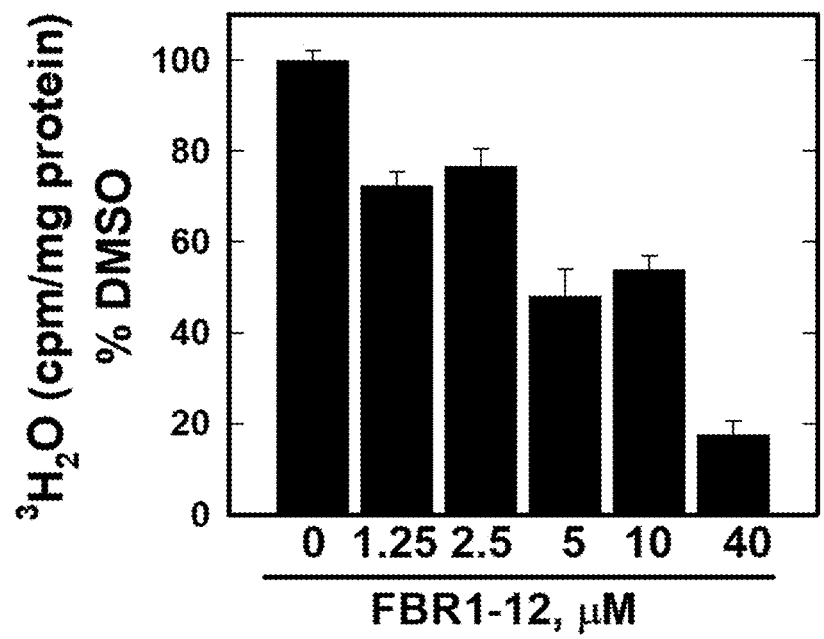
Figure 13:
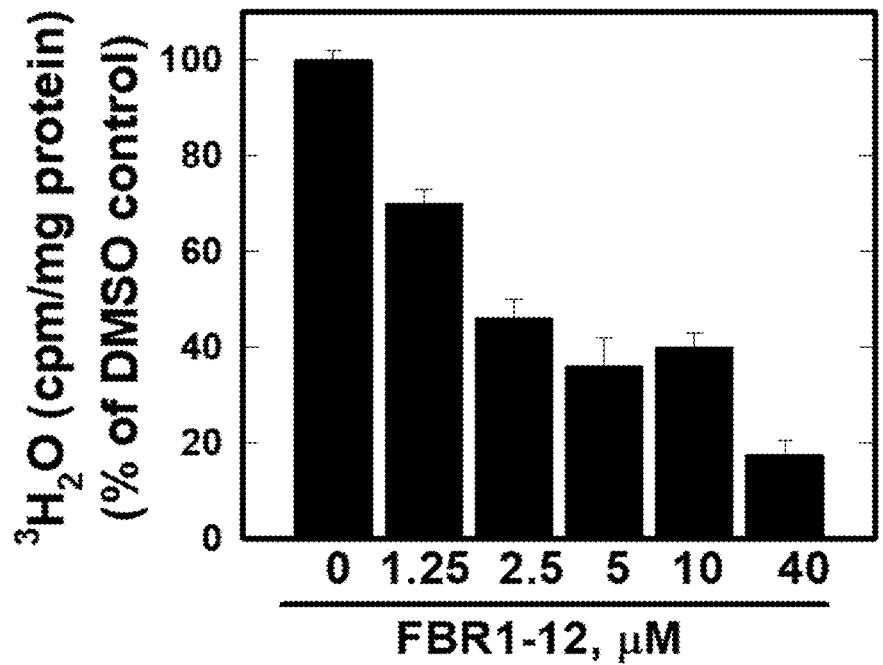

FIG. 13. Decrease in glycolysis in cells by Formula (VIII).

Figure 14:
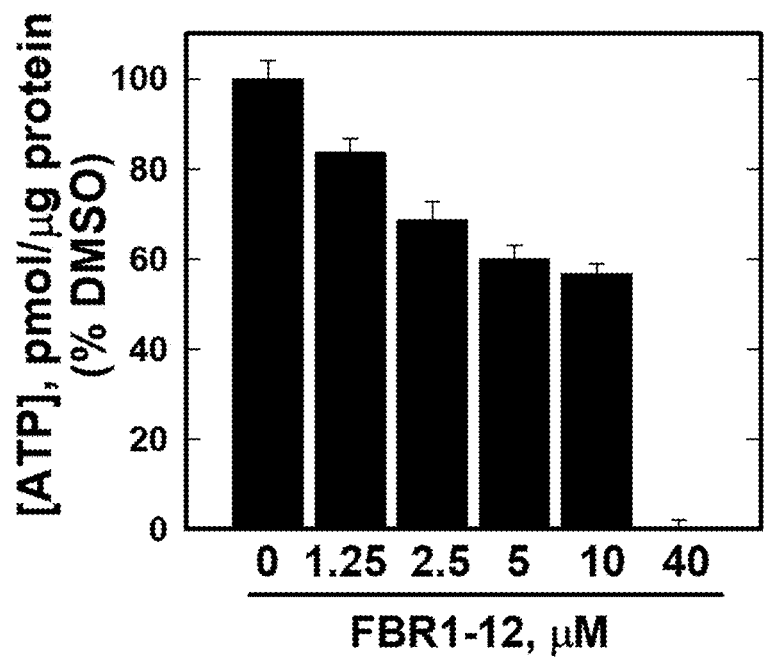
Figure 14:
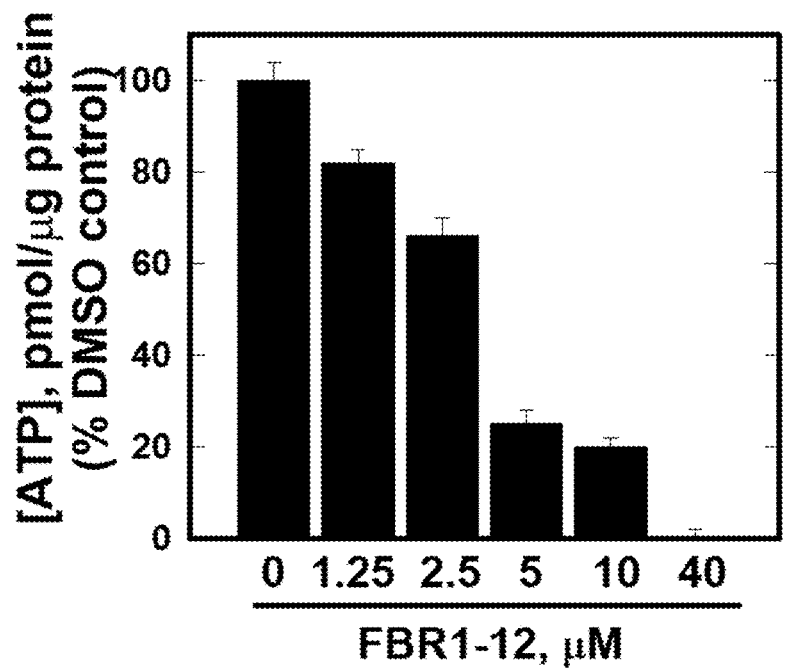

FIG. 14. Decrease in ATP production in cells by Formula (VIII).

Figure 15:
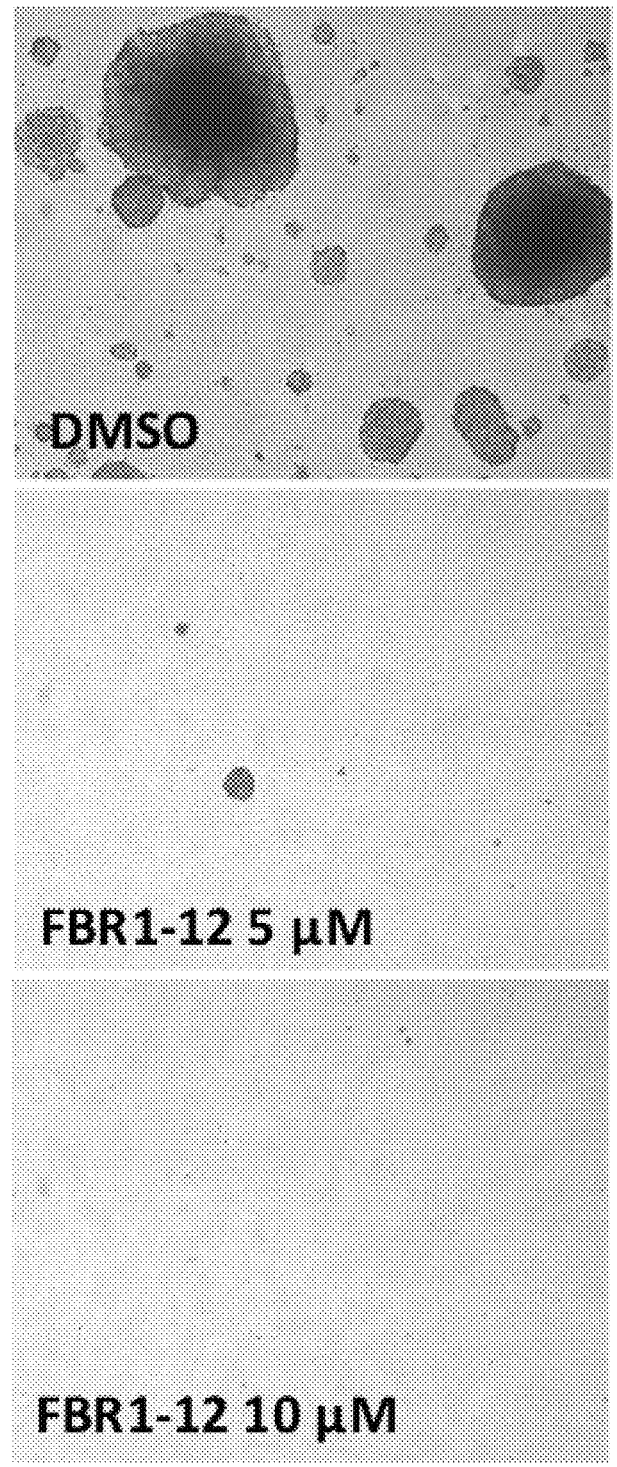
Figure 15:
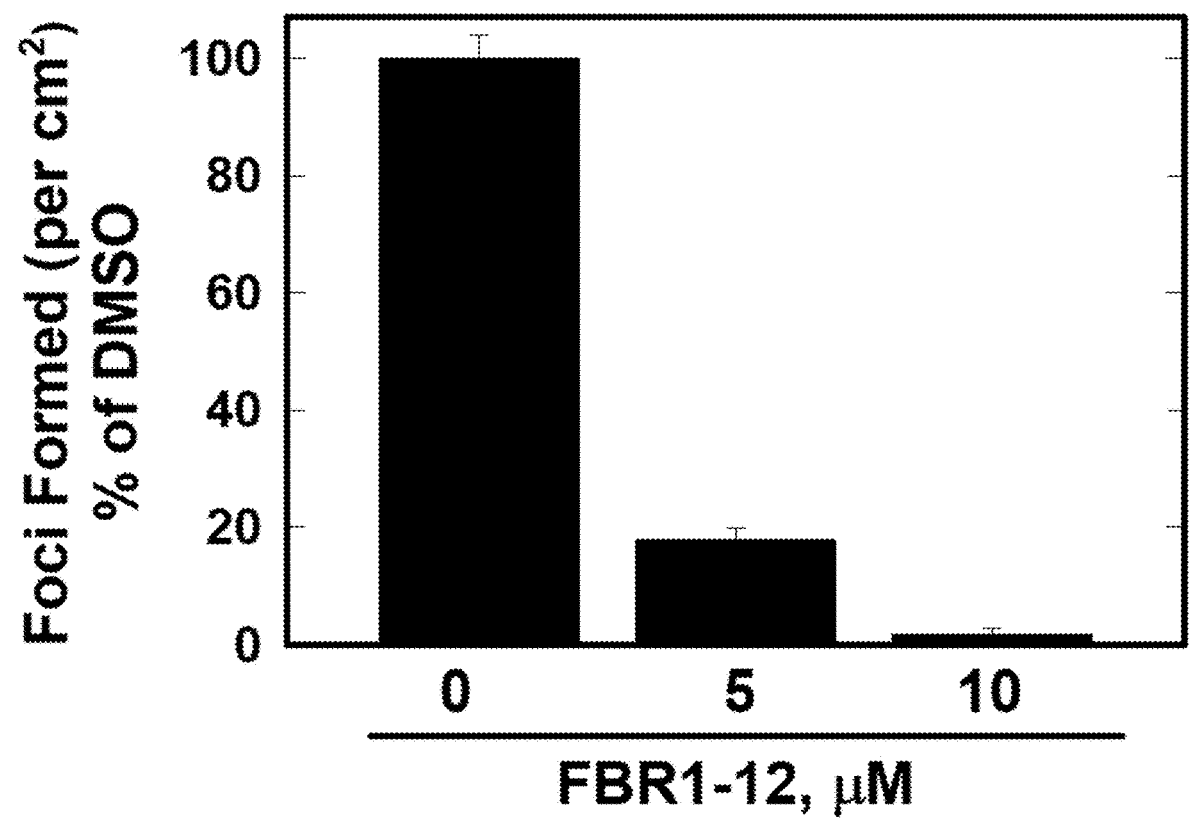

FIG. 15. Decrease in anchorage independent growth in cells by Formula (VIII).

Figure 16:
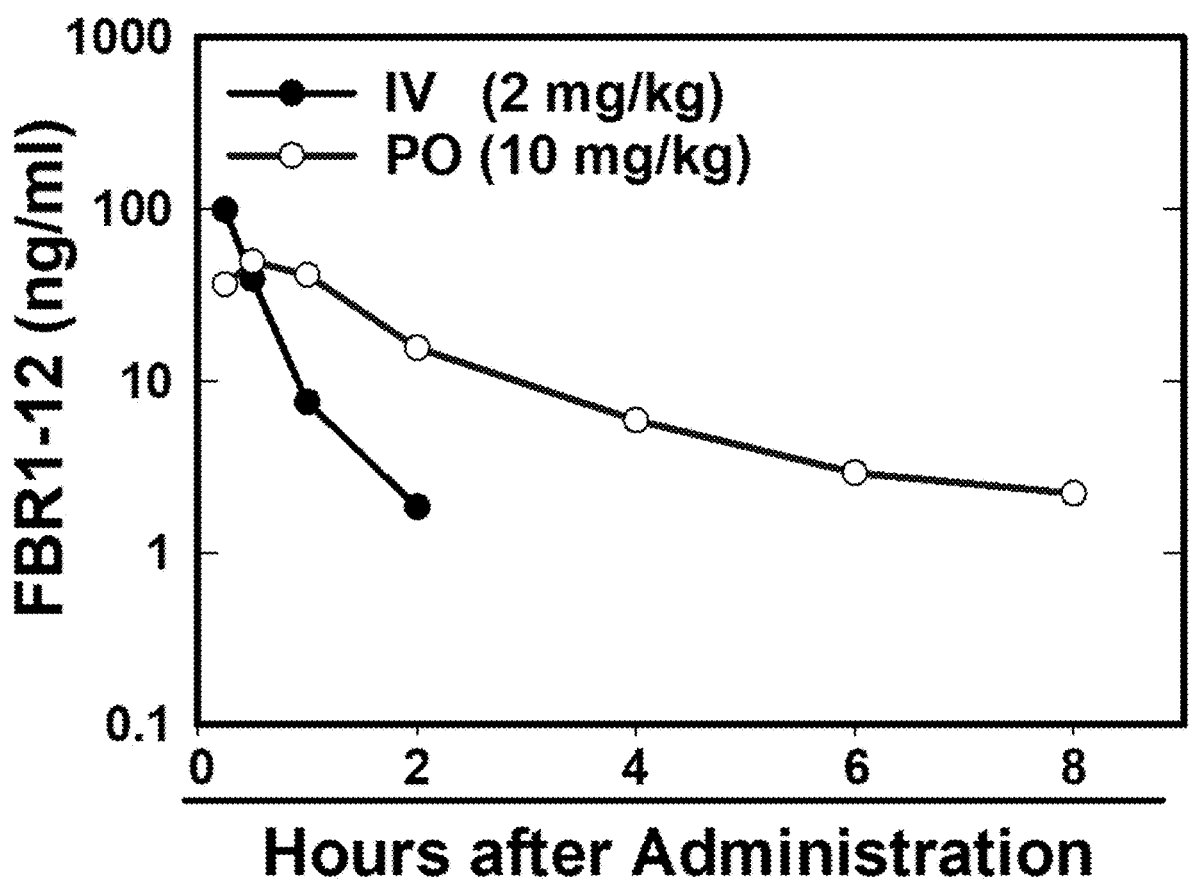

FIG. 16. Pharmacokinetic profile of Formula (VIII).

Figure 17:
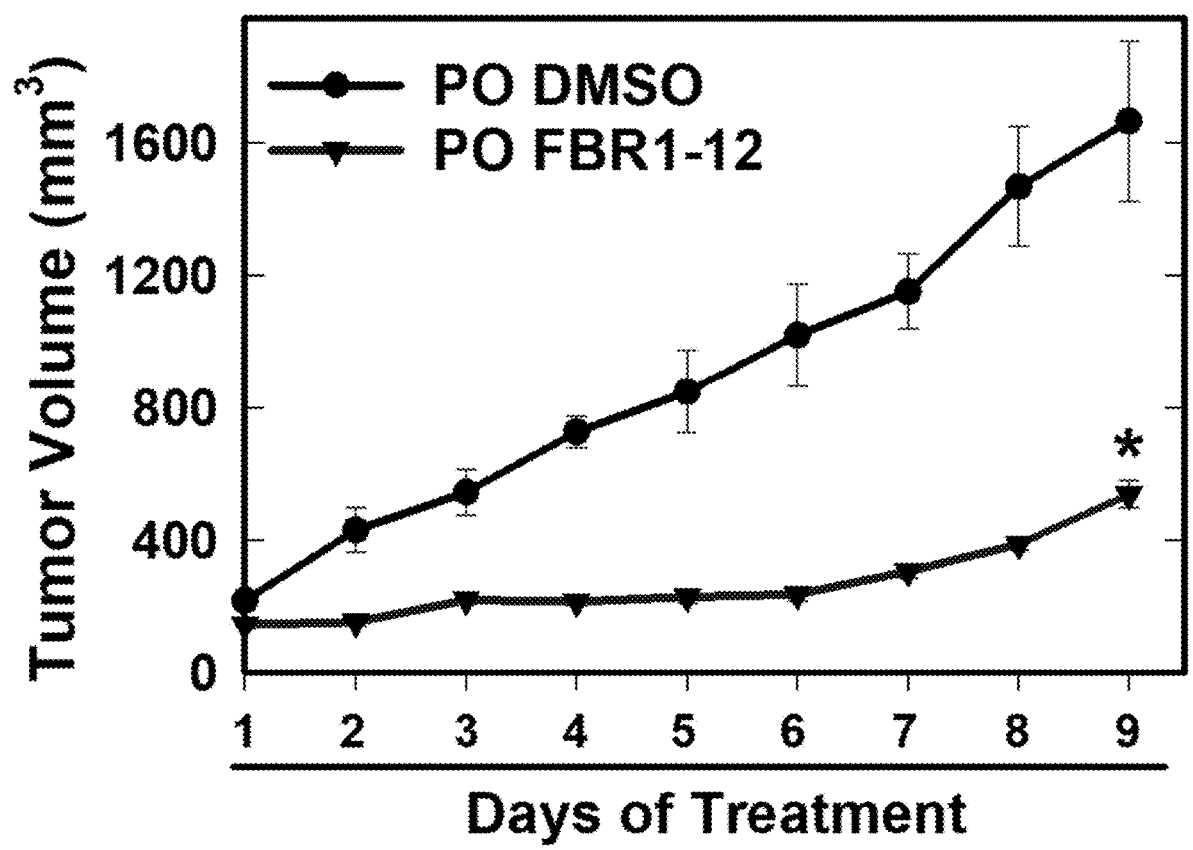

FIG. 17. Formula (VIII) decreases growth of tumors in vivo.

Figure 18:
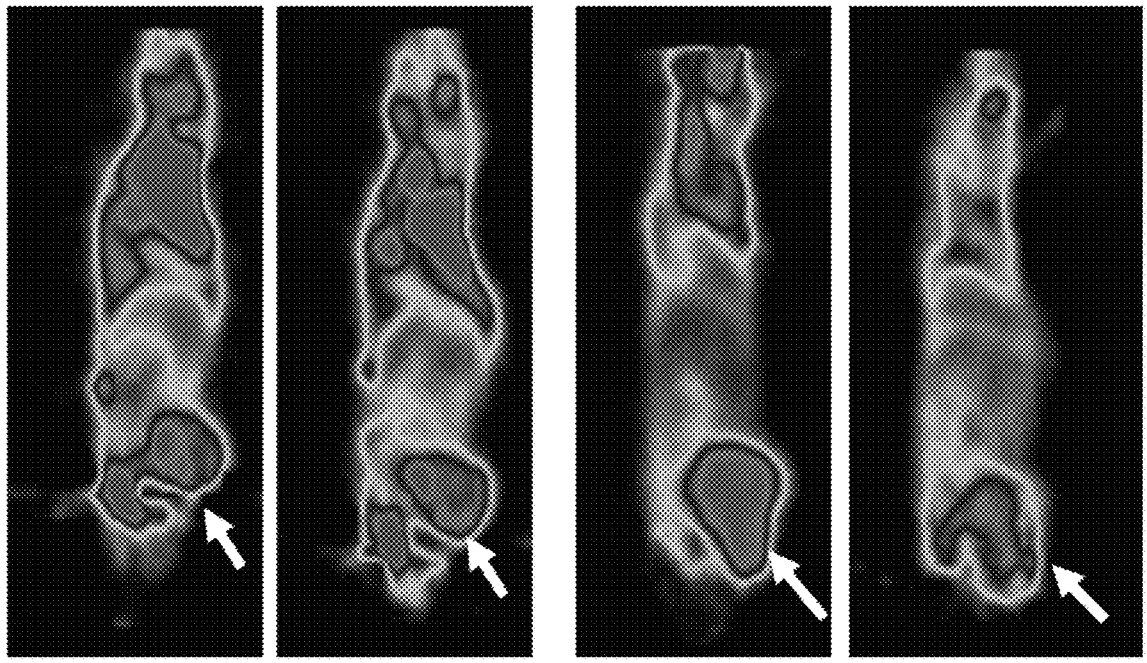
Figure 18:
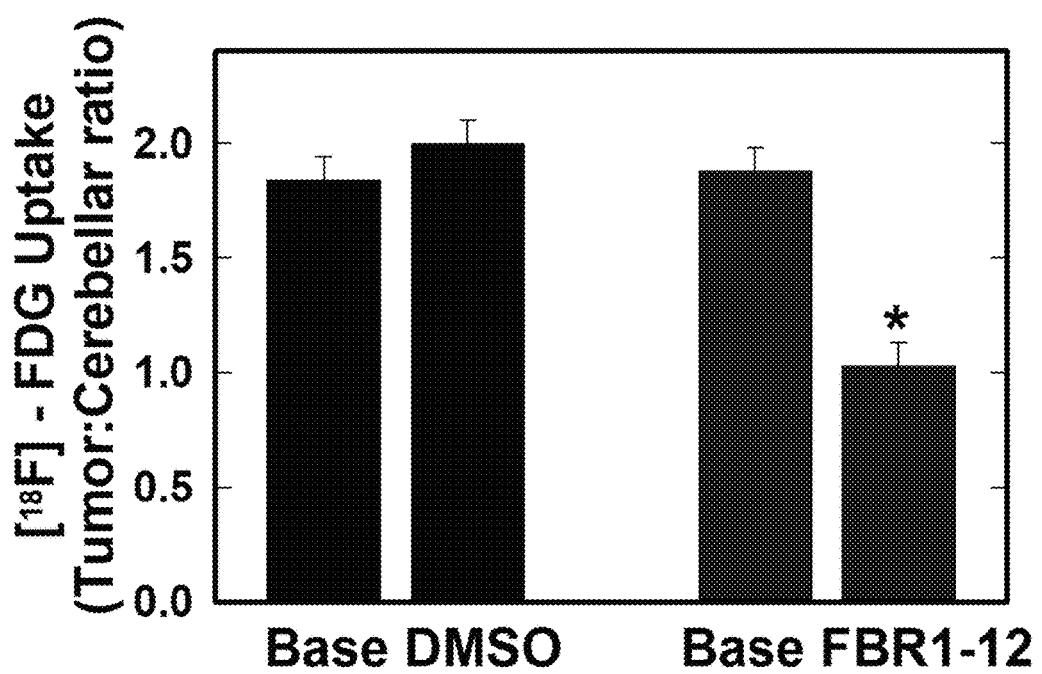

FIG. 18. Formula (VIII) decreases glucose uptake in tumors in vivo.

Figure 19:
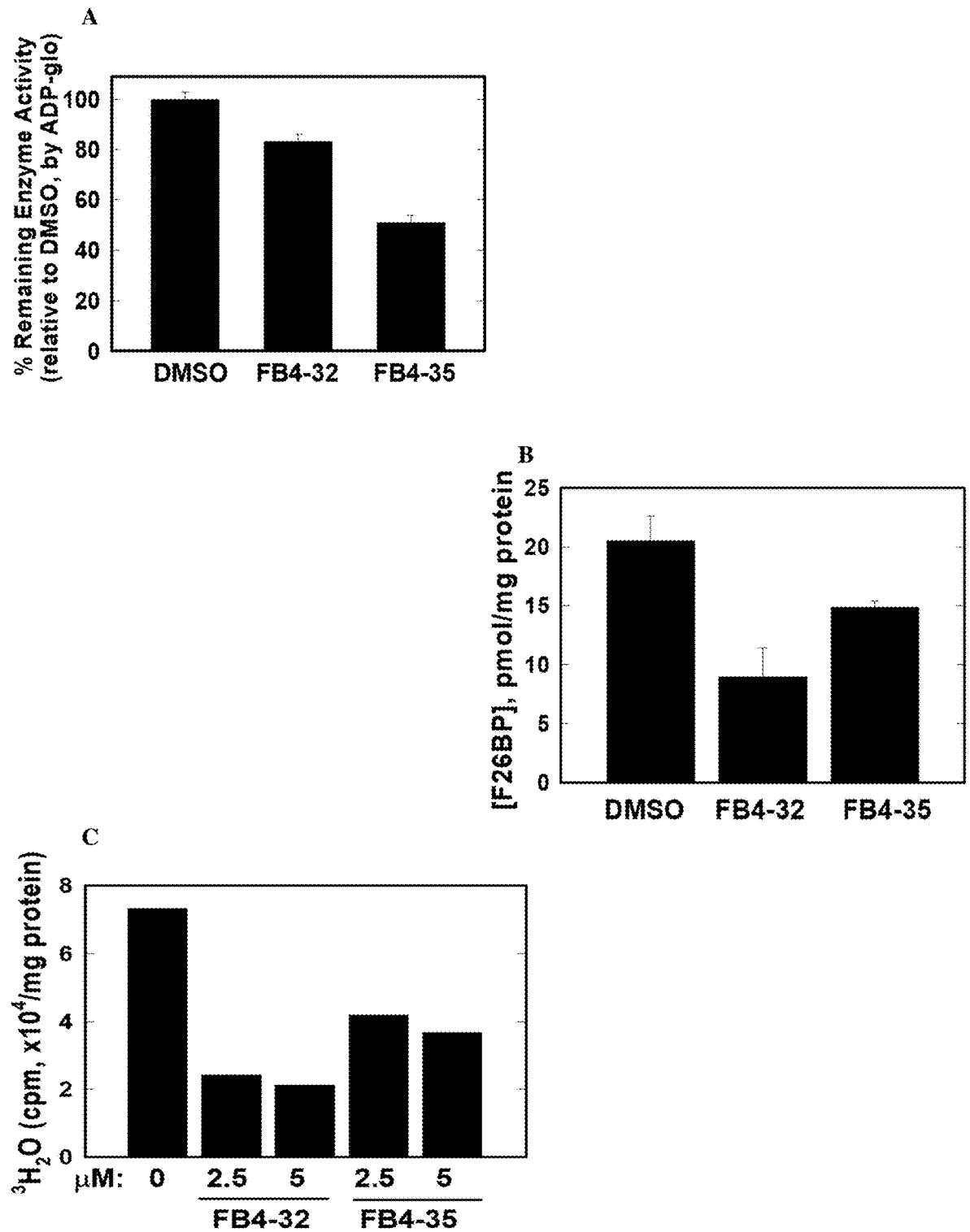
Figure 19:
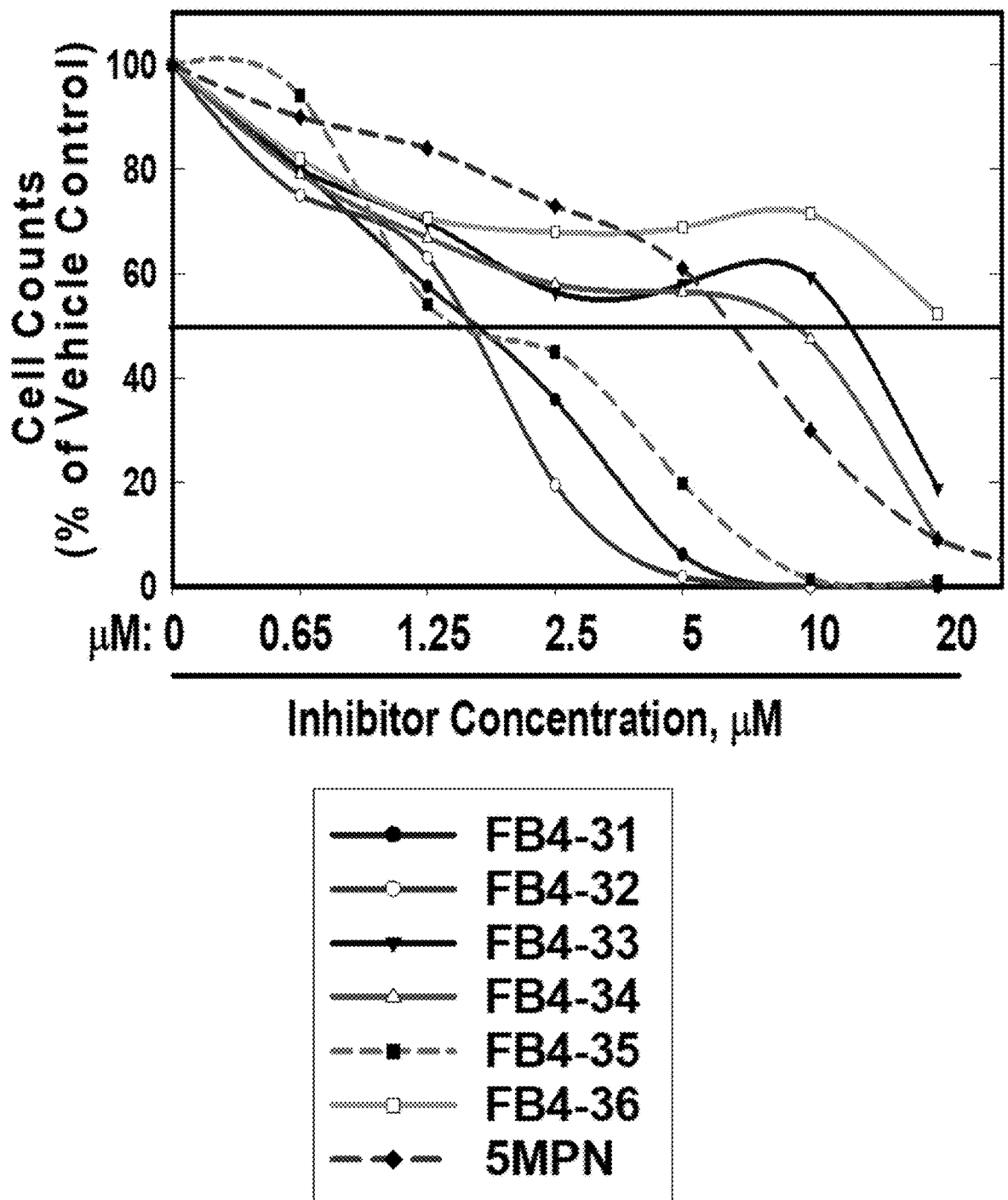

FIG. 19. FB4-32 and FB4-35 inhibit PFKFB4 enzyme activity, decrease fructose-2,6 bisphosphate production, proliferation and glycolysis in a human lung cancer cell line (H460).

Figure 20:
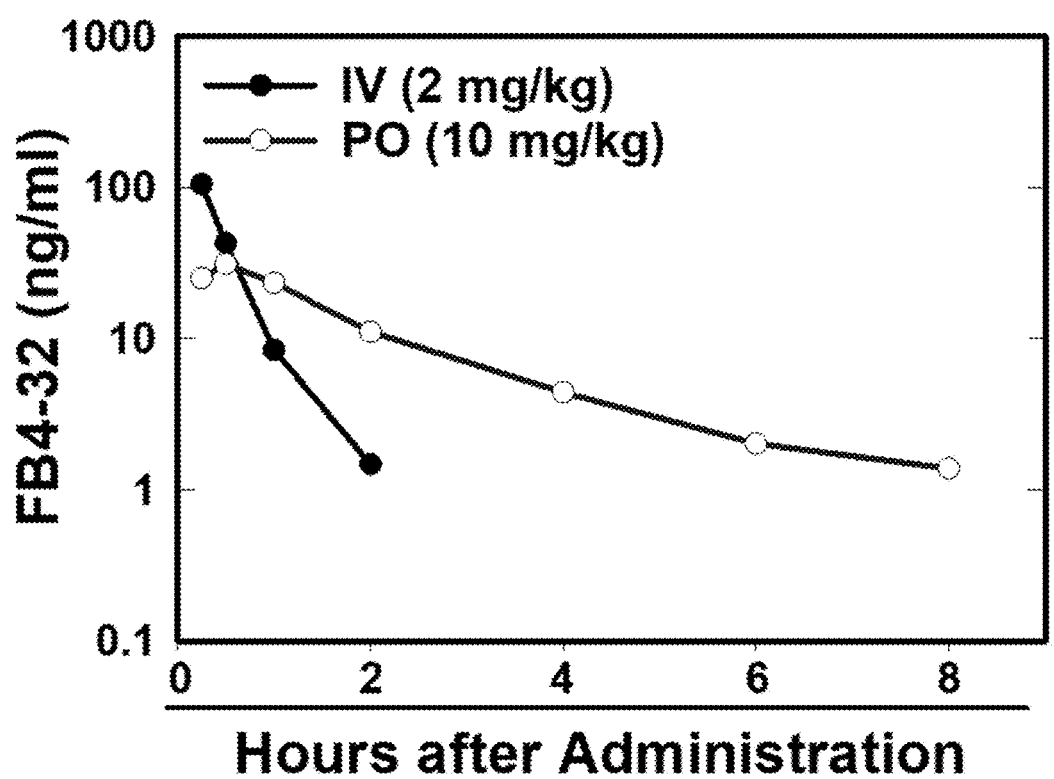

FIG. 20. Pharmacokinetic studies of FB4-32 demonstrate oral bioavailability.

DETAILED DESCRIPTION

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive compounds. Other embodiments include compositions (e.g., pharmaceutical compositions) comprising the inventive compound. Still other embodiments of the invention include compositions (e.g., pharmaceutical compositions) for treating, for example, certain diseases using the compounds. Some embodiments include methods of using the inventive compound (e.g., in compositions or in pharmaceutical compositions) for administering and treating (e.g., diseases such as cancer). Further embodiments include methods for making the inventive compounds. Other embodiments include PFKFB4 inhibitors and methods of using the same that can target neoplastic cells, including, such as, mechanisms within those cells that relate to the use of the glycolytic pathway. In other embodiments, small molecule PFKFB4 inhibitors are used to disrupt the kinase domain of PFKFB4 and, in some instances, decrease the glucose metabolism and growth of human cancers. Additional embodiments of the invention are also discussed herein.

Some embodiments of the invention include compounds of Formula (I) and a method of treating cancer in a subject in need of treatment comprises administering to the subject an effective amount of a compound having the Formula (I):

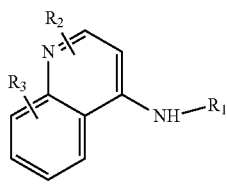

(I)

wherein:
$R_1$ is a $C_1$-$C_5$ alkyl nitrooxy;
$R_2$ can be present or absent, and when present is a $C_1$-$C_5$ alkyl;
$R_3$ can be present or absent, and when present is a $C_1$-$C_5$ alkoxy; and
wherein if $R_2$ is present and located on the nitrogen of the quinoline group, said nitrogen has a positive charge.

In some embodiments, the invention includes compounds of Formula (II) and a method of treating cancer in a subject in need of treatment comprises administering to the subject an effective amount of a compound having the Formula (II):

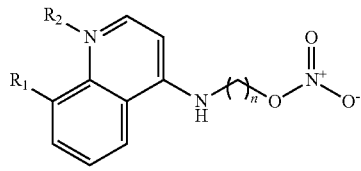

(II)

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge.

In other embodiments, the invention includes compounds of Formula (III) and a method of treating cancer in a subject in need of treatment comprises administering to the subject an effective amount of a compound having the Formula (III):

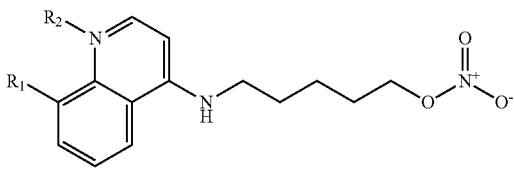

(III)

wherein:
$R_1$ can be present or absent, and when present is a $C_1$-$C_5$ alkoxy;
$R_2$ can be present or absent, and when present is a $C_1$-$C_5$ alkyl; and
wherein if $R_2$ is present, the nitrogen of the quinoline group has a positive charge.

In further embodiments, the invention includes compounds of Formula (IV) and a method of treating cancer in a subject in need of treatment thereof comprises administering to the subject an effective amount of a compound of:

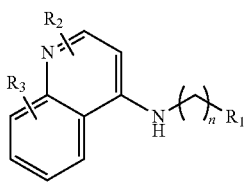

(IV)

wherein:
n is 1-6;
$R_1$ is carboxylic acid, methyl sulfamide, carboxylic acid methyl ester, hydroxide, nitrate, or tert-butyl carbamate;
$R_2$ can be present or absent, and when present is a $C_1$-$C_5$ alkyl;
$R_3$ can be present or absent, and when present is a $C_1$-$C_5$ alkoxy, $C_1$-$C_5$ alkyl, chlorine, or hydrogen; and
wherein if $R_2$ is present and located on the nitrogen of the quinoline group, said nitrogen has a positive charge. In other embodiments, $R_1$ is a carbonate, a carbamide, nitro sulfonamide, or a thiocarbonyl. In certain embodiments, the compound of formula (IV) includes the following compounds:
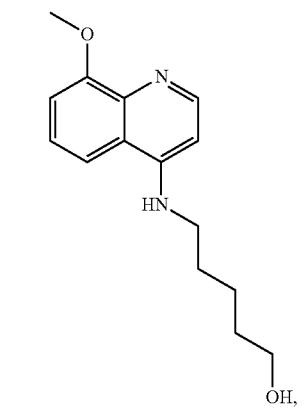
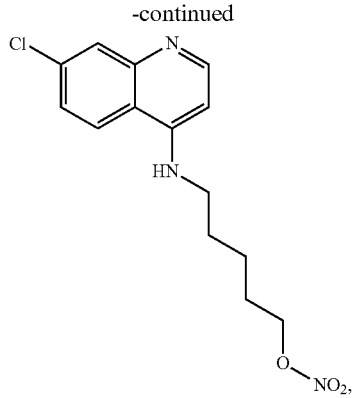
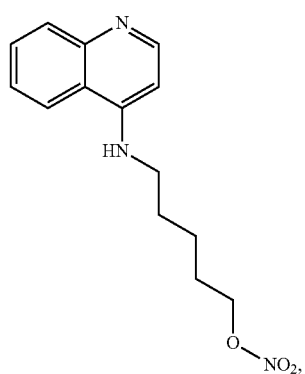 [SMILES: O=[N+]([O-])OCCCCCNc1ccnc2ccccc12]
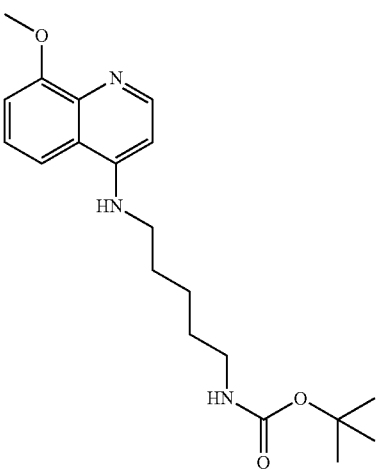
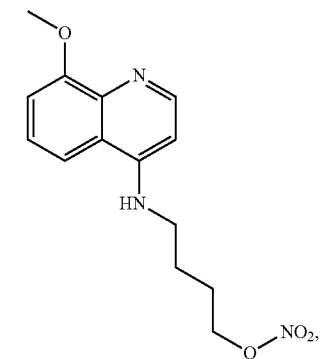
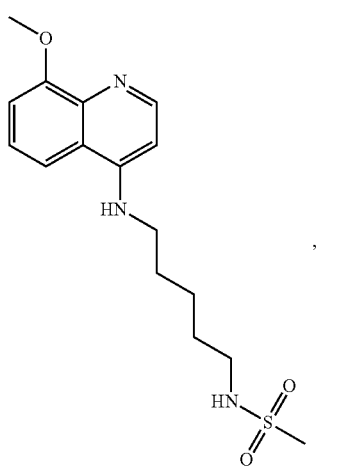

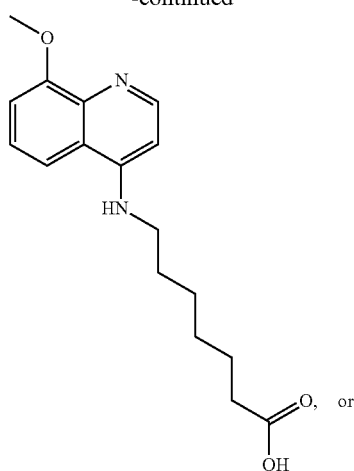

, or

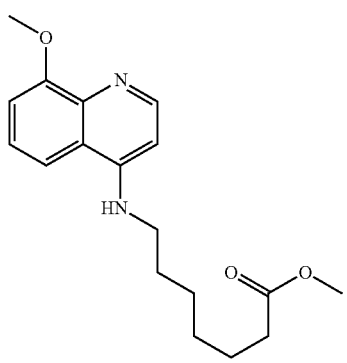

In other embodiments, the invention includes compounds of Formula (V) and a method of treating cancer in a subject in need of treatment thereof comprises administering to the subject an effective amount of a compound of:

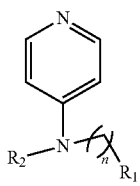

(V)

wherein:

n is 1-6;

$R_1$ nitrate; and $R_2$ is a hydrogen or nitrogen dioxide. In further embodiments, $R_1$ is carboxylic acid, methyl sulfamide, carboxylic acid methyl ester, hydroxide, nitrate, or tert-butyl carbamate. In even further embodiments, $R_1$ is a carbonate, a carbamide, nitro sulfonamide, or a thiocarbonyl. In certain embodiments, the compound of Formula (V) includes the compounds:

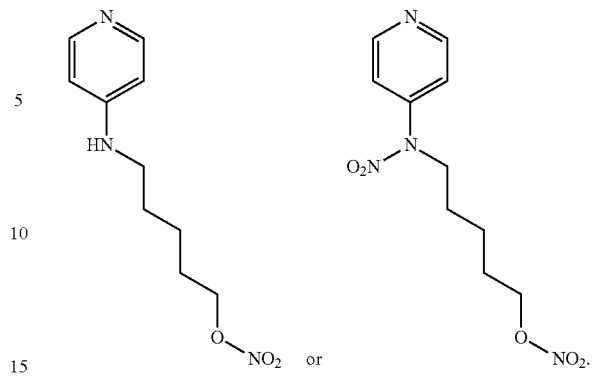

In additional embodiments, the invention includes a compound 5MPN and a method of treating cancer in a subject in need of treatment thereof comprises administering to the subject an effective amount of 5MPN.

In further embodiments, the invention includes a compound of MPN-2 and a method of treating cancer in a subject in need of treatment thereof comprises administering to the subject an effective amount of MPN-2.

In some embodiments, the invention includes compounds of Formula (VI) and a method of treating cancer in a subject in need of treatment thereof comprises an effective amount of compound:

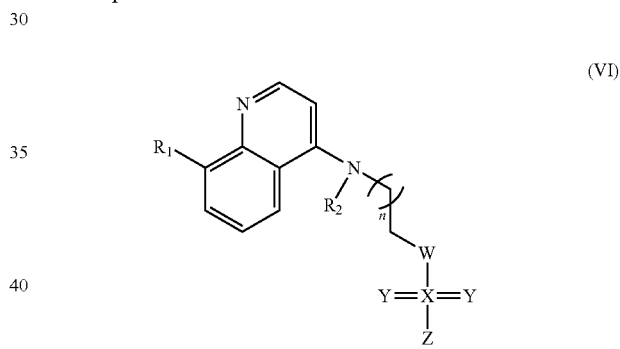

(VI)

wherein:

n is 2-6;

$R_1$ can be present or absent, and when present is a $C_1$-$C_5$ alkoxy, a $C_1$-$C_5$ alkyl, chlorine, or hydrogen;

$R_2$ can be present or absent, and when present is a hydrogen or nitrogen dioxide;

W is carbon, oxygen, nitrogen, hydrogen, methyl, methoxy, or hydroxide;

X can be present or absent, and when present is carbon, oxygen, nitrogen, or sulfur;

Y can be present or absent, and when present is oxygen, sulfur, or independently oxygen and sulfer and wherein one or two Ys may be present; and Z is can be present or absent, and when present is carbon, oxygen, nitrogen, hydrogen, methyl, or methoxy; and wherein if W is hydrogen, methyl, methoxy, or hydroxide, then X, Y, and Z is absent.

In some embodiments, the invention includes compounds of Formula (VII) and a method of treating cancer in a subject in need of treatment thereof comprises an effective amount of compound:

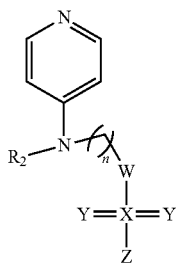

(VII)

wherein:
n is 1-6;
$R_2$ is a hydrogen or nitrogen dioxide;
W is carbon, oxygen, nitrogen, hydrogen, methyl, methoxy, or hydroxide;
X can be present or absent, and when present is carbon, oxygen, nitrogen, or sulfur;
Y can be present or absent, and when present is oxygen, sulfur, or independently oxygen and sulfer and wherein one or two Ys may be present; and
Z is can be present or absent, and when present is carbon, oxygen, nitrogen, hydrogen, methyl, or methoxy; and
wherein if W is hydrogen, methyl, methoxy, or hydroxide, then X, Y, and Z is absent.

In some embodiments, the invention includes compounds of Formula (VIII) and a method of treating cancer in a subject in need of treatment thereof comprises an effective amount of compound:

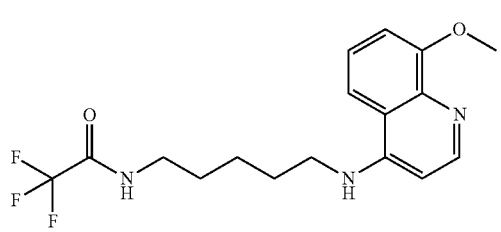

(VIII)

(2,2,2-trifluoro-N-(5-((8-methoxyquinolin-4-yl)amino)pentyl)acetamide).

As used herein (unless otherwise specified), the term "alkyl" means a monovalent, straight or branched hydrocarbon chain. For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—). Examples of alkoxy groups include, but are not limited to, methoxy (sometimes shown as MeO), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "halogen" means monovalent Cl, F, Br, or I.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be substituted.

Some compounds of the invention can have one or more chiral centers and can exist in and be isolated in optically active and racemic forms, for any of the one or more chiral centers. Some compounds can exhibit polymorphism. The compounds of the present invention encompass any optically active, racemate, stereoisomer form, polymorphism, or mixtures thereof. If a chiral center does not provide an indication of its configuration (i.e., R or S) in a chemical structure, it should be considered to represent R, S or a racemate.

In some embodiments, the invention includes compounds of Formula (IX)

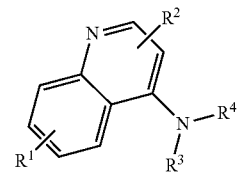

(IX)

and salts, optical isomers, geometric isomers, salts of isomers, and derivatives thereof,
wherein
$R^1$ is a monovalent H, carboxy (—$CO_2$H), nitro (—$NO_2$), nitrate (—$ONO_2$), sulfo (—$SO_3$H), halogen (e.g., F, Cl, Br, or I), $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), or $C_1$-$C_7$ alkoxy (e.g., $C_1$, $C_2$, $C_3$, $C_4$, $C_5$, $C_6$, or $C_7$ alkoxy), which $C_1$-$C_8$ alkyl, $C_2$-$C_8$ alkenyl, $C_2$-$C_8$ alkynyl, or $C_1$-$C_7$ alkoxy can optionally be substituted with one or more (e.g., 0, 1, 2, 3, 4, 5, or 6) of halogen (e.g., F, Cl, Br, or I), hydroxy (—OH), $C_1$-$C_3$ alkyl (e.g., $C_1$, $C_2$, or $C_3$ alkyl), $C_1$-$C_2$ alkoxy (e.g., $C_1$ or $C_2$ alkoxy), methanoly (—COH), carboxy (—CO$_2$H), nitro (—NO$_2$), nitrate (—ONO$_2$), cyano (—CN), amino (—NH$_2$), carbamoyl (—CONH$_2$), ethynyl (—CCH), or sulfo (—SO$_3$H);

$R^2$ is a monovalent H, carboxy (—CO$_2$H), nitro (—NO$_2$), nitrate (—ONO$_2$), sulfo (—SO$_3$H), halogen (e.g., F, Cl, Br, or I), $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), or $C_1$-$C_7$ alkoxy (e.g., $C_1$, $C_2$, $C_3$, $C_4$, $C_5$, $C_6$, or $C_7$ alkoxy), which $C_1$-$C_8$ alkyl, $C_2$-$C_8$ alkenyl, $C_2$-$C_8$ alkynyl, or $C_1$-$C_7$ alkoxy can optionally be substituted with one or more (e.g., 0, 1, 2, 3, 4, 5, or 6) of halogen (e.g., F, Cl, Br, or I), hydroxy (—OH), $C_1$-$C_3$ alkyl (e.g., $C_1$, $C_2$, or $C_3$ alkyl), $C_1$-$C_2$ alkoxy (e.g., $C_1$ or $C_2$ alkoxy), methanoly (—COH), carboxy (—CO$_2$H), nitro (—NO$_2$), nitrate (—ONO$_2$), cyano (—CN), amino (—NH$_2$), carbamoyl (—CONH$_2$), ethynyl (—CCH), or sulfo (—SO$_3$H);

$R^3$ is a monovalent $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), or $C_1$-$C_9$ alkoxy (e.g., $C_1$, $C_2$, $C_3$, $C_4$, $C_5$, $C_6$, $C_7$, $C_8$, or $C_9$ alkoxy), which $C_1$-$C_{10}$ alkyl, $C_2$-$C_{10}$ alkenyl, $C_2$-$C_{10}$ alkynyl, or $C_1$-$C_9$ alkoxy can optionally be substituted with one or more (e.g., 0, 1, 2, 3, 4, 5, or 6) of halogen (e.g., F, Cl, Br, or I), hydroxy (—OH), $C_1$-$C_3$ alkyl (e.g., $C_1$, $C_2$, or $C_3$ alkyl), $C_1$-$C_2$ alkoxy (e.g., $C_1$ or $C_2$ alkoxy), methanoly (—COH), —CO($C_1$-$C_3$ alkyl), carboxy (—CO$_2$H), —CO$_2$($C_1$-$C_6$ alkyl) (e.g., —CO$_2$(CH$_3$)), nitro (—NO$_2$), nitrate (—ONO$_2$), cyano (—CN), amino (—NH$_2$), —N($C_1$-$C_6$ alkyl)H, —N($C_1$-$C_6$ alkyl)($C_1$-$C_6$ alkyl), carbamoyl (—CONH$_2$), ethynyl (—CCH), sulfo (—SO$_3$H), —SO$_3$($C_1$-$C_6$ alkyl) (e.g., —SO$_3$—CH$_3$),

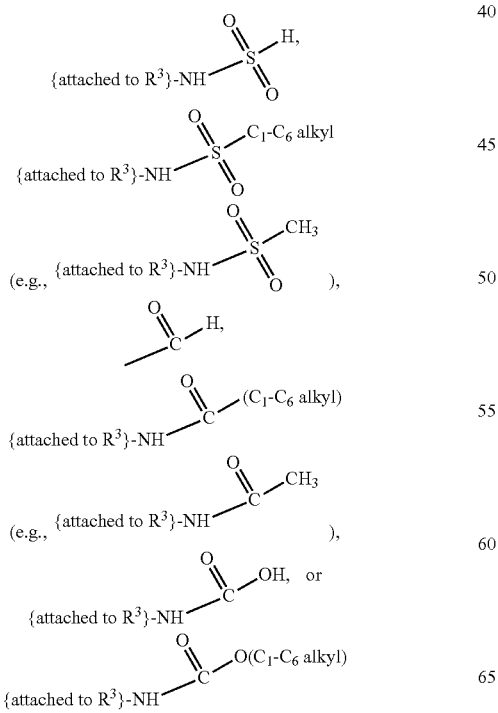

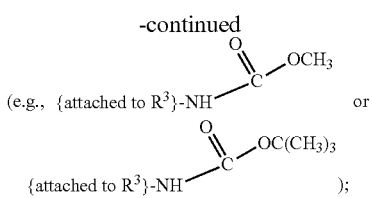

$R^4$ is a monovalent H, carboxy (—CO$_2$H), nitro (—NO$_2$), sulfo (—SO$_3$H), halogen (e.g., F, Cl, Br, or I), $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), or $C_1$-$C_7$ alkoxy (e.g., $C_1$, $C_2$, $C_3$, $C_4$, $C_5$, $C_6$, or $C_7$ alkoxy), which $C_1$-$C_8$ alkyl, $C_2$-$C_8$ alkenyl, $C_2$-$C_8$ alkynyl, or $C_1$-$C_7$ alkoxy can optionally be substituted with one or more (e.g., 0, 1, 2, 3, 4, 5, or 6) of halogen (e.g., F, Cl, Br, or I), hydroxy (—OH), $C_1$-$C_3$ alkyl (e.g., $C_1$, $C_2$, or $C_3$ alkyl), $C_1$-$C_2$ alkoxy (e.g., $C_1$ or $C_2$ alkoxy), methanoly (—COH), carboxy (—CO$_2$H), nitro (—NO$_2$), nitrate (—NO$_3$), cyano (—CN), amino (—NH$_2$), carbamoyl (—CONH$_2$), ethynyl (—CCH), or sulfo (—SO$_3$H);

$R^1$ can be attached to any position on the quinoline ring but is not attached to the nitrogen;

$R^2$ can be attached to any position on the quinoline ring including being attached to the nitrogen; and if $R^3$ comprises a substitution with one or more of methanoly (—COH), —CO($C_1$-$C_3$ alkyl), carboxy (—CO$_2$H), —CO$_2$($C_1$-$C_6$ alkyl) (e.g., —CO$_2$(CH$_3$)), amino (—NH$_2$), —N($C_1$-$C_6$ alkyl)H, —N($C_1$-$C_6$ alkyl)($C_1$-$C_6$ alkyl), carbamoyl (—CONH$_2$), ethynyl (—CCH), sulfo (—SO$_3$H), —SO$_3$($C_1$-$C_6$ alkyl) (e.g., —SO$_3$—CH$_3$),

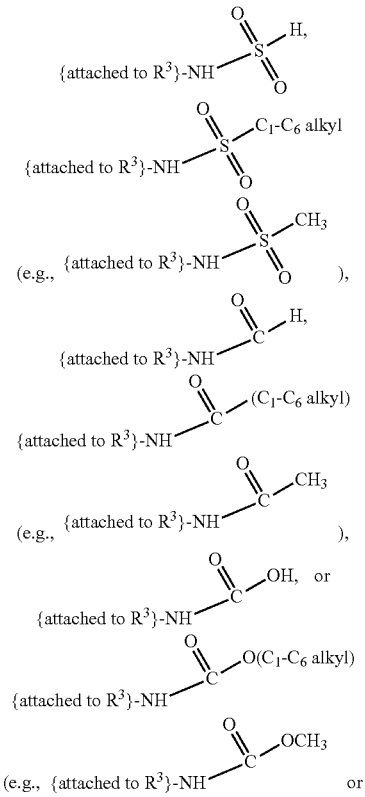

-continued

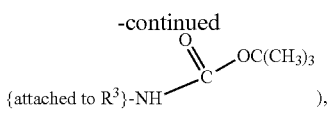

then each of methanoly (—COH), —CO(C$_1$-C$_3$ alkyl), carboxy (—CO$_2$H), —CO$_2$(C$_1$-C$_6$ alkyl) (e.g., —CO$_2$(CH$_3$)), amino (—NH$_2$), —N(C$_1$-C$_6$ alkyl)H, —N(C$_1$-C$_6$ alkyl)(C$_1$-C$_6$ alkyl), carbamoyl (—CONH$_2$), ethynyl (—CCH), sulfo (—SO$_3$H), —SO$_3$(C$_1$-C$_6$ alkyl) (e.g., —SO$_3$—CH$_3$),

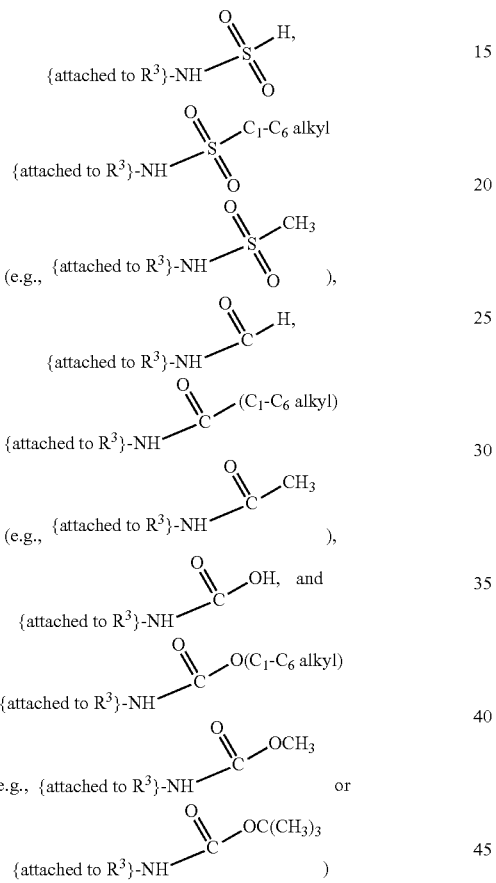

can be independently and optionally substituted with one or more (e.g., 0, 1, 2, 3, 4, 5, 6, 7, 8, 9, 10, 11, or 12) of halogen (e.g., F, Cl, Br, or I), hydroxy (—OH), C$_1$-C$_4$ alkyl (e.g., C$_1$, C$_2$, C$_3$, or C$_4$ alkyl), C$_2$-C$_4$ alkenyl (e.g., C$_2$, C$_3$, or C$_4$ alkenyl), C$_2$-C$_4$ alkynyl (e.g., C$_2$, C$_3$, or C$_4$ alkynyl), C$_1$-C$_4$ alkoxy (e.g., C$_1$, C$_2$, C$_3$, or C$_4$ alkoxy), methanoly (—COH), carboxy (—CO$_2$H), nitro (—NO$_2$), nitrate (—ONO$_2$), cyano (—CN), amino (—NH$_2$), —NH(C$_1$-C$_4$ alkyl) (e.g., —NHCH$_2$CH$_3$), —N(C$_1$-C$_4$ alkyl)(C$_1$-C$_4$ alkyl) (e.g., —N(CH$_3$)$_2$), carbamoyl (—CONH$_2$), ethynyl (—CCH), or sulfo (—SO$_3$H).

In other embodiments, the compound of Formula (IX)
R$^1$ is H, C$_1$-C$_5$ alkoxy (e.g., methoxy) or halogen (e.g., Cl);
R$^2$ is H or C$_1$-C$_5$ alkyl (e.g., methyl);
R$^2$ is attached to the nitrogen of the quinoline ring;
R$^3$ is C$_1$-C$_6$ alkyl substituted with one or more of hydroxyl, nitro, nitrate, carboxy (—CO$_2$H), —CO$_2$(C$_1$-C$_6$ alkyl) (e.g., —C$_2$(CH$_3$)),

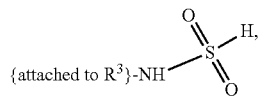

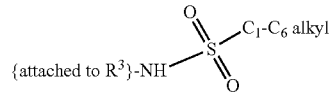

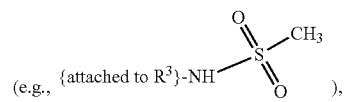

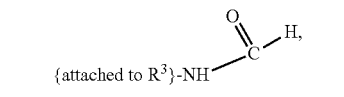

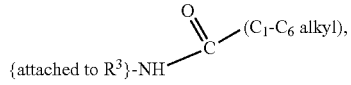

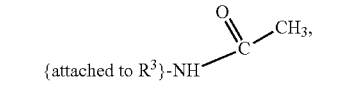

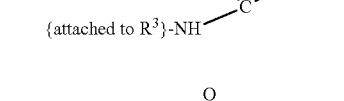

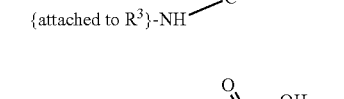

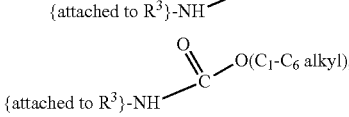

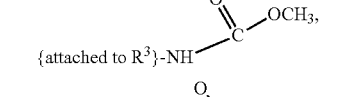

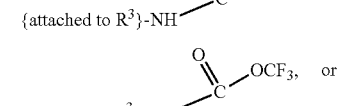

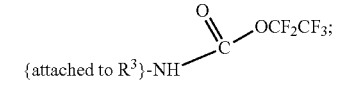

or
R$^4$ is H;
or a combination thereof.

In other embodiments, the compound of Formula (IX) is selected from

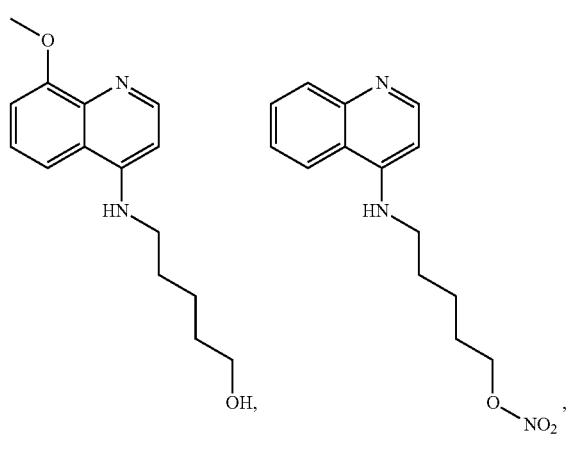
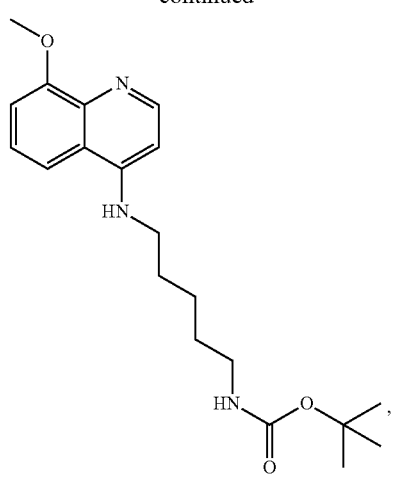
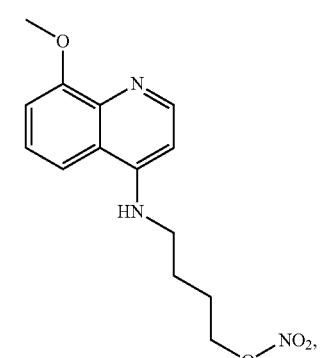
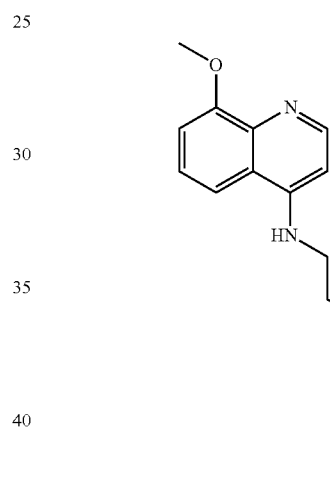
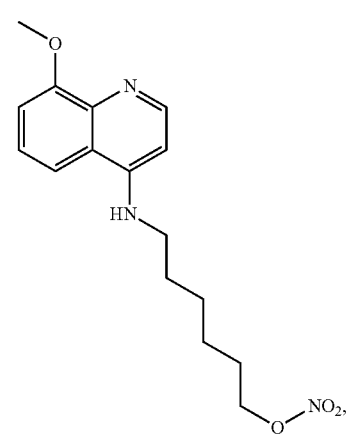
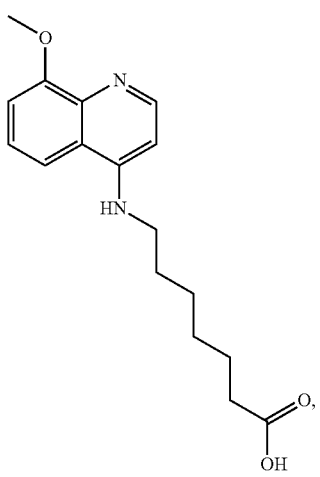
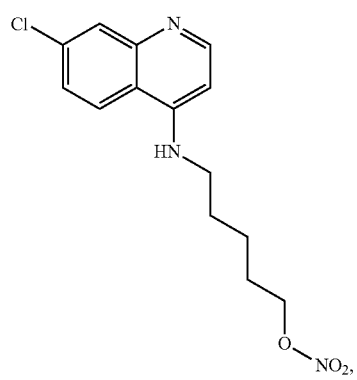

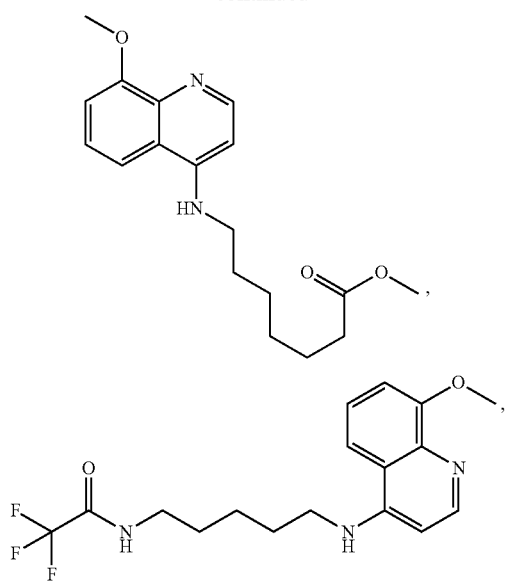
5MPN, and MPN-2.
In certain embodiments, the compound of Formula (IX) is selected from
FB4-31
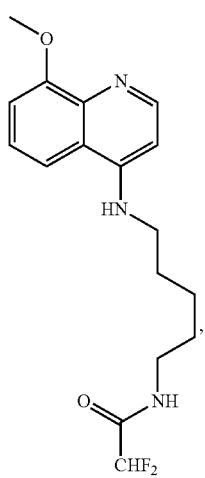
FB4-32
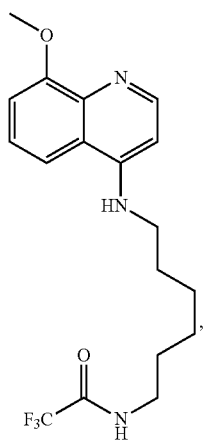
FB4-33
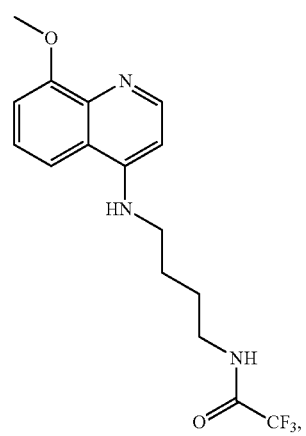
FB4-34
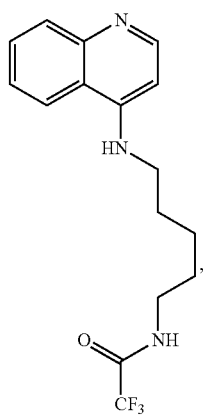
FB4-35
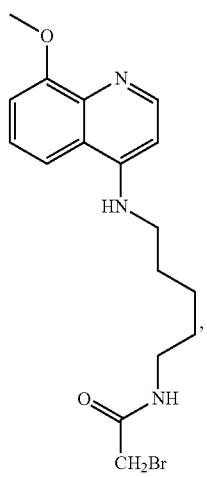

-continued

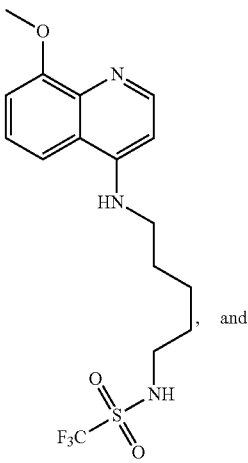

FB4-36

FB4-37

Some embodiments of the invention include a compound selected from a compound of Formula (X),

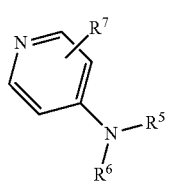

(X)

and
salts, optical isomers, geometric isomers, salts of isomers, and derivatives thereof, wherein $R^5$ is a monovalent H, carboxy (—$CO_2H$), nitro (—$NO_2$), sulfo (—$SO_3H$), halogen (e.g., F, Cl, Br, or I), $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), or $C_1$-$C_7$ alkoxy (e.g., $C_1$, $C_2$, $C_3$, $C_4$, $C_5$, $C_6$, or $C_7$ alkoxy), which $C_1$-$C_8$ alkyl, $C_2$-$C_8$ alkenyl, $C_2$-$C_8$ alkynyl, or $C_1$-$C_7$ alkoxy can optionally be substituted with one or more (e.g., 0, 1, 2, 3, 4, 5, or 6) of halogen (e.g., F, Cl, Br, or I), hydroxy (—OH), $C_1$-$C_3$ alkyl (e.g., $C_1$, $C_2$, or $C_3$ alkyl), $C_1$-$C_2$ alkoxy (e.g., $C_1$ or $C_2$ alkoxy), methanoly (—COH), carboxy (—$CO_2H$), nitro (—$NO_2$), nitrate (—$ONO_2$), cyano (—CN), amino (—$NH_2$), carbamoyl (—$CONH_2$), ethynyl (—CCH), or sulfo (—$SO_3H$);

$R^6$ is a monovalent $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), or $C_1$-$C_7$ alkoxy (e.g., $C_1$, $C_2$, $C_3$, $C_4$, $C_5$, $C_6$, or $C_7$ alkoxy), which $C_1$-$C_8$ alkyl, $C_2$-$C_8$ alkenyl, $C_2$-$C_8$ alkynyl, or $C_1$-$C_7$ alkoxy can optionally be substituted with one or more (e.g., 0, 1, 2, 3, 4, 5, or 6) of halogen (e.g., F, Cl, Br, or I), hydroxy (—OH), $C_1$-$C_3$ alkyl (e.g., $C_1$, $C_2$, or $C_3$ alkyl), $C_1$-$C_2$ alkoxy (e.g., $C_1$ or $C_2$ alkoxy), methanoly (—COH), carboxy (—$CO_2H$), nitro (—$NO_2$), nitrate (—$ONO_2$), cyano (—CN), amino (—$NH_2$), carbamoyl (—$CONH_2$), ethynyl (—CCH), or sulfo (—$SO_3H$);

$R^7$ is a monovalent H, carboxy (—$CO_2H$), nitro (—$NO_2$), nitrate (—$ONO_2$), sulfo (—$SO_3H$), halogen (e.g., F, Cl, Br, or I), $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_5$ alkynyl (e.g., $C_2$, $C_3$, $C_4$, $C_5$, $C_6$, $C_7$, or $C_8$ alkynyl), or $C_1$-$C_7$ alkoxy (e.g., $C_1$, $C_2$, $C_3$, $C_4$, $C_5$, $C_6$, or $C_7$ alkoxy), which $C_1$-$C_8$ alkyl, $C_2$-$C_8$ alkenyl, $C_2$-$C_8$ alkynyl, or $C_1$-$C_7$ alkoxy can optionally be substituted with one or more (e.g., 0, 1, 2, 3, 4, 5, or 6) of halogen (e.g., F, Cl, Br, or I), hydroxy (—OH), $C_1$-$C_3$ alkyl (e.g., $C_1$, $C_2$, or $C_3$ alkyl), $C_1$-$C_2$ alkoxy (e.g., $C_1$ or $C_2$ alkoxy), methanoly (—COH), carboxy (—$CO_2H$), nitro (—$NO_2$), nitrate (—$ONO_2$), cyano (—CN), amino (—$NH_2$), carbamoyl (—$CONH_2$), ethynyl (—CCH), or sulfo (—$SO_3H$); and $R^7$ can be attached to any position on the ring including being attached to the nitrogen.

In other embodiments relating to the compounds Formula (X), $R^5$ is H or nitro;

$R^6$ is $C_1$-$C_6$ alkyl, $C_1$-$C_6$ alkyl substituted with a nitro (e.g., substituted with nitro at a terminal methyl group), or $C_1$-$C_6$ alkyl substituted with a nitrate (e.g., substituted with nitrate at a terminal methyl group);

$R^7$ is H, halogen (e.g., F, Cl, Br, or I), hydroxy (—OH), $C_1$-$C_3$ alkyl (e.g., $C_1$, $C_2$, or $C_3$ alkyl), or $C_1$-$C_2$ alkoxy ($C_1$, or $C_2$ alkoxy); or $R^7$ is not attached to the nitrogen;

or a combination thereof.

In some embodiments, one or more compounds of the invention (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be part of a composition or a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the composition or pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the composition or pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The composition or pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the composition or pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In some embodiments, the composition or pharmaceutical composition can include a unit dose of one or more compounds of the invention (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

"Cancer" includes but is not limited to diseases caused by uncontrolled cell division and the ability of cells to metastasize, or to establish new growth in additional sites. It will be appreciated that the administration to a subject of an effective amount of the presently-disclosed small molecule antagonists of the kinase domain of PFKFB4 can provide therapy for a wide variety of cancers including, but not limited to lung, breast, colon, ovarian, brain, liver, pancreas, prostate, melanoma, malignant melanoma, non-melanoma skin cancers, (and solid tumors thereof) as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS. In certain embodiments of a method of treating cancer in a subject in need of treatment thereof comprising administering to the subject an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), the cancer is selected from breast cancer, brain cancer, melanoma, lung cancer, colon cancer, and prostate cancer.

As used herein, the term "treating" (and its variations, such as "treatment") is to be considered in its broadest context. The term "treating" relates to any treatment of cancer, including but not limited to prophylactic treatment and therapeutic treatment. The term "treating" does not necessarily imply that an animal is treated until total recovery. "Treating" includes any effect, e.g., lessening, reducing, modulating, or eliminating, that results in the improvement of the cancer. "Treating" or "treatment" of cancer state includes: inhibiting the cancer, i.e., arresting the development of the cancer or its clinical symptoms; or relieving the cancer, i.e., causing temporary or permanent regression of the cancer or its clinical symptoms. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. Any of the compositions (e.g., pharmaceutical compositions) described herein can be used to treat an animal.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects. In certain embodiments of a method of treating cancer in a subject in need of treatment thereof comprising administering to the subject an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), the subject that is administered an effective amount is a mammal.

An "effective amount" is defined herein in relation to the treatment of cancers is an amount that will decrease, reduce, inhibit, or otherwise abrogate the growth of a cancer cell or tumor. The "effective amount" can vary depending the cancer and its severity and the age, weight, etc., of the mammal to be treated. "Therapeutically effective amount" means an amount effective to achieve a desired and/or beneficial effect (e.g., in relation to treating cancer). An effective amount or a therapeutically effective amount can be administered in one or more administrations. In some embodiments, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as measurement of tumor size.

It will be understood that the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), can include pharmaceutically acceptable salts, solvates, stereoisomers, and optical isomers thereof. It will further be understood that the compounds (e.g., Formula (I), Formula (II), Formula (III), Formula (IV), Formula (V), Formula (VI), Formula (VII), Formula (VIII), Formula (IX), Formula (X), 5MPN, or MPN-2) can include prodrugs of such compounds. In some embodiments, the compounds disclosed herein can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, derivatives of the compounds (e.g., ethers, esters, or amides) which have desirable retention and release characteristics, but which are hydrolyzed (e.g., easily hydrolyzed) by body pH, enzymes, or other suitable means, can be employed.

In some embodiments, the compounds of the invention having a chiral center and can exist in and be isolated in optically active and racemic forms. In other embodiments, compounds may exhibit polymorphism. Some embodiments of the present invention encompass any racemic, optically active, polymorphic, or stereoisomeric form, or mixtures thereof, of a compound described herein. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase. In other embodiments, compounds of the invention encompass the compounds disclosed herein and salts, optical isomers, geometric isomers, salts of isomers, and derivatives thereof.

"Pharmaceutically acceptable salt" of a compound means a salt that is pharmaceutically acceptable and that possesses the desired pharmacological activity of the parent compound. As used herein, "pharmaceutically acceptable salt" refers to modification(s) of the compounds (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) wherein such compounds are modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

It should be understood that all references to the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), or pharmaceutically acceptable salts thereof, include solvent addition forms (solvates) or crystal forms (polymorphs) as defined herein.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) of the present invention can be prepared as prodrugs, for example pharmaceutically acceptable prodrugs. The terms "pro-drug" and "prodrug"

are used interchangeably herein and refer to any compound which releases an active parent drug in vivo. Since prodrugs are known to enhance numerous desirable qualities of pharmaceuticals (e.g., solubility, bioavailability, manufacturing, etc.) The presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be delivered in prodrug form. Thus, the present invention is intended to cover prodrugs of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), methods of delivering the same and compositions containing the same. "Prodrugs" are intended to include any covalently bonded carriers that release an active parent drug of the present invention in vivo when such prodrug is administered to a subject.

In certain embodiments, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) are administered at a dosage effective for specifically inhibiting 6-phosphofructo-2-kinase/fructose-2,6-bisphophatase 4 (PFKFB4). In some embodiments, "specifically inhibiting" is defined as inhibiting PFKFB4 without inhibiting 6-phosphofructo-2-kinase/fructose-2,6,biphosphate 3 (PFKFB3), 6-phosphofructo-2-kinase/fructose-2,6-biphospatase 2 (PFKFB2), or 6-phosphofructo-2-kinase/fructose-2,6,biphosphate 1 (PFKFB1).

In some embodiments, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be delivered regionally to a particular affected region or regions of the subject's body. In some embodiments, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be administered systemically. For example, in some embodiments of a method treating cancer in a subject in need of treatment thereof, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) are administered orally. In accordance with the presently disclosed methods, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be administered orally as a solid or as a liquid. In other embodiments of treating cancer in a subject in need of treatment, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) is administered intravenously. In accordance with the presently disclosed methods, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be administered intravenously as a solution, suspension, or emulsion. Alternatively, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) also can be administered by inhalation, intravenously, or intramuscularly as a liposomal suspension.

In certain embodiments of a method of treating cancer in a subject in need of treatment thereof comprising administering to the subject an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), the subject that is administered an effective amount of said small molecule antagonist is substantially free of signs of toxicity. "Substantially free of signs of toxicity" includes unsafe deviations on complete blood counts, electrolytes, hepatic and renal function, body mass, and the unsafe deviations on the gross and histological appearance of the brain, heart, lungs, liver, kidneys, and spleen due to the administration of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) to the subject. In some instances, the pharmaceutical composition is non-toxic, does not cause side effects, or both. In some embodiments, there may be inherent side effects (e.g., it may harm the patient or may be toxic or harmful to some degree in some patients).

In some embodiments of a method of treating cancer in a subject in need of treatment thereof comprising administering to the subject an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), the method further comprises administering to the subject one or more additional therapeutic compounds. It will be appreciated that therapeutic benefits for the treatment of cancer can be realized by combining treatment with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) with one or more additional therapeutic compounds. The term "additional therapeutic compounds" includes anti-cancer agents or treatments. The choice of such combinations can sometimes depend on various factors including, but not limited to, the type of disease, the age and general health of the subject, the aggressiveness of disease progression, and the ability of the subject to tolerate the agents that comprise the combination. For example, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be combined with other agents and therapeutic regimens that are effective at reducing tumor size (e.g., radiation, surgery, chemotherapy, hormonal treatments, and or gene therapy).

Further, in some embodiments, it can be desirable to combine the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) with one or more agents that treat the side effects of a disease or the side effects of one of the additional therapeutic agents, e.g., providing the subject with an analgesic, or agents effective to stimulate the subject's own immune response (e.g., colony stimulating factor).

Thus, the term "additional therapeutic compounds" includes a variety of anti-cancer agents or treatments, such as chemical compounds that are also known as anti-neoplastic agents or chemotherapeutic agents. In some embodiments, the agents can be used in combination with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof). Such compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

In some embodiments, antibiotics used in the treatment of cancer and that can be combined with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) include dactinomycin, daunorubicin, doxorubicin, idarubicin, bleomycin sulfate, mytomycin, plicamycin, and streptozocin. In some embodiments, chemotherapeutic antimetabolites can also be combined with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) for the treatment of cancer, and include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

In some embodiments, chemotherapeutic protein synthesis inhibitors can also be combined with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) for the treatment of cancer. Such inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine.

In some embodiments, protein synthesis inhibitors can also be combined with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) for the treatment of cancer. Such inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Furthermore, in other embodiments, inhibitors of DNA synthesis can be combined with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) for the treatment of cancer. Such inhibitors include alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) to provide a suitable cancer treatment.

Thus, current chemotherapeutic agents that can, in other embodiments, be used in a combination treatment with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) include, but are not limited to, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chlorambucil, bisulfan, nitrosurea, dactinomycin, duanorubicin, doxorubicin, bleomycin, plicomycin, tamoxifen, taxol, transplatimun, vinblastin, and methotrexate, and the like.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide or any of those disclosed herein), radiation therapy, antiangiogenic therapy (e.g., bevacizumab), and hormone therapies, such as administration of LHRH agonists; antiestrogens, such as tamoxifen; high-dose progestogens; aromatase inhibitors; and/or adrenalectomy. Chemotherapy (e.g., any of those disclosed herein) can be used as a single-agent or as a combination with known or new therapies.

"Additional therapeutic compounds" can further involve immunotherapy directed at tumor antigen markers that are found on the surface of tumor cells. Treatment of a cancer with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can further be combined with a gene therapy based treatment, targeted towards oncogenes and/or cell cycle controlling genes, such as p53, p16, p21, Rb, APC, DCC, NF-1, NF-2, BRCA2, FHIT, WT-1, MEN-I, MEN-II, BRCA1, VHL, FCC, MCC, ras, myc, neu, raf, erb, src, fms, jun, trk, ret, gsp, hst, bcl, and abl, which are often mutated versions of their normal cellular counterparts in cancerous tissues.

In some embodiments of a method of treating cancer in a subject in need of treatment thereof comprising administering to the subject an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), one or more additional therapeutic compounds comprise one or more of a PFKFB3 inhibitor, a PFKFB2 inhibitor, and a PFKFB1 inhibitor. In certain embodiments, the one or more PFKFB3 inhibitor is PFK15.

The additional therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered can be varied.

In some embodiments, additional cancer treatments can be used in combination with administration of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof). For example, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be used as part of a treatment course further involving attempts to surgically remove part or all of a cancerous growth. For instance, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can be administered after surgical treatment of a subject to treat any remaining neoplastic or metastasized cells. Treatment with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can also precede surgery, in an effort to shrink the size of a tumor to reduce the amount of tissue to be excised, thereby making the surgery less invasive and traumatic. Furthermore, treatment with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) can include one or more treatment courses with a radiotherapeutic agent to induce DNA damage. Radiotherapeutic agents, include, for example, gamma irradiation, X-rays, UV-irradiation, microwaves, electronic emissions, radioisotopes, and the like. Therapy can be achieved by irradiating the localized tumor site with the above-described forms of radiation.

In other embodiments of the presently-disclosed subject matter, a pharmaceutical composition comprising an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) and at least one pharmaceutical excipient is provided. "Pharmaceutically acceptable excipient" can sometimes mean an excipient that is useful in preparing a pharmaceutical composition that is generally safe, non-toxic and neither biologically nor otherwise undesirable, and includes excipient that is acceptable for veterinary use as well as human pharmaceutical use. Thus, the term "pharmaceutical excipient" is used herein to describe any ingredient other than the compound(s) of the invention. Examples of pharmaceutical excipients include one or more substances which may act as diluents, flavoring agents, solubilisers, lubricants, suspending agents, binders, preservatives, wetting agents, tablet disintegrating agents, or an encapsulating material. In some embodiments, the choice of excipient can depend on factors such as the particular mode of administration, the effect of the excipient on solubility and stability, and the nature of the dosage form. A "pharmaceutical excipient" includes both one and more than one such excipient.

In certain embodiments of a pharmaceutical composition comprising an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) and at least one pharmaceutical excipient, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) is an amount that specifically inhibits PFKFB4. Thus, in embodiments of the pharmaceutical composition, the presently-disclosed small molecule antagonists of the kinase domain of PFKFB4 are specific inhibitors of the activity of PFKFB4. In some aspects, the specific inhibitors of PFKFB4 inhibits the activity of PFKFB4 by at least about 25%, 30%, 35%, 40%, 45%, 50%, 55%, 60%, 65%, 70%, 75%, 80%, 85%, 90%, 95% 99%, or any value or range in between, but does not inhibit the activity of PFKFB1, PFKFB2, PFKFB3 by more than about 20%, 15%, 10%, 5%, 2%, or 1%.

In some embodiments, the pharmaceutical composition comprising an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) and at least one pharmaceutical excipient described herein can be formulated with a pharmaceutically acceptable carrier for administration to a human or an animal. As such, the pharmaceutical compositions can be administered orally as a solid or as a liquid, or can be administered intramuscularly or intravenously as a solution, suspension, or emulsion. Alternatively, the pharmaceutical compositions can be administered by inhalation, intravenously, or intramuscularly as a liposomal suspension. In some embodiments, the pharmaceutical composition is formulated for oral administration. In other embodiments, the pharmaceutical composition is formulated for intravenous administration.

In some embodiments of a pharmaceutical composition comprising an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) and at least one pharmaceutical excipient, the pharmaceutical composition comprises one or more additional therapeutic agents, as defined above. In certain embodiments, the one or more additional therapeutic compounds comprise one or more of a PFKFB3 inhibitor, a PFKFB2 inhibitor, and a PFKFB1 inhibitor.

In other embodiments of the presently-disclosed subject matter, a method of inhibiting PFKFB4 in a cell comprising contacting the cell with an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) is provided. In certain embodiments, PFKFB4 is specifically inhibited by the presently-disclosed small molecule antagonists of the kinase domain of PFKFB4. Thus, in certain embodiments, the presently-disclosed small molecule antagonists of the kinase domain of PFKFB4 are specific inhibitors of the activity of PFKFB4. In some aspects, the specific inhibitors of PFKFB4 inhibits the activity of PFKFB4 by at least about 25%, 30%, 35%, 40%, 45%, 50%, 55%, 60%, 65%, 70%, 75%, 80%, 85%, 90%, 95% 99%, or any value or range in between, but does not inhibit the activity of PFKFB1, PFKFB2, PFKFB3 by more than about 20%, 15%, 10%, 5%, 2%, or 1%.

In some embodiments of a method of inhibiting PFKFB4 in a cell comprising contacting the cell with an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), the cell is a mammalian cell. In certain embodiments, the cell is a cancer cell. In other embodiments, the cell is derived from a cell line comprising H460, H1299, H441, H522, DAOY, D283, SKBR3, JURKAT, B16F10, A549, MDA-MB-231, LNCaP, HCT116, or LLC cell lines. In other embodiments, the cell is or is derived from a cell line of H460 (NSCLC), H1299 (NSCLC), H441 (NSCLC), H522 (NSCLC), DAOY and D283 (brain tumor), SKBR3 (breast), JURKAT (leukemia/hematological malignancy), B16F10 (mouse melanoma), A549 (NSCLC), MDA-MB-231 (breast cancer), LNCaP (prostatic cancer), HCT116 (colon cancer), or LLC (Lewis lung carcinoma) cell lines (e.g., obtained from ATCC).

In other embodiments of the presently-disclosed subject matter, a method of inhibiting PFKFB4 in a subject in need thereof comprising administering to the subject an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) is provided.

In certain embodiments, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) is administered at a dosage effective for specifically inhibiting PFKFB4. In some aspects, the specific inhibitors of PFKFB4 inhibits the activity of PFKFB4 by at least about 25%, 30%, 35%, 40%, 45%, 50%, 55%, 60%, 65%, 70%, 75%, 80%, 85%, 90%, 95% 99%, or any value or range in between, but does not inhibit the activity of PFKFB1, PFKFB2, PFKFB3 by more than about 20%, 15%, 10%, 5%, 2%, or 1%.

In some embodiments of a method of inhibiting PFKFB4 in a subject in need thereof comprising administering to the subject an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), with said small molecule antagonists administered orally. In other embodiments, the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) are administered intravenously.

In some embodiments of a method of inhibiting PFKFB4 in a subject comprising administering to the subject an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), the subject remains substantially free of signs of toxicity.

In other embodiments of the presently-disclosed subject matter, a method of reducing proliferative capacity of a cell comprising contacting the cell with an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) is provided. In certain embodiments, the cell is contacted with the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) at a dosage effective for specifically inhibiting PFKFB4. In some aspects, the specific inhibitors of PFKFB4 inhibits the activity of PFKFB4 by at least about 25%, 30%, 35%, 40%, 45%, 50%, 55%, 60%, 65%, 70%, 75%, 80%, 85%, 90%, 95% 99%, or any value or range in between, but does not inhibit the activity of PFKFB1, PFKFB2, PFKFB3 by more than about 20%, 15%, 10%, 5%, 2%, or 1%.

In some embodiments of a method of reducing proliferative capacity of a cell comprising contacting the cell with an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof), the cell is a mammalian cell. In certain embodiments, the cell is a cancer cell. In other embodiments, the cell is derived from a cell line comprising H460, H1299, H441, H522, DAOY, D283, SKBR3, JURKAT, B16F10, A549, MDA-MB-231, LNCaP, HCT116, or LLC cell lines. In other embodiments, the cell is or is derived from a cell line of H460 (NSCLC), H1299 (NSCLC), H441 (NSCLC), H522 (NSCLC), DAOY and D283 (brain tumor), SKBR3 (breast), JURKAT (leukemia/hematological malignancy), B16F10 (mouse melanoma), A549 (NSCLC), MDA-MB-231 (breast cancer), LNCaP (prostatic cancer), HCT116 (colon cancer), or LLC (Lewis lung carcinoma) cell lines (e.g., obtained from ATCC).

In other embodiments of the presently-disclosed subject matter, a method of reducing fructose-2,6-bisphosphate (F2,6BP) in a cell comprising contacting the cell with an effective amount of the presently-disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) is provided. In some embodiments, the cell is a mammalian cell. In certain embodiments, the cell is a cancer cell, such as, but not limited to lung, breast, colon, ovarian, brain, liver, pancreas, prostate, melanoma, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

EXAMPLES

The presently-disclosed subject matter is further illustrated by the following specific but non-limiting examples. The following examples may include compilations of data that are representative of data gathered at various times during the course of development and experimentation related to the present invention.

Example 1

Material and Methods

Some related methods and related information can be found in (a) CHESNEY et al., "Fructose-2,6-bisphosphate synthesis by 6-phosphofructo-2-kinase/fructose-2,6-bisphosphatase 4 (PFKFB4) is required for the glycolytic response to hypoxia and tumor growth" Oncotarget (2014) Vol. 5, No. 16, pp. 6670-6686 (which is herein incorporated by reference in its entirety) and (b) CHESNEY et al., "Targeting the sugar metabolism of tumors with a first-in-class 6-phosphofructo-2-kinase (PFKFB4) inhibitor" Oncotarget (2015) Vol. 6, No. 20, pp. 18001-18011 (which is herein incorporated by reference in its entirety). Some related methods and related information can be found in WO 2016/172499 A1 dated Oct. 27, 2016 entitled "Selective PFKFB4 Inhibitors for The Treatment of Cancer" to University of Louisville Research Foundation, Inc. (which is herein incorporated by reference in its entirety).

Cell Lines and Cell Culture:

H460, H1299, H441, H522 and A549 non-small cell lung cancer (NSCLC), MDA-MB-231 (breast), LNCaP (prostatic) and HCT116 (colon) adenocarcinoma and Lewis lung carcinoma (LLC) cell lines were obtained from ATCC and used within 6 months of acquisition. PFKFB4$^{-/-}$ ear pinna fibroblasts isolated from TamCre/loxP/PFKFB4$^{-/-}$ mice were immortalized as described previously (Chesney J et al. Fructose-2,6-bisphosphate synthesis by 6-phosphofructo-2-kinase/fructose-2,6-bisphosphatase 4 (PFKFB4) is required for the glycolytic response to hypoxia and tumor growth. Oncotarget 2014 Aug. 30; 5(16):6670-86). Normal bronchial epithelial cells (NHBE) were obtained from Lonza and NHBE cells expressing telomerase, SV40 large T antigen and activated Ras (hT/LT/Ras) were a gift from Dr. B. J. Rollins, Dana Farber Cancer Institute. All cell lines were tested and found negative for *mycoplasma* (PCR *Mycoplasma* Detection Kit, ABM). Cell lines were grown in DMEM (A549, LNCaP, MDA-MB-231, LLC and PFKFB4$^{-/-}$), RPMI 1640 (H460, H1299, H441, H522) and McCoy's 5A media (HCT116) (all from Invitrogen) containing 10% fetal calf serum (Hyclone). NHBE and hT/LT/Ras cells were grown in BEGM containing SingleQuots (Lonza). All lines were cultured at 37° C. in 5% $CO_2$. In certain experiments, 4-hydroxytamoxifen (4HT, Sigma-Aldrich) was added to PFKFB4$^{-/-}$ fibroblasts at indicated concentrations.

Cell Viability:

Cells were incubated in 20% trypan blue (Sigma) for 5 minutes. Cells excluding trypan blue were counted using a standard hemocytometer (Hausser Scientific) to determine total numbers of viable cells. Data are expressed as mean±SD of three experiments.

PFKFB4 Modeling and Compound Screen:

The PFKFB4 homology model used the rat testes PFKFB4 isozyme X-ray structure (PDB code 1BIF) as a structural template. An alignment was generated using Clustal W (CHENNA et al., "Multiple sequence alignment with the Clustal series of programs" Nucleic Acids Res (2003) Vol. 31, No. 13, pp. 3497-500). Four homology models were generated using Modeller (SALI et al., "Comparative protein modeling by satisfaction of spatial restraints" J Mol Biol (1993) Vol. 234, No. 3, pp. 779-815), and the structure that best reproduced the PFKFB4 binding site selected for further use. The residues associated with ligand binding and protein activity for PFKFB4 were correlated to equivalent residue numbers in the consensus structure. The catalytic site residues were selected to produce a residue-based protocol for Surflex 1.33 (JAIN "Surflex: fully automatic flexible molecular docking using a molecular similarity-based search engine" J Med Chem (2003) Vol. 46, No. 4, pp. 499-511) for the virtual screening run using the 2007 ZINC-drug-like library containing 3,381,225 compounds. The highest-scoring 100 molecules were identified for purchase. All computational work and virtual screening was done in the Brown Cancer Center Molecular Modeling Facility. The top 30 commercially available compounds were purchased and examined for inhibitory effects on H460 cell proliferation and recombinant PFKFB4 activity.

Transfections:

For siRNA experiments, cells growing in 6-well plates were transfected with control (Stealth Negative Control Medium GC, Invitrogen) or PFKFB4 siRNA (siFB4, HSS107863, Invitrogen) using Lipofectamine RNAiMax (Invitrogen) and harvested as indicated. For overexpression experiments, cells were transfected with pCMV-XL4 (vector) or pCMV-XL4 containing full-length PFKFB4 (Origene) using Lipofectamine 2000 (Invitrogen) and harvested as indicated.

Protein Extraction and Western Blotting:

Protein extraction and blotting were conducted as previously described. Membranes were probed with antibodies to PFKFB4 (Abcam) or β-actin (Sigma) followed by HRP-conjugated goat anti-rabbit or anti-mouse secondary antibodies respectively (Pierce). Data shown are representative of three experiments.

Kinase Assays:

The fructose-6-phosphate kinase activity of human recombinant PFKFB4 in the presence of DMSO±indicated 5MPN concentrations was assayed as previously described. The activity of 5MPN against 97 kinases was examined using a commercially available active-site dependent competition binding assay core service (KINOMEscanEDGE) that quantifies the capacity of test agents to compete with an immobilized, active-site directed ligand using a DNA-tagged kinase and immobilized ligand and compound. For example, enzyme inhibition was studied using an ADP-Glo assay. The effect of MPN-2 on the activity of recombinant human PFKFB4 enzyme was examined in an ADP-Glo assay (Promega), which measures ADP formed from a kinase reaction. ADP is converted into ATP, which is converted into light by a luciferase. PFKFB4 protein was exposed to MPN-2 at indicated concentrations in the presence of ATP and fructose-6-phosphate and following manufacturer's instructions, ADP-Glo and kinase detections reagents were added. The data are shown as the decrease in luminescence caused by MPN-2 relative to DMSO.

F2,6BP Measurements:

Cells or tissues were prepared as previously described and F2,6BP content measured using a coupled enzyme reaction following a modification of the method of Van Schaftingen et al (VAN SCHAFTINGEN E et al. "A kinetic study of pyrophosphate:fructose-6-phosphate phosphotransferase from potato tubers. Application to a microassay of fructose 2,6-bisphosphate" Eur J Biochem (1982) Vol. 129, No. 1, pp. 191-195) and normalized to total cellular protein measured by the bicinchoninic acid assay (BCA, Thermo Scientific). For example, H460 cells were exposed to the indicated concentrations of MPN-2. In order to measure F2,6BP, cells were harvested, washed with PBS, lysed in NaOH/Tris acetate by heating at 80° C. and lysates neutralized to pH 7.2. F2,6BP content was measured using a coupled enzyme reaction following a modified method of Van Schaftingen et al (VAN SCHAFTINGEN E et al. "A kinetic study of pyrophosphate:fructose-6-phosphate phosphotransferase from potato tubers. Application to a microassay of fructose 2,6-bisphosphate" Eur J Biochem (1982) Vol. 129, No. 1, pp. 191-195). The F2,6BP concentration was normalized to total cellular protein measured by the bicinchoninic acid assay (BCA, Thermo Scientific). All data are expressed as the mean±SD of three experiments. Statistical significance was assessed by the two-sample t test (independent variable).

Glycolysis Assay:

H460 cells were exposed to the indicated concentrations of MPN-2 and glycolysis production was examined. Cells growing in 6-well plates were incubated in 500 µl of complete medium containing 1 µCi of 5-[$^3$H]glucose per well for 60 min in 5% $CO_2$ at 37° C. Media was collected, $^3H_2O$ formed via glycolysis from the 5-[$^3$H]glucose measured and counts normalized as previously described. For example, the medium was then collected and centrifuged to pellet any suspended cells. To separate the $^3H_2O$ formed via glycolysis from the 5-[$^3$H]glucose added to the medium, an evaporation technique in a sealed system was utilized. Briefly, 150 µl aliquots of medium were added to open tubes that were placed upright inside scintillation vials containing 1 ml of $H_2O$. The scintillation vials were sealed, and the $^3H_2O$ produced by glycolysis through enolase and released to the medium was allowed to equilibrate with the $H_2O$ in the outer vial for 48 h at 37° C. The amounts of $^3H_2O$ that had diffused into the surrounding $H_2O$ was measured on a Tri-Carb 2910 liquid scintillation analyzer (Perkin Elmer) and compared with $^3H_2O$ and 5-[$^3$H]glucose standards. Protein concentration was determined using the BCA assay and counts were normalized to protein concentration. All data are expressed as the mean±SD of three experiments. Statistical significance was assessed by the two-sample t test (independent variable).

ATP Measurements:

H460 cells were exposed to the indicated concentrations of MPN-2 and ATP production was examined. Cells were lysed and intracellular ATP determined as described previously. For example, cells were washed (while still adherent) with cold PBS 1×, lysed with Passive Lysis Buffer (1×; Molecular Probes, Invitrogen) added directly to the plates, and immediately harvested by scraping. The lysates were flash frozen (to −80° C.) and thawed (to 37° C.) once to accomplish complete lysis and then centrifuged (at 4° C.) for 30 seconds to clear the lysates. Intracellular ATP levels were determined using a bioluminescence assay (Molecular Probes), utilizing recombinant firefly luciferase and its substrate, D-luciferin. The luminescence was read in a TD-20/20 luminometer (Turner Designs) at 560 nm. The ATP values were calculated using an ATP standard curve. The protein concentrations of the lysates were estimated using the BCA assay (Pierce Biotechnology) and ATP was expressed as pmol/µg protein. All data are expressed as the mean±SD of three experiments. Statistical significance was assessed by the two-sample t test (independent variable).

Proliferation Assays:

H460 non-small cell lung cancer cells were plated in 24 well plates and exposed to increasing concentrations of the indicated inhibitors of Formula IV (FBR1-02 corresponds to

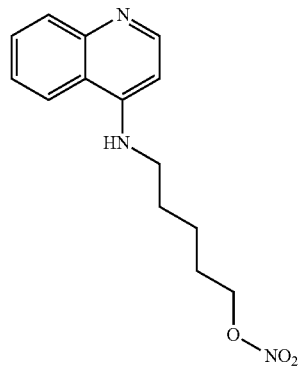 [SMILES: O=[N+]([O-])OCCCCCNc1ccnc2ccccc12]

and FBR1-12 corresponds to

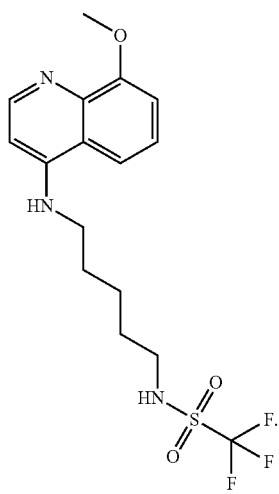 [SMILES: COc1cccc2c(NCCCCCNS(=O)(=O)C(F)(F)F)ccnc12]

DMSO was used as vehicle. After 24, 48 and 72 hours of exposure, cells were detached and viable cells were counted by Trypan blue exclusion (representative counts at 48 hours shown).

Flow Cytometry:

To measure apoptosis, cells were stained with annexin V and propidium iodide and examined as previously described. For example, H460 cells were exposed to increasing concentrations of the PFKFB4 inhibitor (MPN-2), the PFKFB3 inhibitor PFK15 (Tocris) or both and viable cells were counted at 24, 48 and 72 hours. DMSO used as vehicle. For cell cycle experiments, cells were detached, washed with cold PBS and fixed in 70% ethanol (4° C., 30 minutes). The cells then were pelleted by centrifugation, resuspended in PBS containing PI and RNase A, incubated at 37° C. in the dark for 30 minutes and analyzed by flow cytometry (BD FACSCalibur). Data were analyzed using FlowJo software (TREE STAR Inc.). Results were calculated as the mean±SD of three experiments. The effects (Fa values) of the series of concentrations of MPN-2 and PFK-15 were examined individually and in combination at a constant ratio of 1:1. From these data, the CI values at various Fa levels were calculated (using the CompuSyn program and the CI algorithm, from Chou and Martin) and are also represented as a Combination Index plot and an isobologram for the combination of MPN-2 and PFK15. The CI values are <1 indicating that the combination of MPN-2 and PFK15 is synergistic (also seen in both plots by location of the data points below the lines that indicate additive effects).

In Vivo Studies.

The pharmacokinetic profile was determined in female C57BL/6 mice following IV and oral administration of 5MPN. Using only female mice lowered the animal numbers required for meaningful results without issues of potential gender differences in exposure. Eight time points (n=3/time point) were used to determine PK parameters calculated using WinNonLin v5.0. Plasma samples were extracted using acetonitrile and analyzed by LC/MS-MS using a PhenomexSynergi Polar-RP 4 micron 50×2.0 mm column eluted with a biphasic mobile phase (0.5% formic acid in acetonitrile and water).

For xenograft studies, exponentially growing LLC or H460 cells were detached, washed and resuspended in PBS. Female C57BL/6 mice (Jackson Labs) were injected with LLC cells (n=10/group, s.c., 1×10$^6$ cells) and female BALB/c athymic mice (Jackson Labs) with H460 cells (n=10/group, s.c, 5×10$^6$ cells). Tumor masses were determined in a blinded fashion with Vernier calipers using the formula: mass (mg)=(width, mm)$^2$×(length, mm)/2 as previously described. When tumor masses were 150-200 mg, mice were randomized to daily intraperitoneal DMSO or 5MPN at the indicated dose in 50 µL DMSO. Tumor measurements and body weights were followed daily. All data are expressed as the mean±SD of two experiments. Statistical significance was assessed by the two-sample t test (independent variable).

At the end of the experiment, animals were euthanized, tumors removed and sections fixed in 10% formaldehyde for immunohistochemistry or snap-frozen in liquid nitrogen for analyses. Subsets of tumor-bearing mice (n=3) were injected i.p. with 2-[$^{18}$F]-fluoro-2-deoxyglucose (FDG, 150 µCi, 100 µl) and imaged by micro-positron emission tomography as previously described. Regions of interest in the tumors and cerebellum were quantified in quadruplicate and expressed as the mean±SD of the tumor:cerebellar FDG uptake ratio. Animal experiments were approved by the University of Louisville Institutional Animal Care and Use Committee.

Immunohistochemistry:

Formalin-fixed, paraffin-embedded tissue sections were processed as previously described then incubated with anti-Ki-67 primary antibody (Abcam) overnight, followed by HRP-linked goat anti-rabbit secondary antibody (1:300, Pierce). Sections were developed with 3,3'-diaminobenzidine tetrahydrochloride, counterstained, scanned and analyzed with the positive pixel count algorithm as previously described. Data are depicted as % positive pixels/total pixels±SD.

Example 2

Small Molecule Antagonists of PFKFB4

Figure 1:
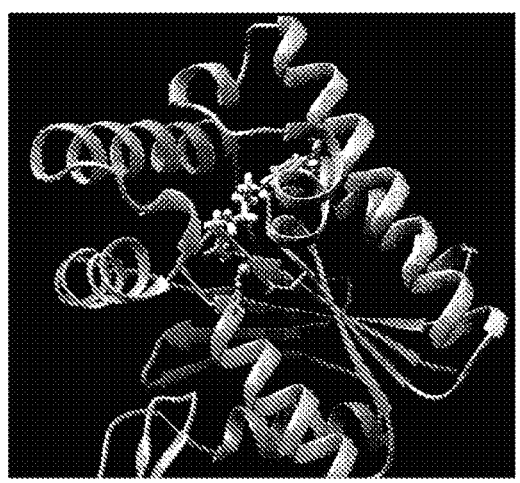
FIG. 1. Compound 5MPN inhibits recombinant PFKFB4 enzyme activity. Panel (A) shows a schematic representation of the 5MPN molecule docked in the crystal structure of rat testes PFKFB4. 5MPN is shown in thicker stick representation than the surrounding protein residues. Panel (B) shows the molecular structure of 5MPN (MW, 305.3 Da). Panels (C) and (D) show Michaelis-Menten and Lineweaver-Burk double reciprocal plots, respectively, examining PFKFB4 enzyme activity as a function of F6P concentration (0-2000 µmol/L). In vitro kinase assays using purified recombinant human PFKFB4 were performed as described in the presence or absence of 0, 0.1, 1 or 10 µM 5MPN. Data shown are representative of three independent experiments.
Figure 1:
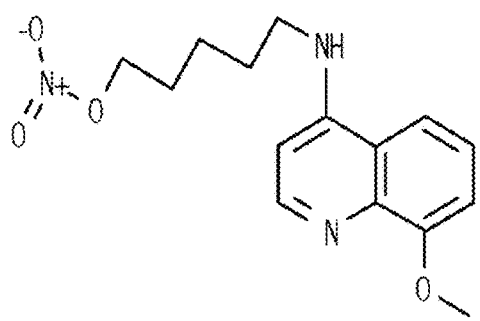
Figure 1:
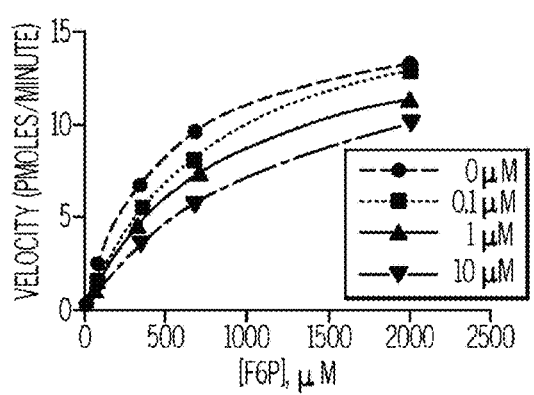
Figure 1:
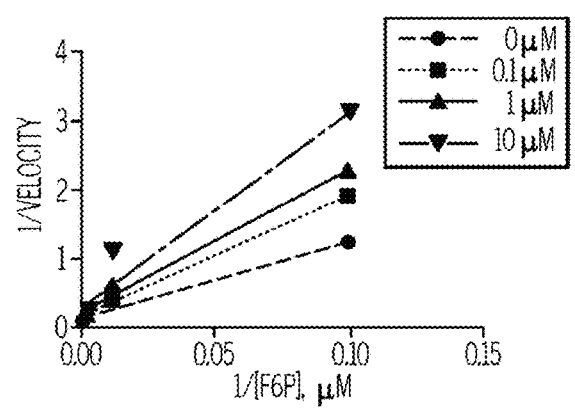

Results:

We utilized the X-ray structure of the *Rattus norvegicus* testes PFKFB4 (HASEMANN et al. "The crystal structure of the bifunctional enzyme 6-phosphofructo-2-kinase/fructose-2,6-bisphosphatase reveals distinct domain homologies" Structure (1996) Vol. 4, No. 9, pp. 1017-1029.) to conduct an in silico screen of >18 million small molecules to identify potential compounds that may interact with the fructose 6-phosphate (F6P) binding domain of PFKFB4. Over one hundred compounds were identified, scored, ranked, and analyzed based on their association potential with the active site within PFKFB4. We physically tested the 30 best-score compounds for their ability to inhibit the kinase activity of recombinant PFKFB4. For example, 5-[(8-methoxyquinolin-4-yl)amino]pentyl nitrate (termed 5MPN; FIG. 1A and FIG. 1B), inhibited PFKFB4 activity (FIG. 1C). Based on Lineweaver-Burk analyses, this compound appears to be a competitive inhibitor of the F6P binding site (FIG. 1D). This compound did not inhibit PFK-1 or PFKFB3 which share the identical substrate and are co-expressed with PFKFB4 in multiple cell lines and required for glucose metabolism (no inhibition of kinase activity with 10 µM). Additionally, a panel of 97 protein kinases was not inhibited by 10 µM of 5MPN providing further support for the selectivity of this compound for PFKFB4 (KINOMEscan, data not shown).

Example 3

Figure 2:
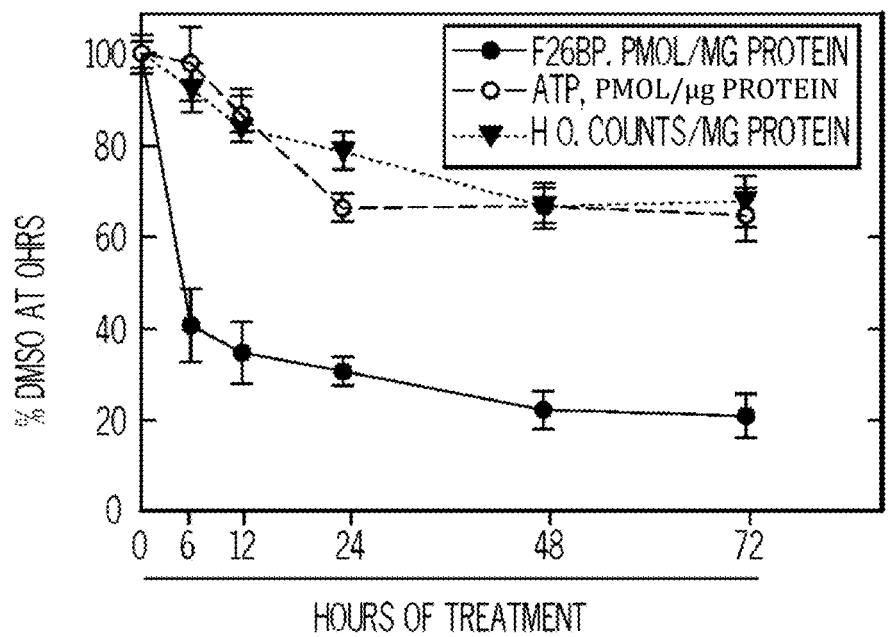
FIG. 2. 5MPN causes decreased proliferation of cancer cells preceded by a reduction in intracellular F2,6BP concentration, glycolysis and ATP. Panel (A) shows the results of H460 NSCLC cells treated with DMSO±10 µM 5MPN. The effects on F2,6BP production, glycolysis and ATP were measured after 6-72 hours. Panel (B) shows the proliferation of H460 cells exposed to DMSO±5MPN after 24-72 hours. Panel (C) shows the cell growth of NHBE cells and indicated transformed cell lines that were exposed to DMSO±5MPN. Viable cells counted at 48 hours. Panel (D) shows cell growth of NHBE and hT/LT/Ras cells treated with DMSO±5MPN. Live cells were counted at 48 hours. (*p value<0.01 hT/LT/Ras vs. NHBE). Panel (E) shows PFKFB4 expression of H460 cells transfected with empty pCMV-XL4 (Vec) or pCMV-XL4 containing full-length PFKFB4 (FB4) for 24 hours that were treated with DMSO±10 µM 5MPN. 24 hours after treatment with DMSO±10 µM 5MPN, PFKFB4 expression was examined by Western blot and viable cells were counted. (*p value<0.01 Vec vs. FB4 exposed to 5MPN). Panel (F) shows large T antigen-immortalized, tamoxifen (4HT)-inducible PFKFB4$^{-/-}$ lung fibroblasts that were exposed to vehicle (ethanol)±10 µM 4HT for 24 hours and then treated with DMSO±10 µM 5MPN. Cell counts and PFKFB4 protein expression were examined 24 hours later. (*p value<0.01 vehicle vs.+4HT, exposed to 5MPN). Data are expressed as the mean±SD of three experiments.
Figure 2:
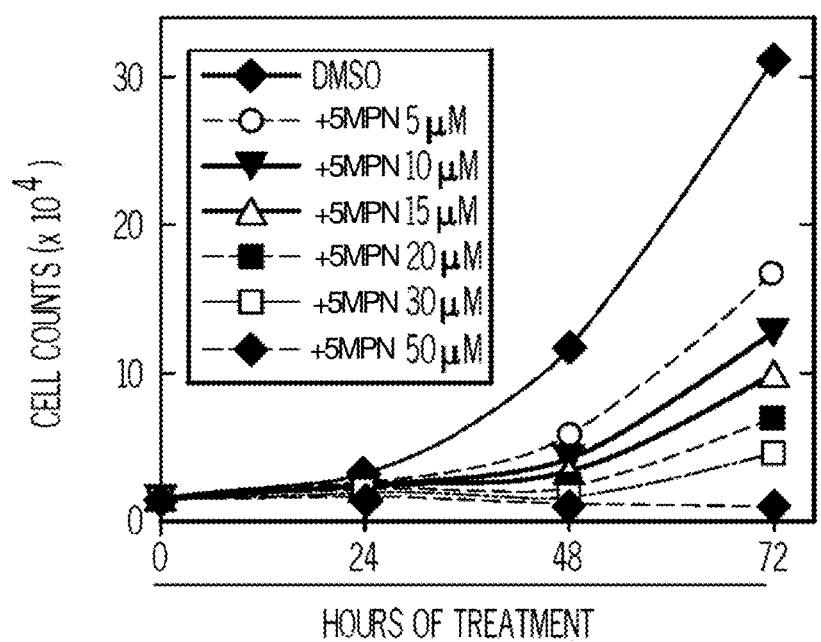
Figure 2:
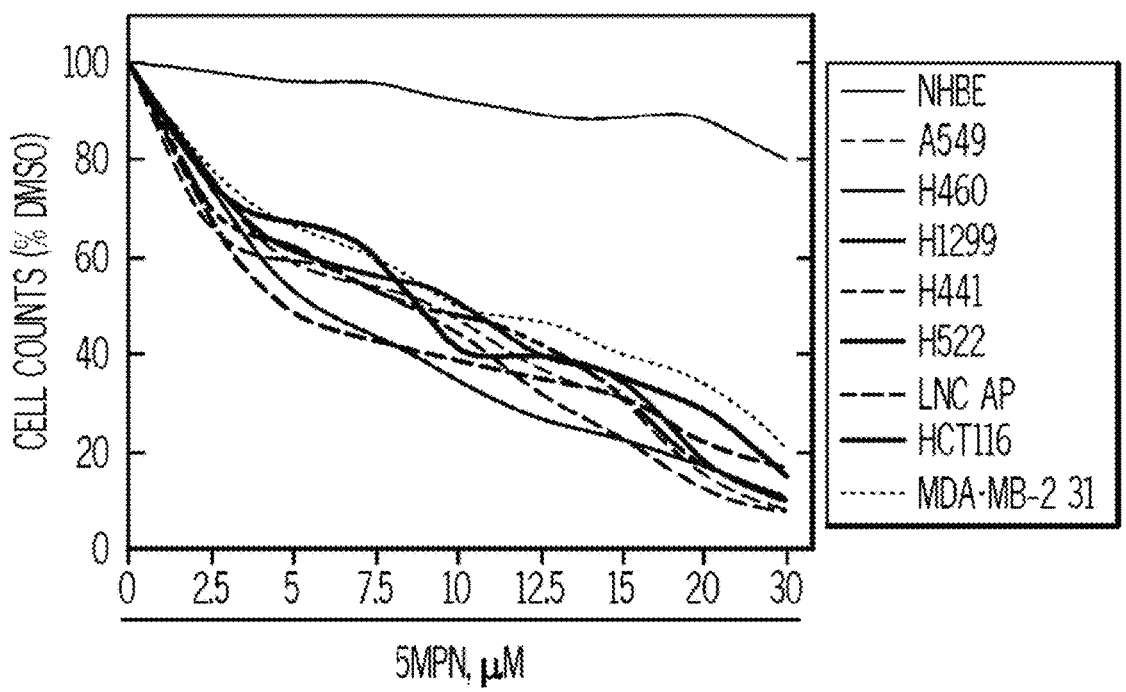
Figure 2:
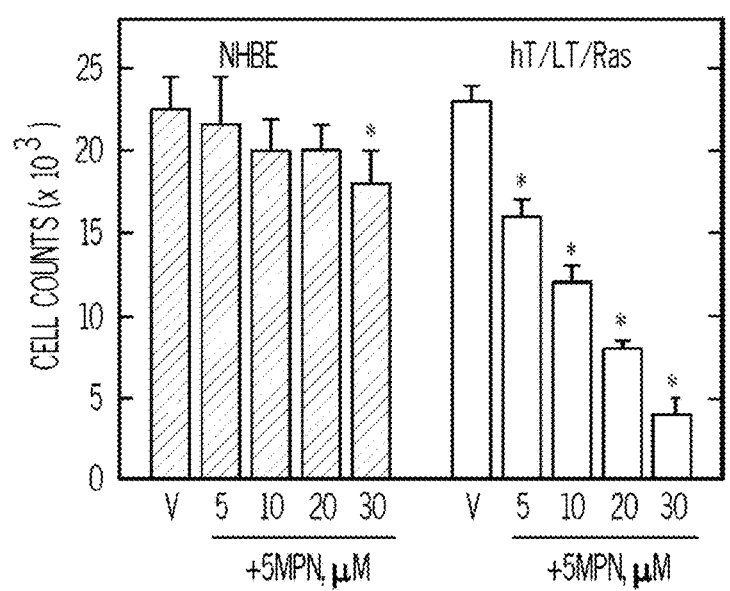
Figure 2:
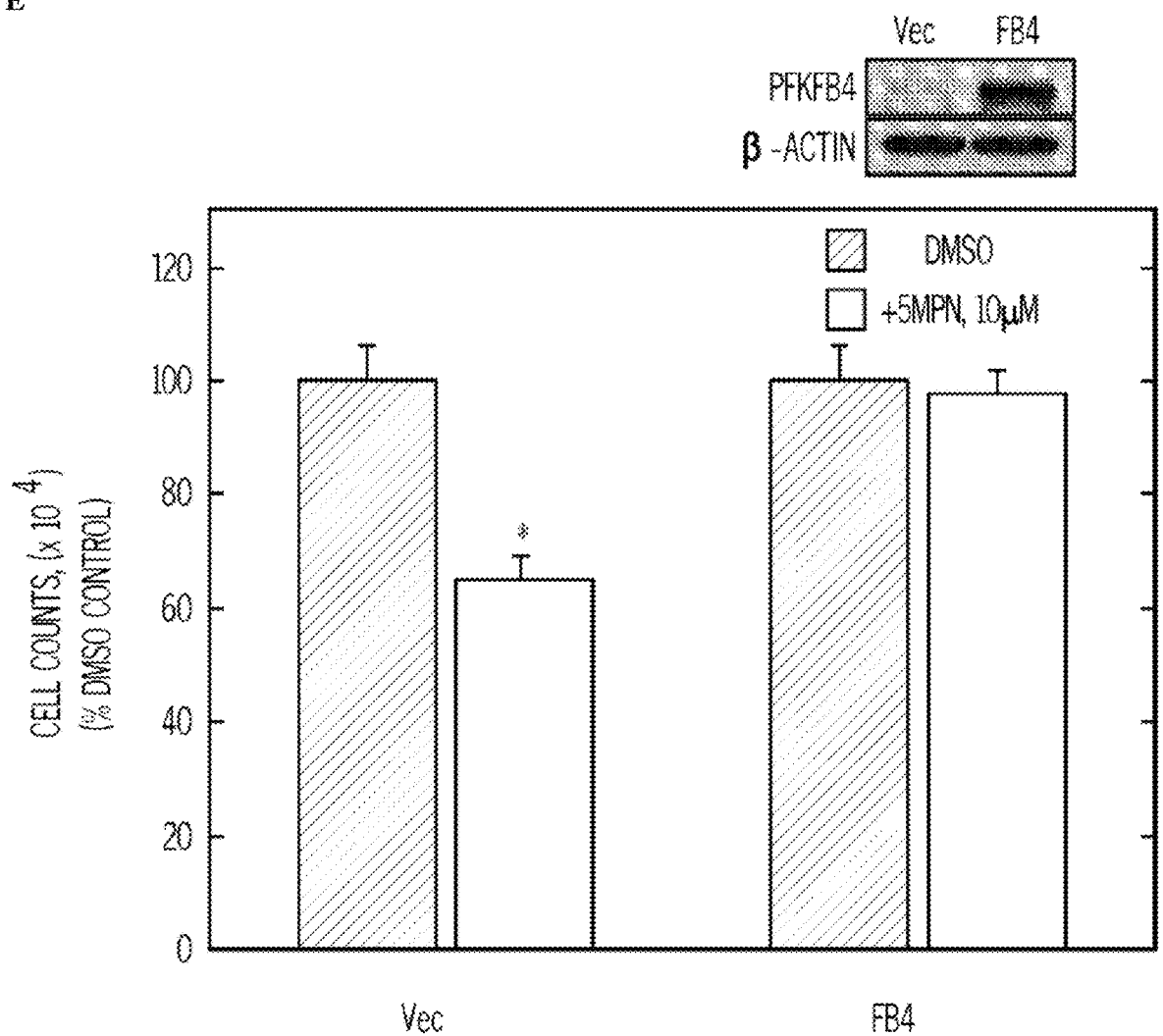
Figure 2:
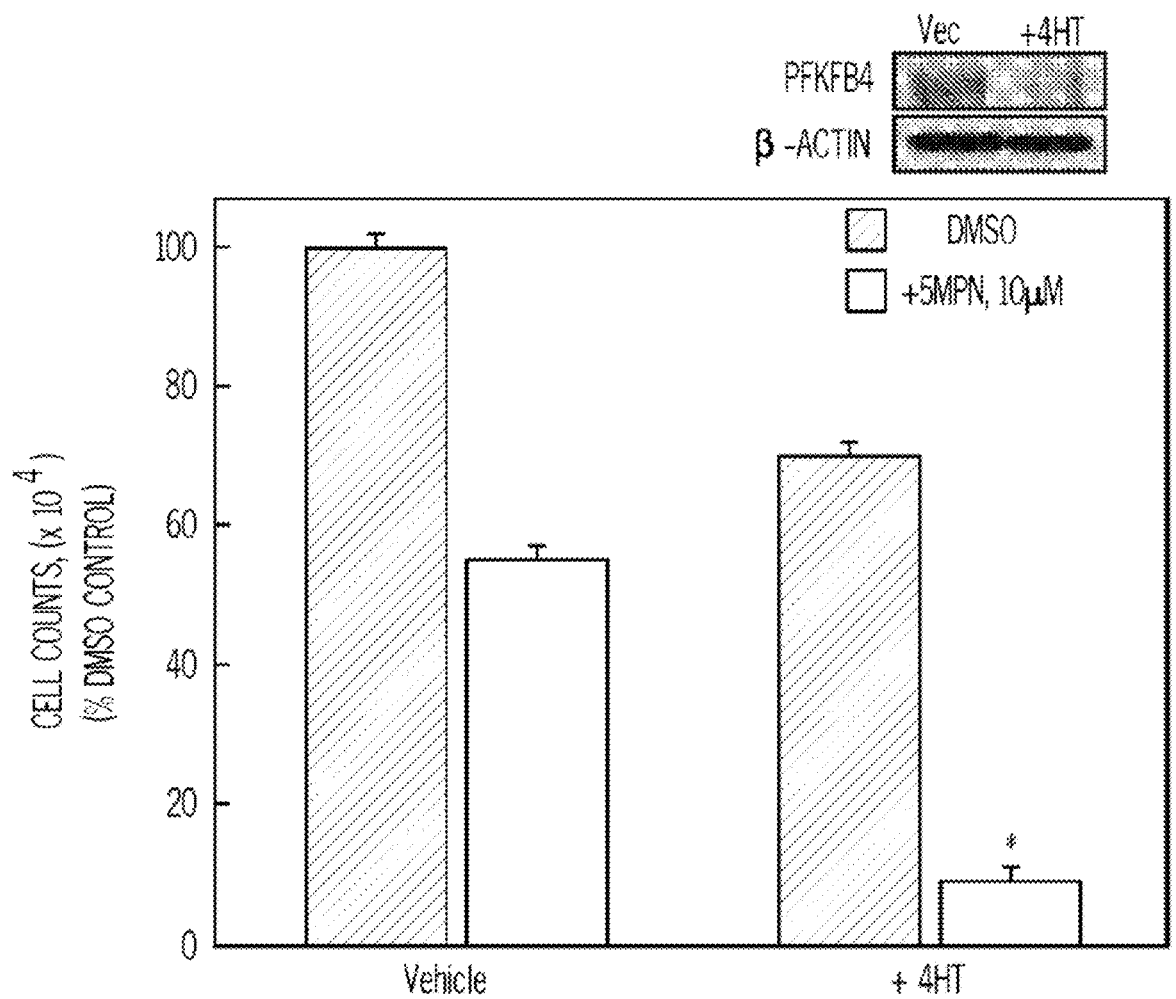

Pharmacological Inhibition of PFKFB4 by 5MPN is Selectively Cytostatic to Transformed Cells Results: H460 cells are lung adenocarcinoma cells that harbor several common oncogenic mutations (CDKN2A$^{del457}$, KRAS$^{Q61H}$, PIK3CA$^{E545K}$, STK11$^{Q37X}$) and are sensitive to inhibition of PFKFB4 using siRNA molecules. We examined the anti-metabolic effects of 5MPN on H460 cells and found that this agent reduced the intracellular concentration of F2,6BP, glycolysis and ATP (FIG. 2A) which in turn resulted in a reduction in cell proliferation (FIG. 2B). We also examined the effect of 5MPN on the proliferation of non-small cell lung cancer (H460, H1299, H441, H522 and A549), breast adenocarcinoma (MDA-MB-231), prostatic adenocarcinoma (LNCaP) and colon adenocarcinoma (HCT116) cell lines and observed a dose-dependent reduction in growth over 48 hours (FIG. 2C). Given that PFKFB4 has been found to be expressed by normal lung epithelia, we next examined the relative effects of 5MPN on normal human bronchial epithelial (NHBE) cells versus NHBE cells that had been sequentially immortalized with telomerase and large T antigen and transformed with H-Ras$^{V12}$ (hT/LT/Ras cells). We found that the NHBE cells were virtually unaffected whereas hT/LT/Ras cell growth was suppressed similar to other transformed cells (FIG. 2D). In order to interrogate the requirement of PFKFB4 inhibition for the observed suppression of proliferation (on-target effects), we next examined the effects of genetic modulation of PFKFB4 on the anti-proliferative effects of 5MPN. We found that whereas overexpression of PFKFB4 protected H460 cells from 5MPN, genomic deletion of Pfkfb4 sensitized cells to 5MPN (FIG. 2E and FIG. 2F), thus supporting the concept that inhibition of PFKFB4 by 5MPN is causing the observed reduction in H460 cell proliferation. Taken together, these data indicate that 5MPN is a potent inhibitor of PFKFB4 that selectively suppresses the proliferation of transformed cells.

Example 4

Figure 3:
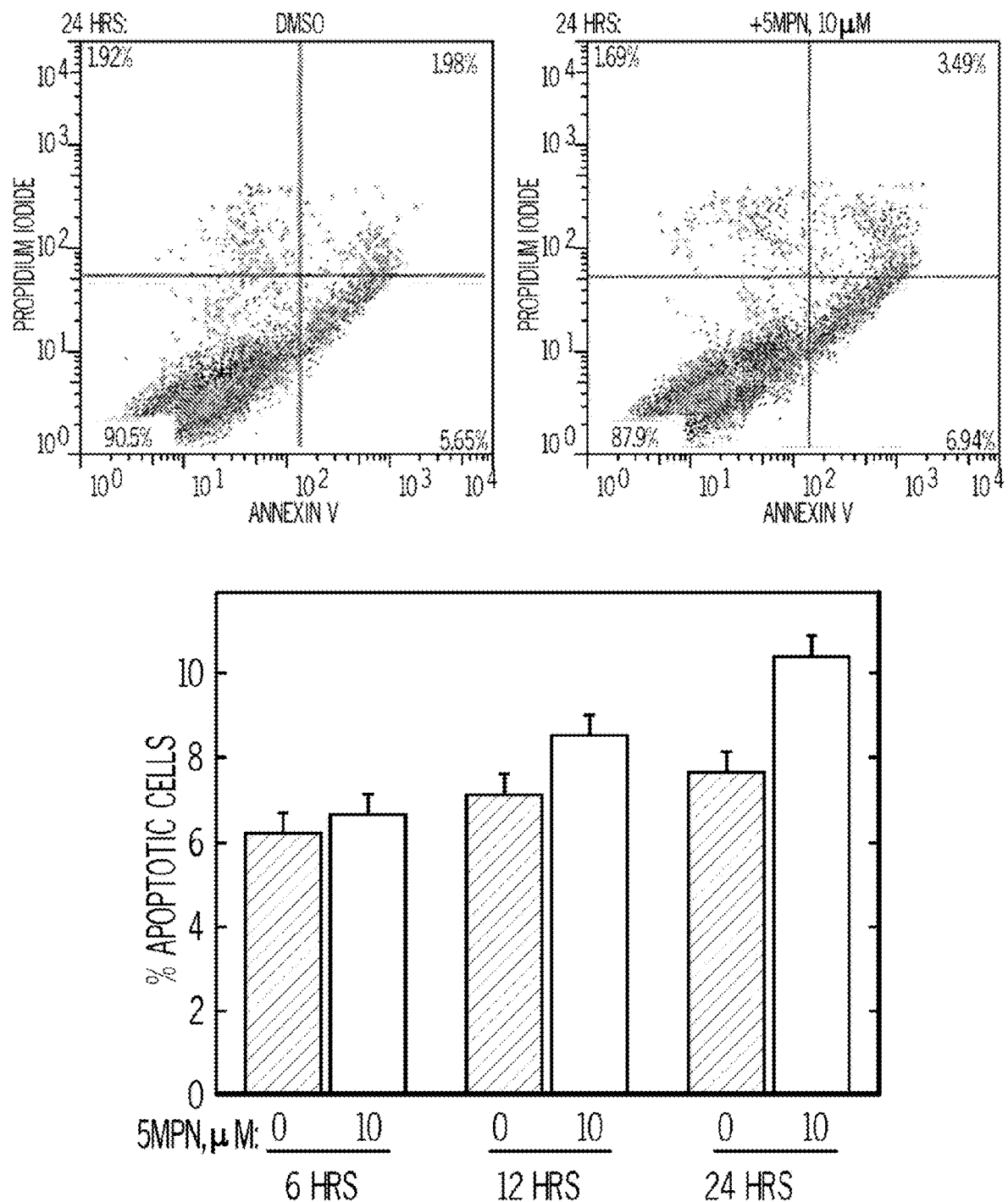
FIG. 3. 5MPN induces cell cycle arrest at the G1 phase. Panel (A) shows H460 cells treated with DMSO±10 µM 5MPN, while Panel (B) shows H460 cells treated transfected with nonsense (siCtrl) or PFKFB4 siRNA (siFB4). Cells were analyzed for induction of apoptosis by flow cytometry. Decrease in PFKFB4 protein expression by siFB4 was confirmed by Western blot. PI$^+$+PI/Ann V$^+$ cells shown as % apoptotic cells. Panel (C) shows H460 cells treated with DMSO±10 µM 5MPN and the distribution of cells in G1, S and G2 phases of the cell cycle. Panel (D) shows H460 cells transfected with siCtrl or siFB4 and the distribution of cells in phases of the cell cycle. H460 cells were transfected with empty pCMV-XL4 (Vec) or pCMV-XL4 containing PFKFB4 (FB4) for 24 hours then treated with DMSO±10 µM 5MPN for 24 hours. Panel (E) shows the H460 cells transfected with empty pCMV-XL4 (Vec) or pCMV-XL4 containing PFKFB4 (FB4) protein expression and F2,6BP concentration. H460 cells were transfected with empty pCMV-XL4 (Vec) or pCMV-XL4 containing PFKFB4 (FB4) for 24 hours then treated with DMSO±10 µM 5MPN for 24 hours. (*p value<0.01 Vec vs. FB4 exposed to 5MPN.) Panel (F) shows the H460 cells transfected with empty pCMV-XL4 (Vec) or pCMV-XL4 containing PFKFB4 (FB4) and the distribution of cells in G1, S and G2 phases of the cell cycle. Data shown are representative of three independent experiments and are expressed as the mean±SD of three experiments. *p value<0.01 compared to control.
Figure 3:
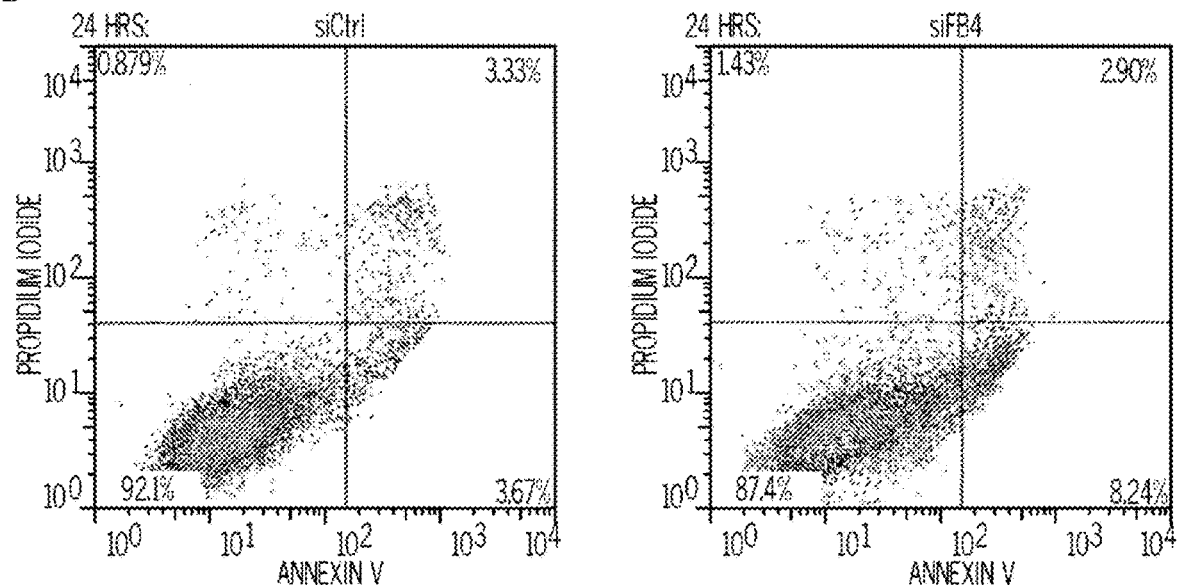
Figure 3:
Figure 3:
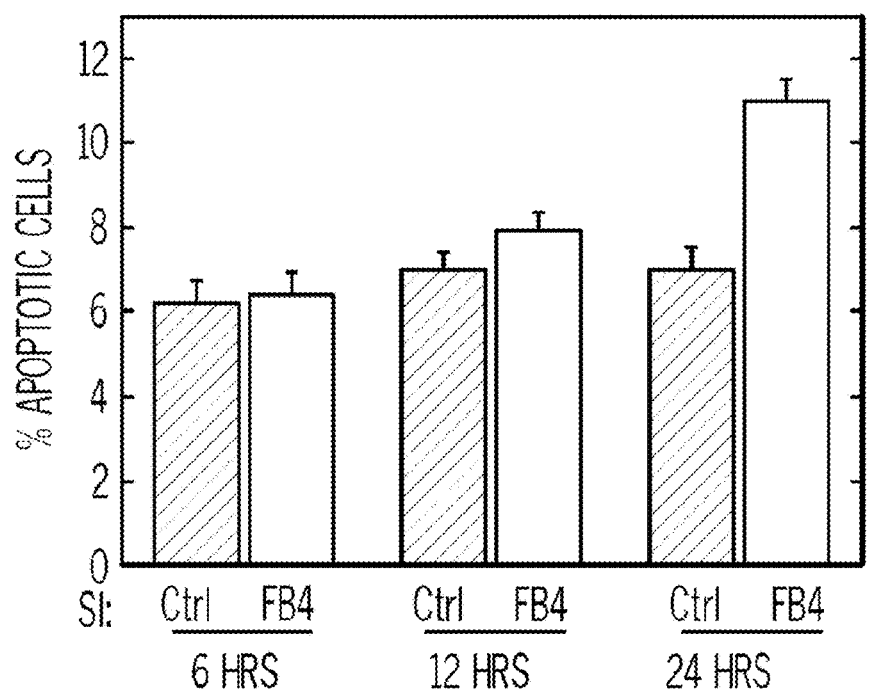
Figure 3:
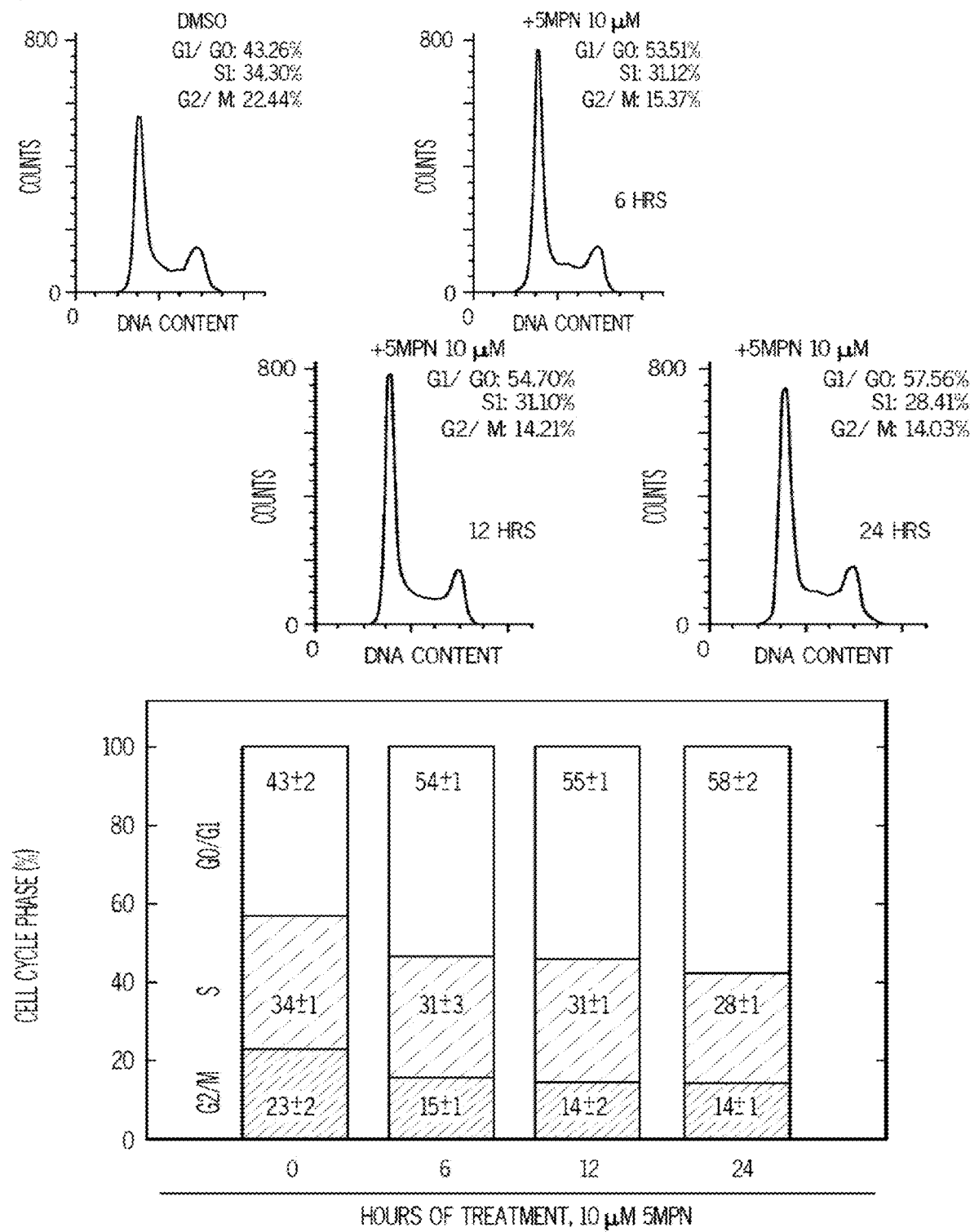
Figure 3:
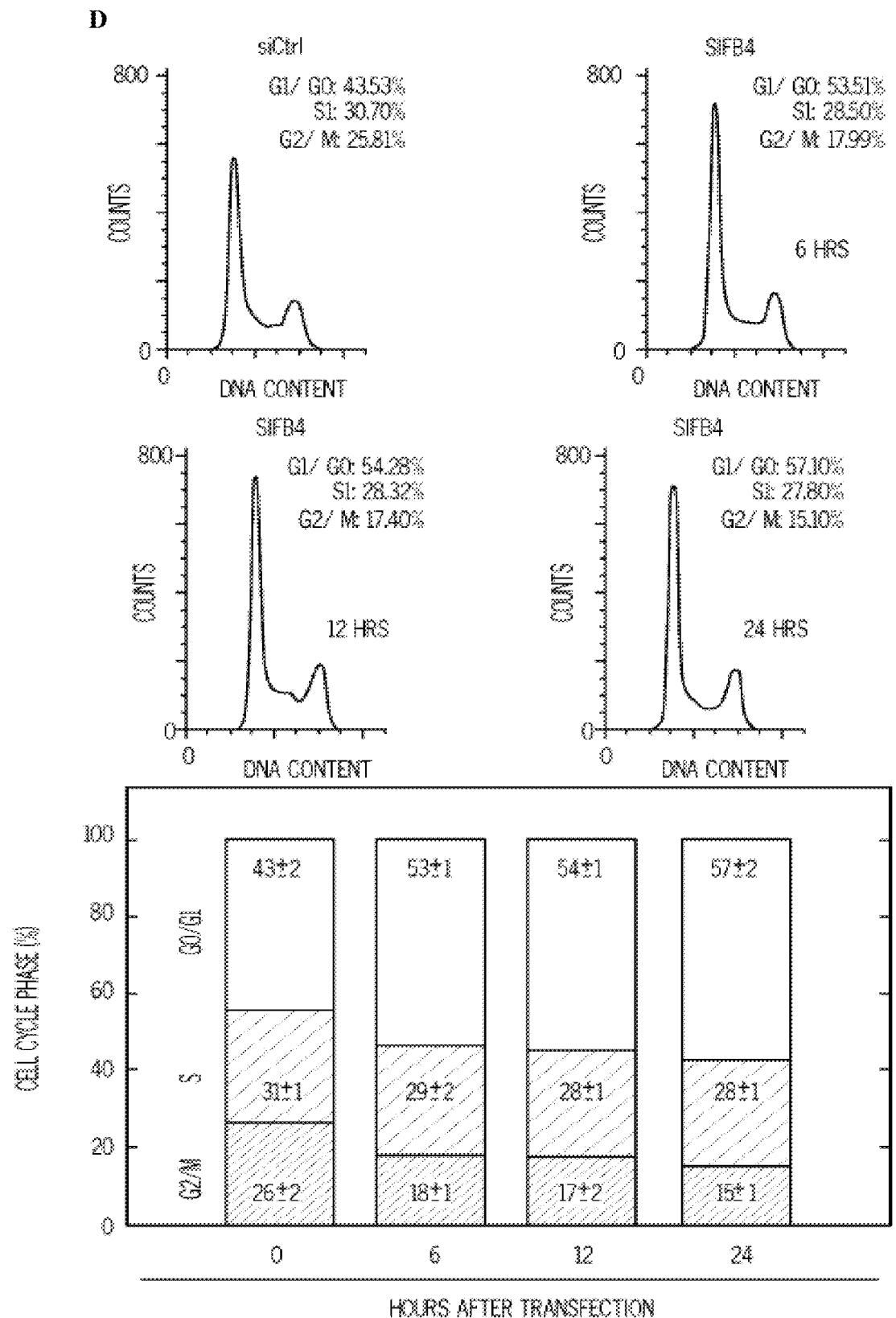
Figure 3:
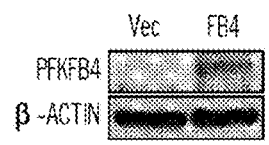
Figure 3:
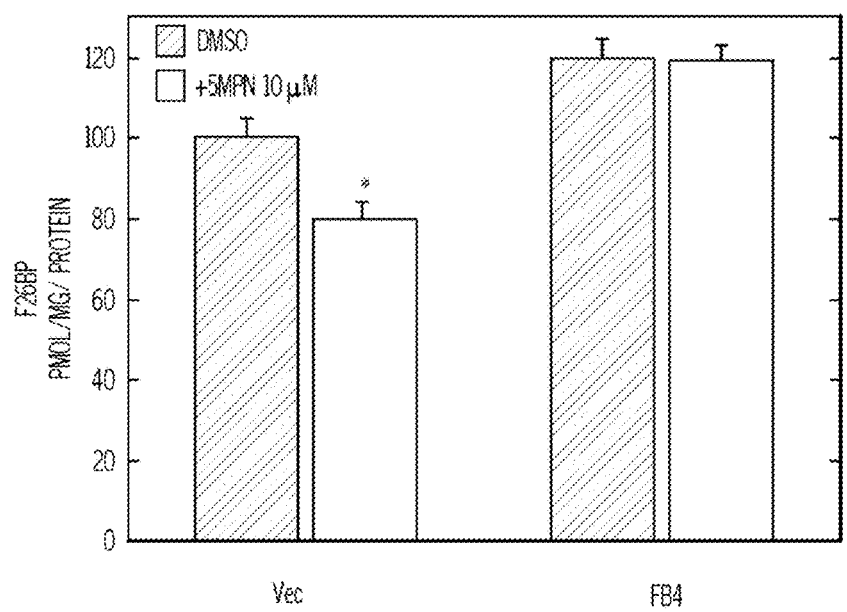
Figure 3:
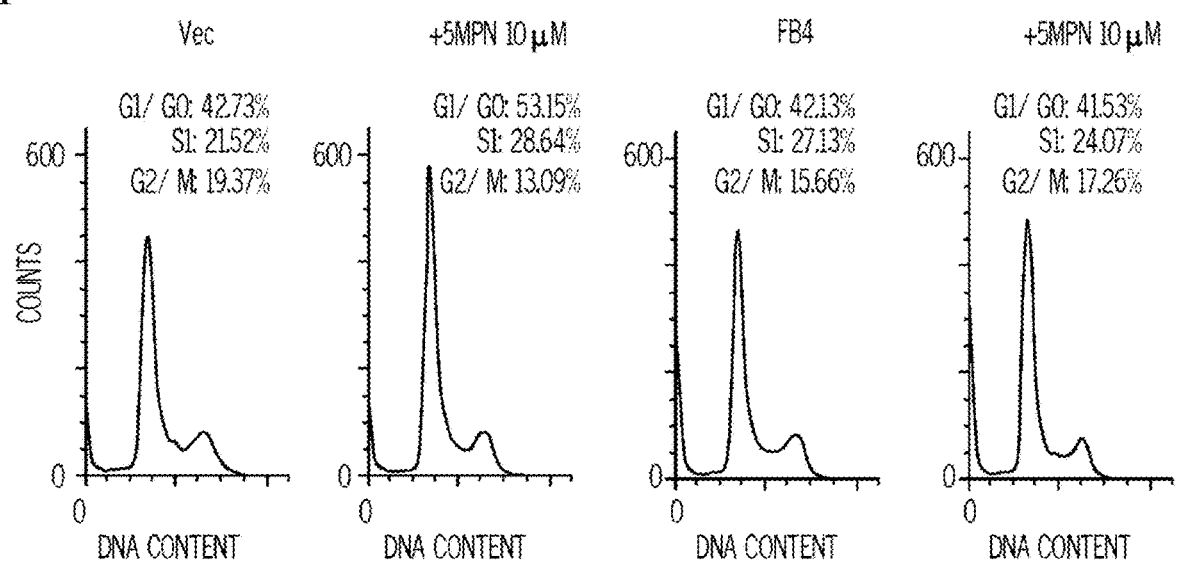

PFKFB4 Inhibition with 5MPN Causes a G1 Cell Cycle Arrest that is Reversed by PFKFB4 Over-Expression Results:

We noted a reduction in viable H460 cells after exposure to 5MPN for 48 hours (see FIG. 2B) and postulated that 5MPN was inducing apoptosis, arresting cell cycle progression, or both. Whereas we observed an increase in apoptotic cells after 5MPN exposure or selective PFKFB4 siRNA transfection (FIG. 3A and FIG. 3B), we observed a G1 arrest with both 5MPN and PFKFB4 siRNA (FIG. 3C and FIG. 3D). We then over-expressed PFKFB4 and exposed the H460 cells to 5MPN at the indicated concentrations and assessed the effects on cell cycle and F2,6BP. We found that overexpression of PFKFB4 reversed the reduction in F2,6BP (FIG. 3E) and G1 arrest (FIG. 3F) caused by 5MPN. These studies suggest that 5MPN is suppressing PFKFB4 which in turn is resulting in a reduction in the G1/S transition.

Example 5

Figure 4:
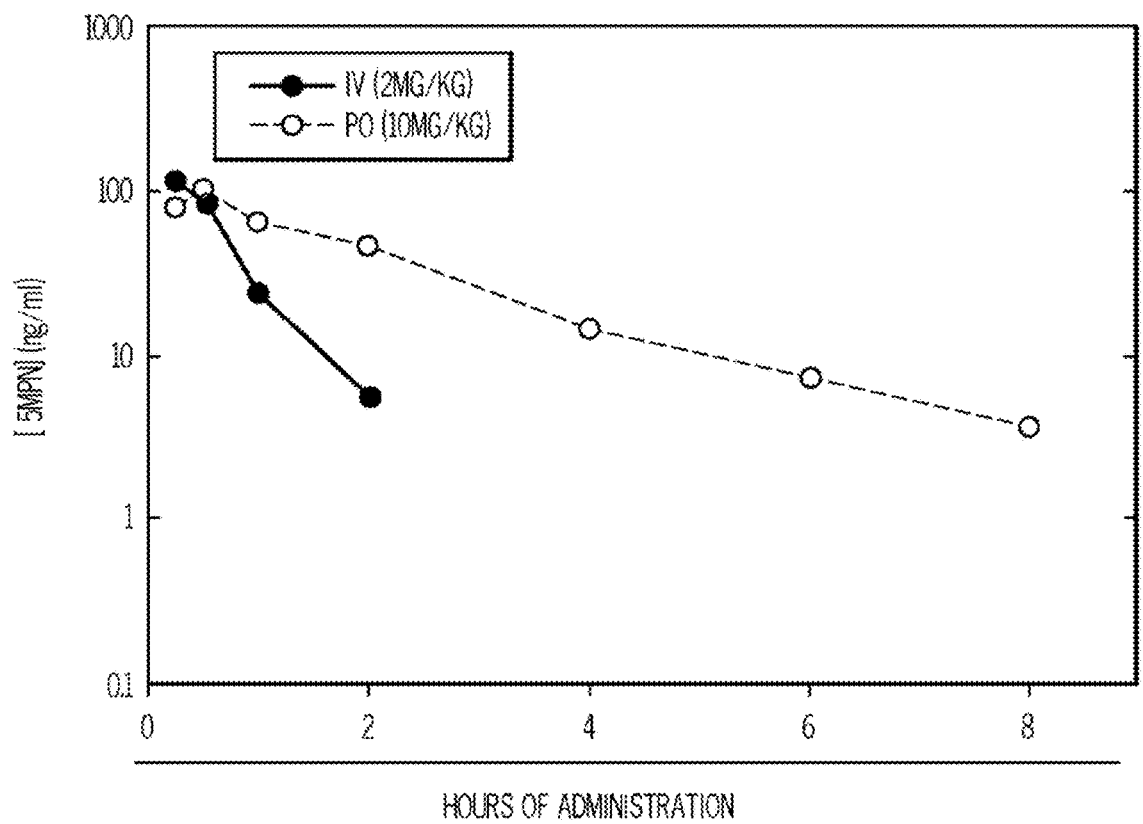
FIG. 4. 5MPN has oral bioavailability and suppresses glucose uptake and tumor growth in mice. Panels (A) and (B) show the oral and intravenous pharmacokinetic properties of 5MPN were in C57BL/6 mice. Groups of 10 C57BL/6 mice were implanted with LLC cells and, when tumors reached a mass of 150-200 mg, were randomized to daily administration of DMSO or 5MPN by gavage (120 mg/kg, for ten days). Panels (C) and (D) show daily tumor and daily body mass measurements, respectively. Panel (E) shows F2,6BP expression after 10 days of daily administration of DMSO or 5MPN (120 mg/kg) by gavage. The mice were euthanized, and tumors extracted and analyzed for F2,6BP (shown as % of DMSO). Panel (F) shows micro-PET scans obtained from separate groups of tumor-bearing mice that were administered either DMSO or 5MPN (120 mg/kg by gavage, once). Regions of interest in the tumor and cerebellum were quantified in quadruplicate. Representative transverse view cuts are shown with red arrows indicating the tumor. Panel (G) shows the in vitro cell cycle analysis of LLC cells that were exposed to DMSO±10 μM 5MPN. Panel (H) shows Ki67 staining in LLC xenografs that were examined by immunohistochemistry (representative sections shown, 10× and 25× magnification). Groups of 10 C57BL/6 mice were implanted with LLC cells and, when tumors reached a mass of 150-200 mg, were randomized to daily administration of DMSO or 5MPN by gavage (120 mg/kg, for ten days). Panel (I) shows Ki67 positive pixels that were enumerated in a minimum of 5 fields per tumor section. Groups of 10 C57BL/6 mice were implanted with LLC cells and, when tumors reached a mass of 150-200 mg, were randomized to daily administration of DMSO or 5MPN by gavage (120 mg/kg, for ten days). Panels (J) and (K) show tumor and body mass measurements (collected daily), respectively, of groups of 10 BALB/c athymic mice implanted with H460 NSCLC cells and, when tumors were 150-200 mg, were randomized to daily DMSO or 5MPN by gavage. *p value<0.01 compared to controls.
Figure 4:
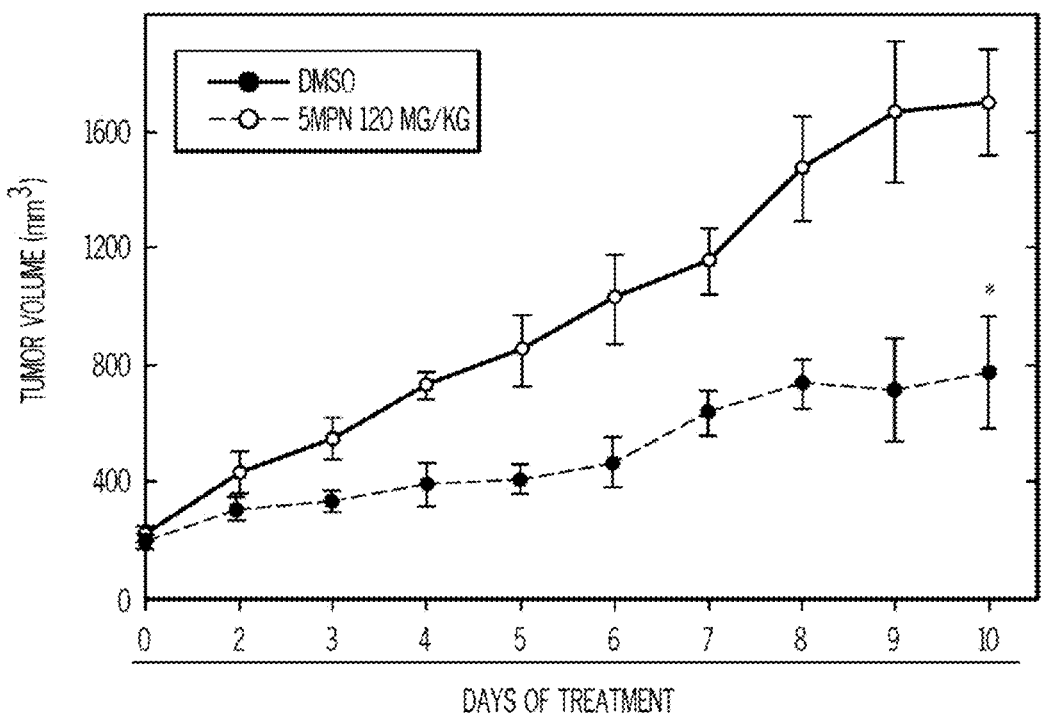
Figure 4:
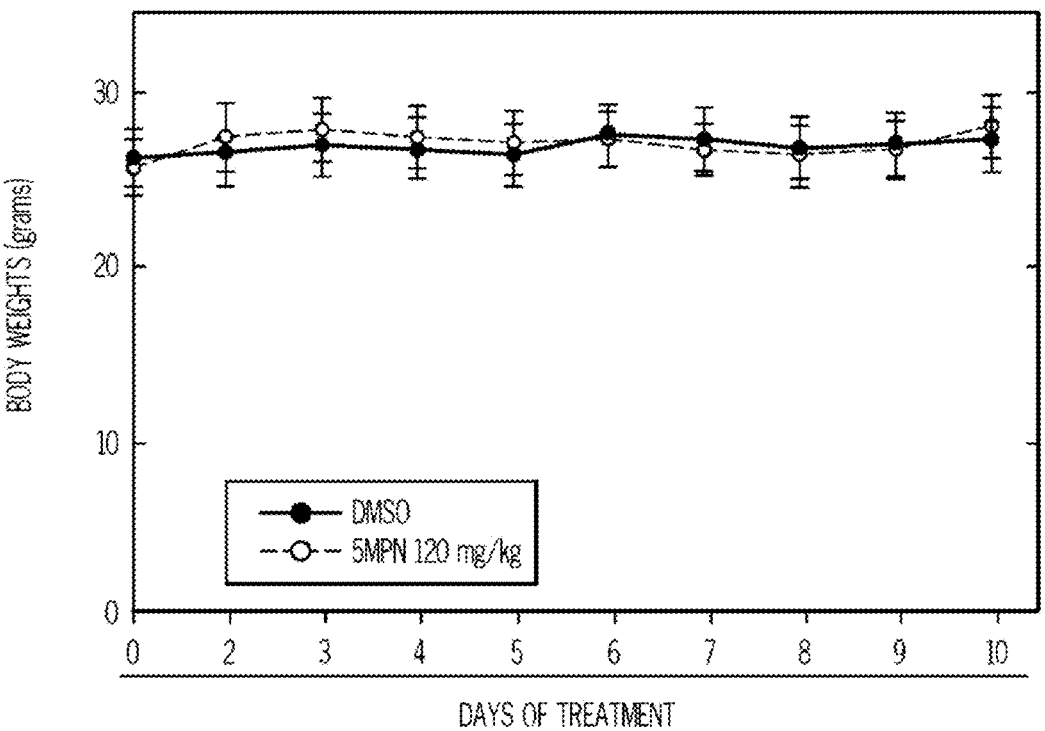
Figure 4:
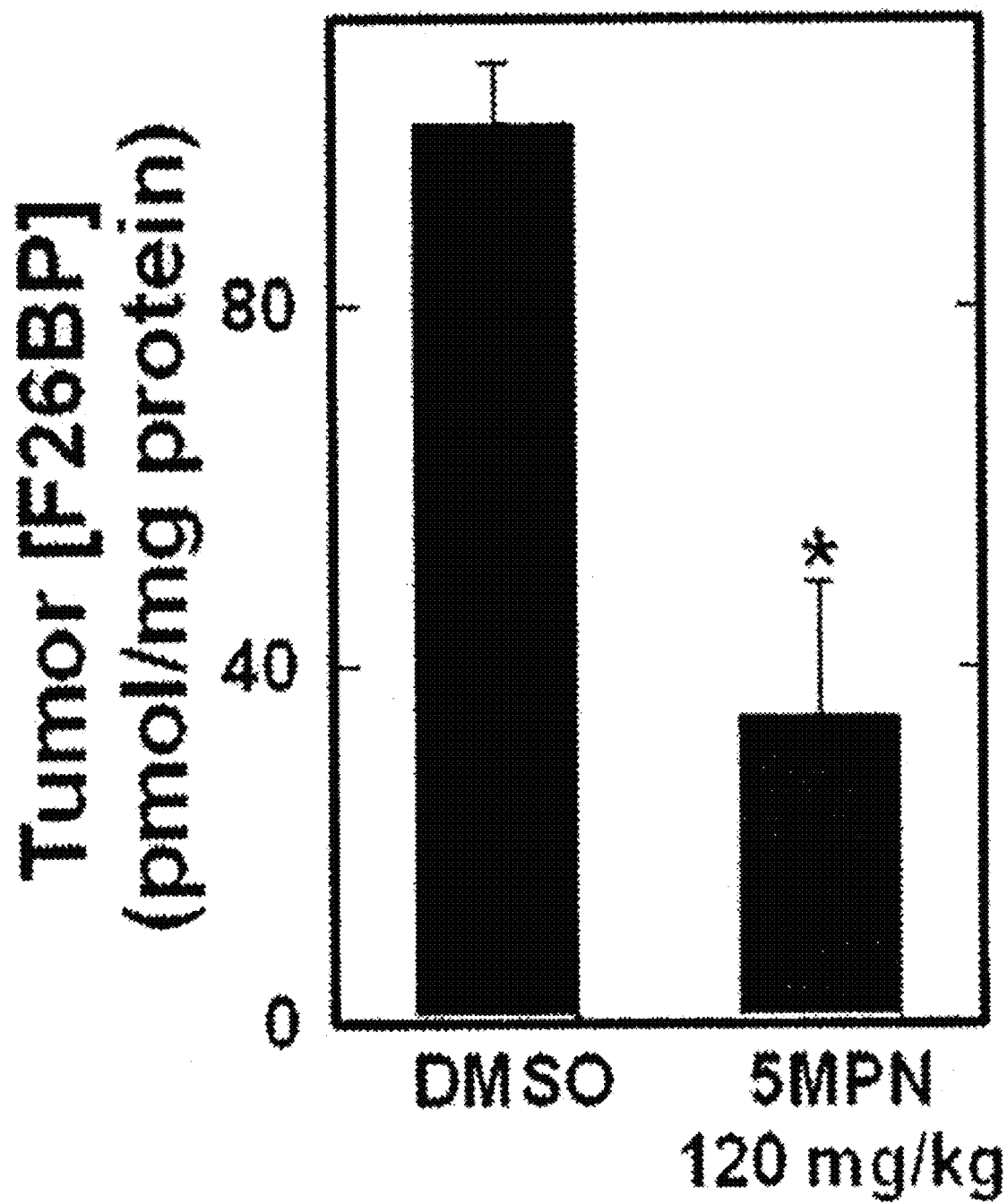
Figure 4:
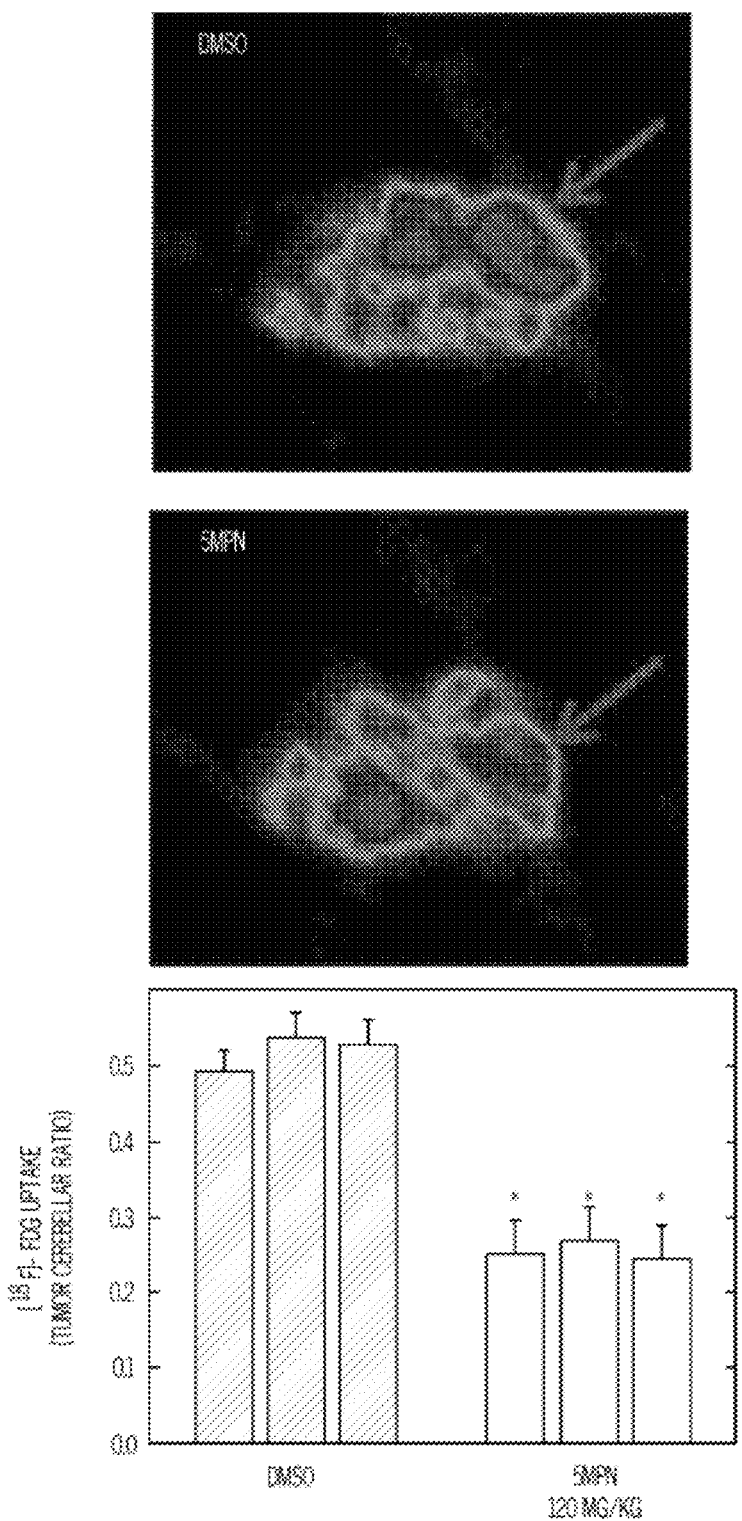
Figure 4:
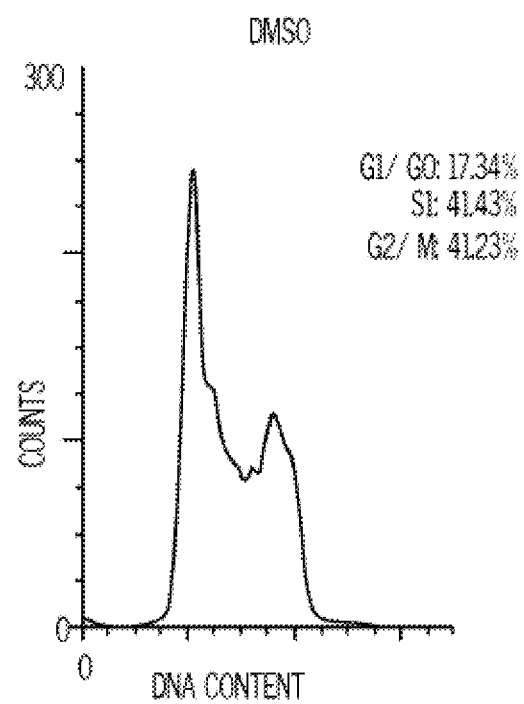
Figure 4:
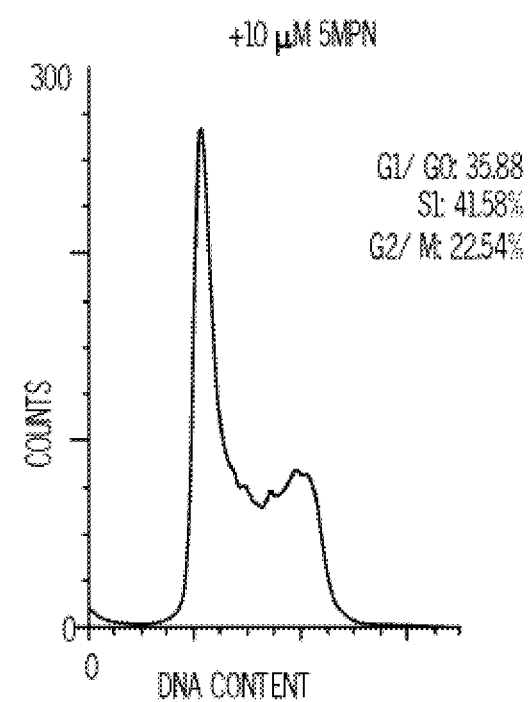
Figure 4:
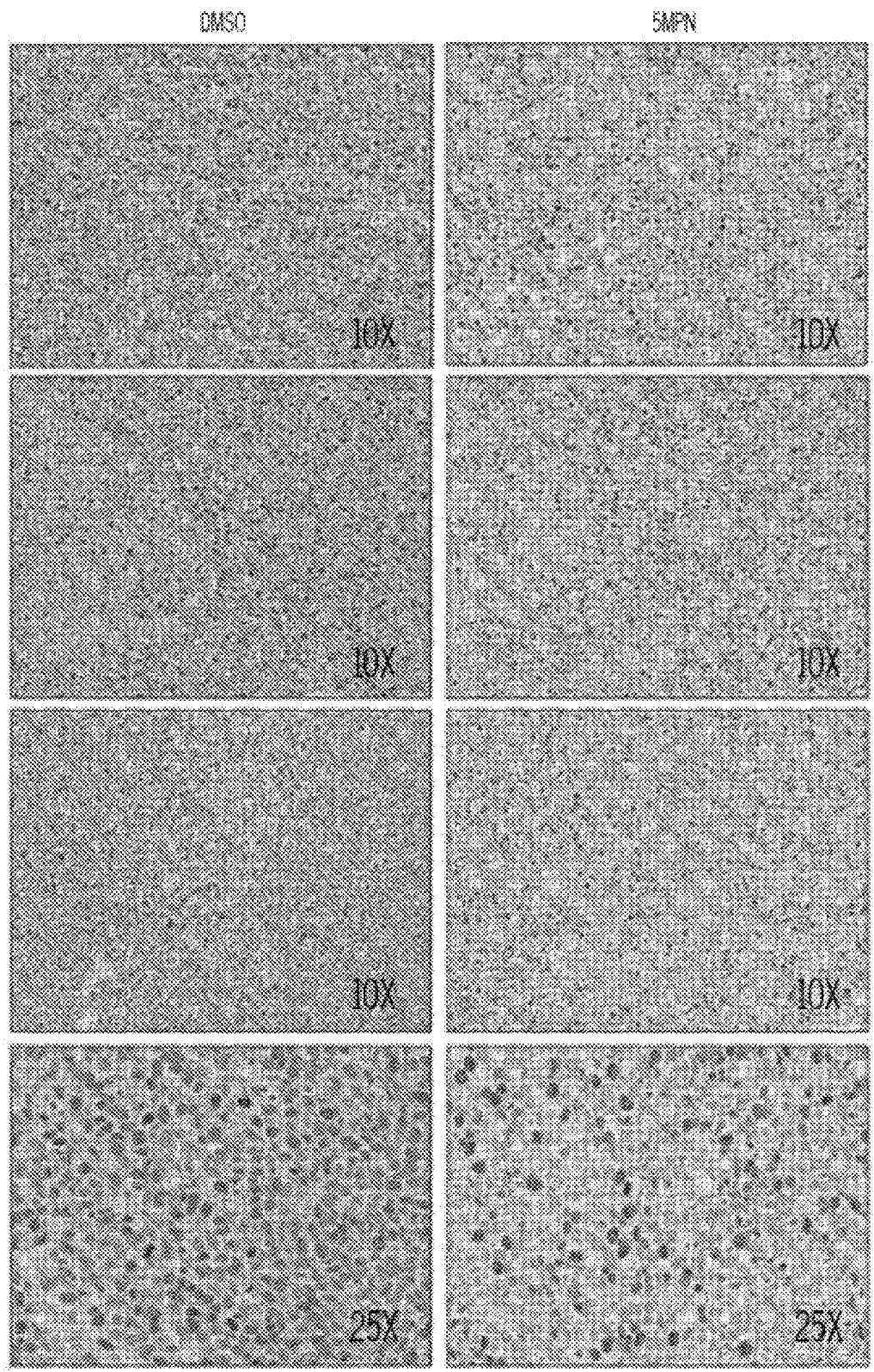
Figure 4:
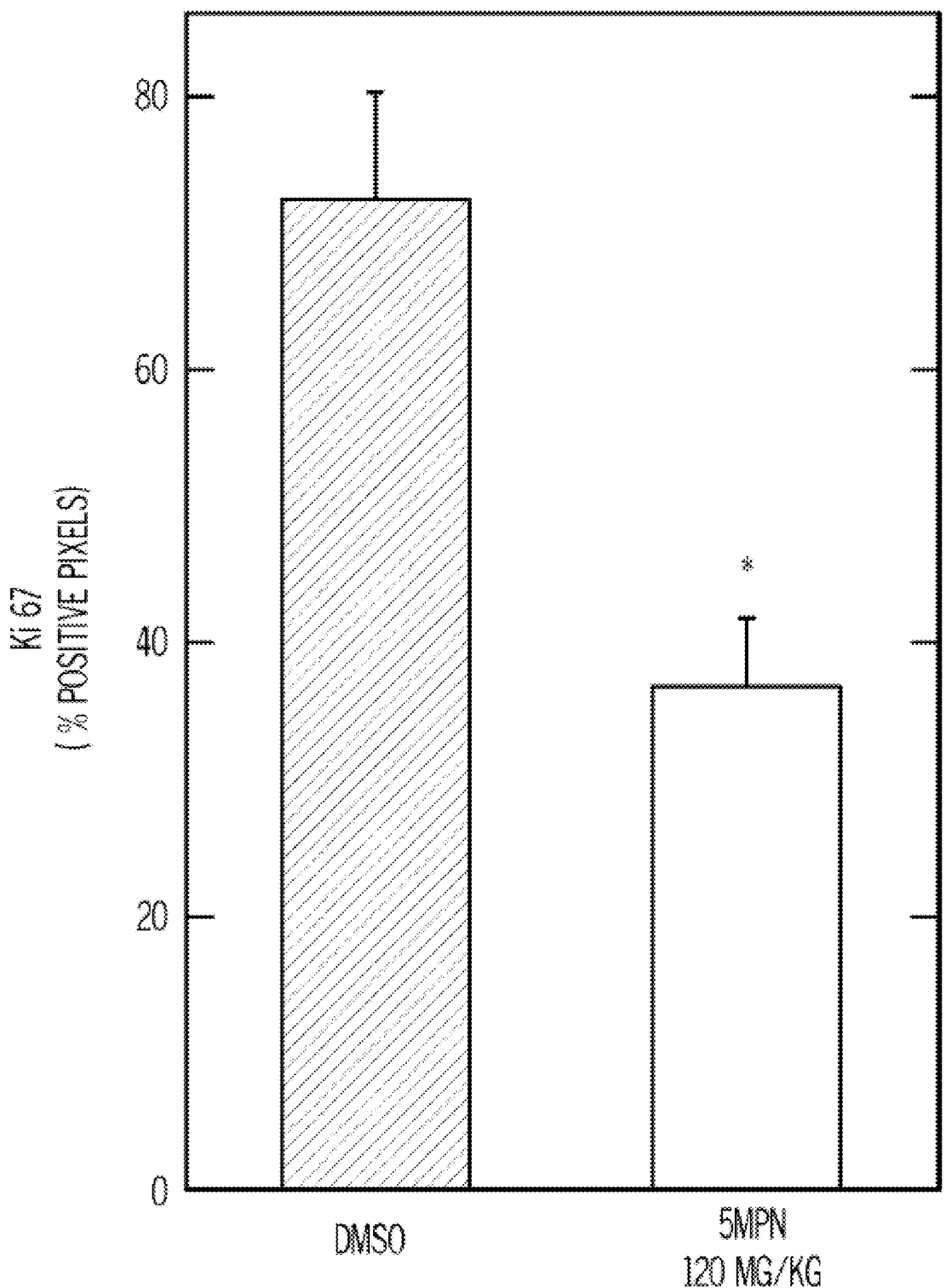
Figure 4:
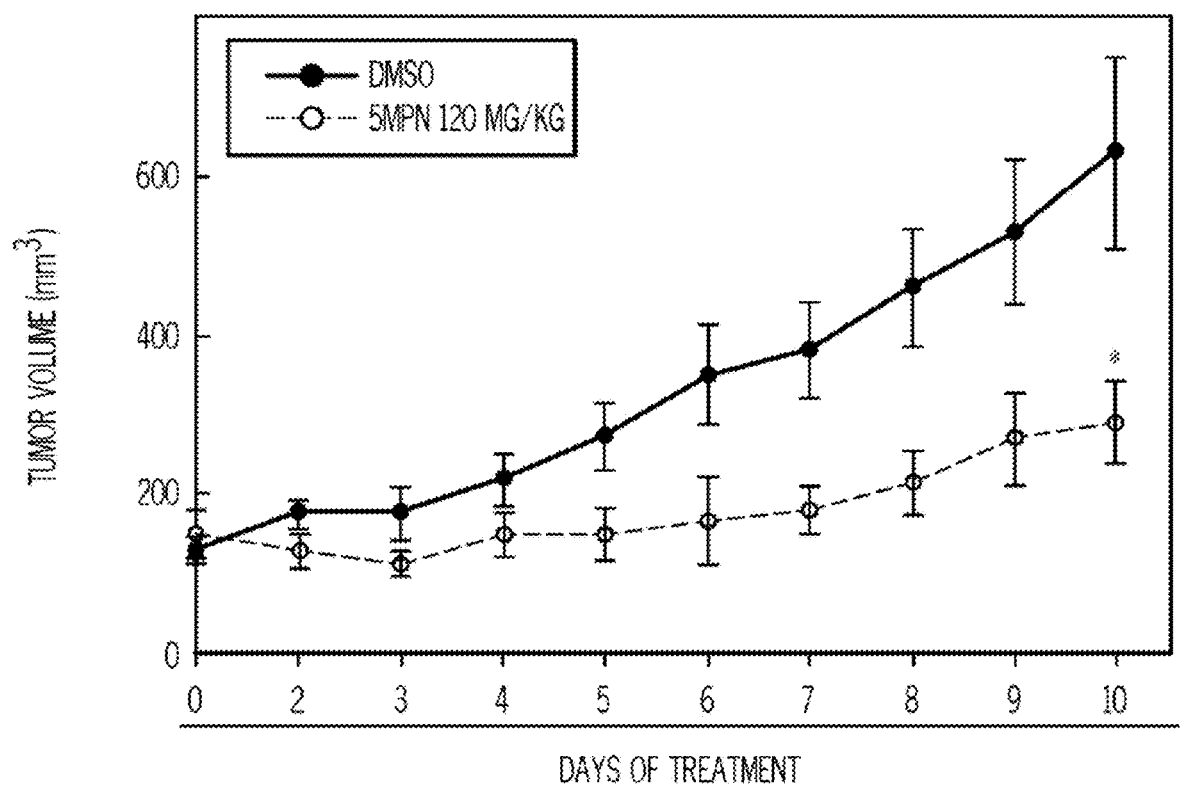
Figure 4:
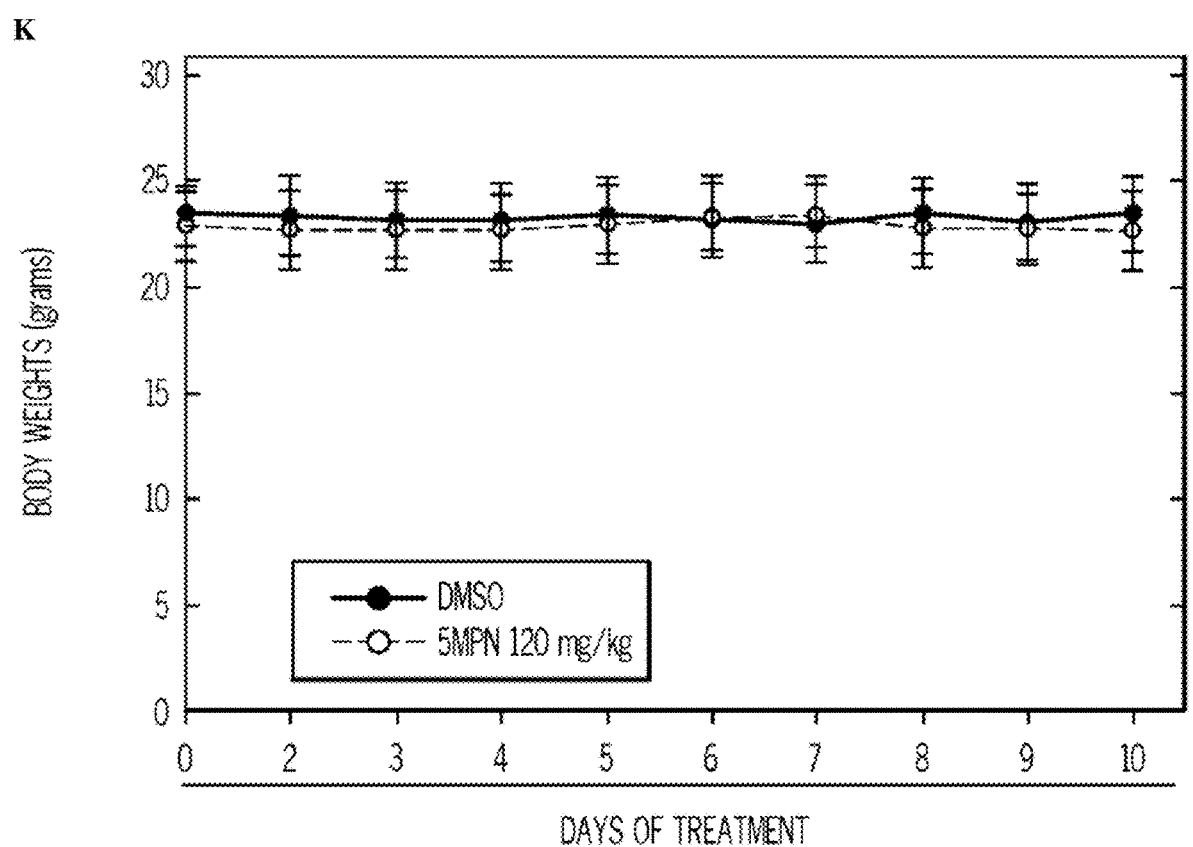

5MPN has Oral Bioavailability and Suppresses the Glucose Uptake and Growth of Tumors in Mice Results:

The pharmacokinetics of intravenous and oral administration of 5MPN was studied and revealed that both routes were adequate to achieve potentially therapeutic concentrations when administered daily (FIG. 4A and FIG. 4B). Given the potential usefulness of oral administration in terms of cost and convenience, we elected to pursue this route in subsequent toxicity and efficacy pre-clinical studies. Initially, we dosed C57BL/6 mice with 120 mg/kg PO for two weeks and analyzed the effect on complete blood counts, electrolytes, hepatic and renal function, body mass and the gross and histological appearance of the brain, heart, lungs, liver, kidneys and spleen. We found no signs of toxicity either from these objective measures or from any behavioral or clinical changes (i.e. ruffled fur, lethargy, ataxia or labored respiration). At this oral dose, it was determined that 5MPN suppressed the growth of Lewis lung carcinomas grown in syngeneic mice (FIG. 4C) and H460 human lung adenocarcinoma xenografts grown in athymic mice (FIG. 4J) without affecting body weight (FIG. 4D and FIG. 4K). Next, the effects of oral administration of 5MPN on intratumoral F2,6BP and glucose uptake by LLC xenografts was examined. There was a reduction in F2,6BP (FIG. 4E) and 2-[$^{18}$F]-fluoro-2-deoxyglucose uptake using positron emission tomography (FIG. 4F). It was confirmed that 5MPN caused a G1 arrest in LLC cells in vitro similar to H460 cells (FIG. 4G). The number of Ki67-positive cells was examined since Ki-67 expression correlated with later S and G2 phases of the cell cycle (SASAKI et al. "The cell cycle associated change of the Ki-67 reactive nuclear antigen expression" J Cell Physiol (1987) Vol. 133, No. 3, pp. 579-584). It was determined that oral administration of 5MPN caused a reduction in Ki67-positive cells in the LLC xenografts (FIG. 4H and FIG. 4 I) suggesting that 5MPN may be reducing cell cycle progression in vivo.

Example 6

Figure 5:
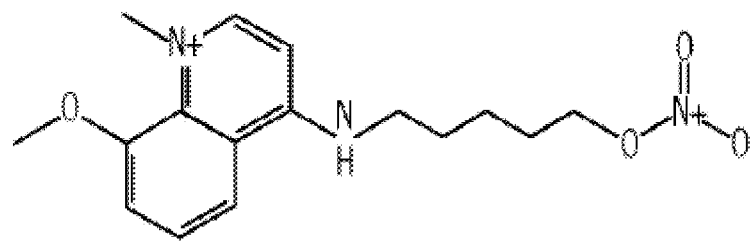
FIG. 5. MPN-2 inhibits recombinant PFKFB4 enzyme activity, decreases the production of F2,6BP, decreased proliferation of cancer cells, and has oral bioavailability. Panel (A) shows the molecular structure of MPN-2. Panel (B) shows that MPN-2 inhibits PFKFB4 activity. Panel (C) shows that MPN-2 inhibits F2,6BP production. Panel (D) shows that MPN-2 decreases the proliferation of a human cancer cell line, H460 NSCLC cells. Viable cells counted at 48 hours and at 72 hours. Panel (E) shows the oral and intravenous pharmacokinetic properties of MPN-2 in CD-1 mice (N=3).
Figure 5:
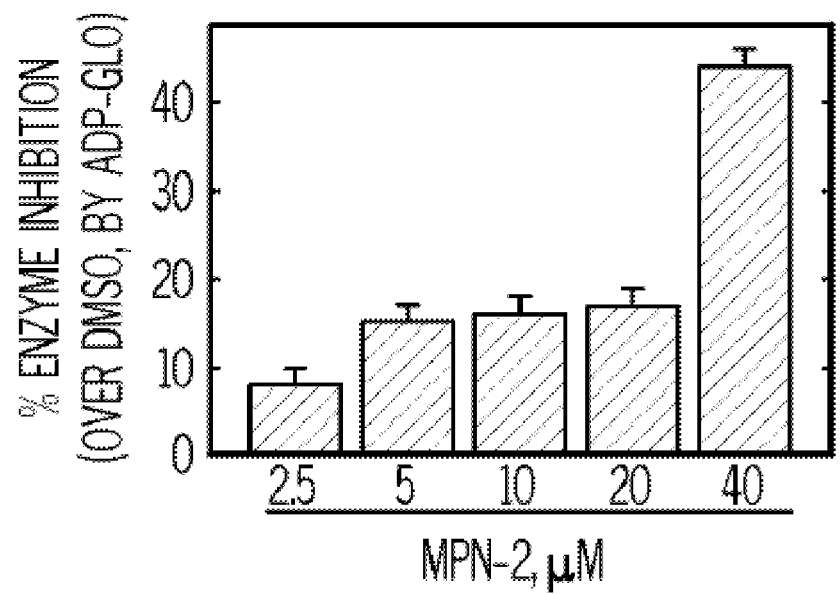
Figure 5:
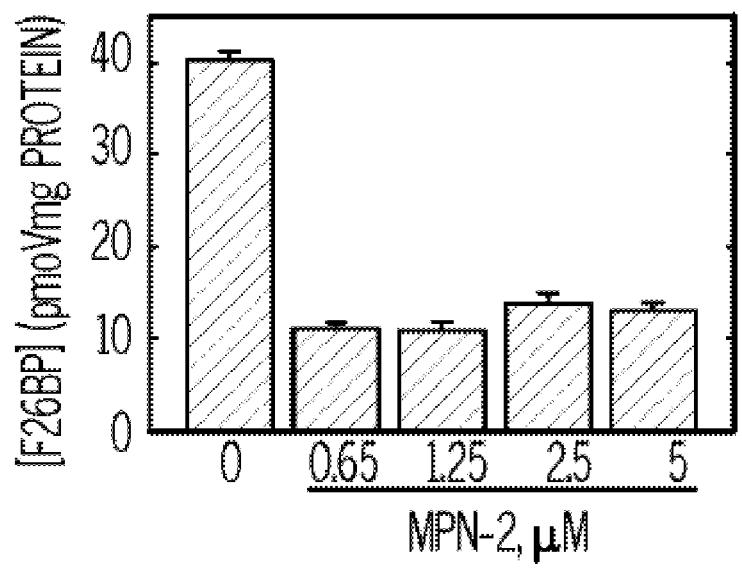
Figure 5:
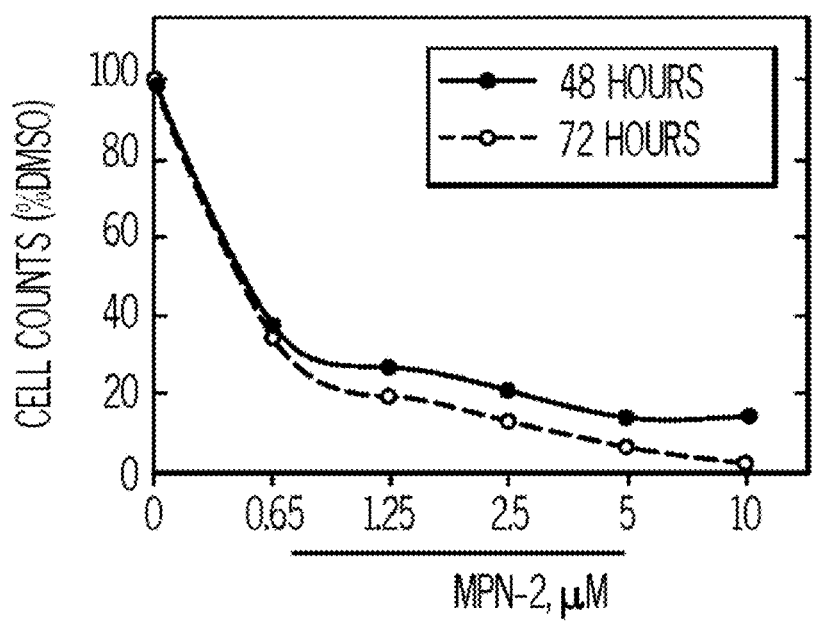
Figure 5:
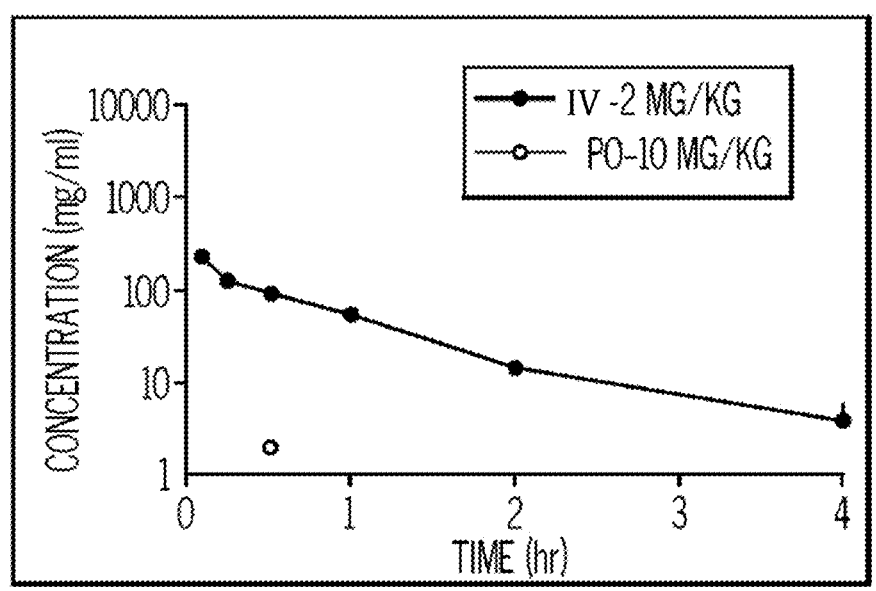

MPN-2 Inhibits Recombinant PFKFB4 Enzyme Activity, Decreases the Production of F2,6BP, Decreased Proliferation of Cancer Cells, and has Intravenous Bioavailability Results:

5-[(8-methoxy-2-methylquinolin-1-ium-4-yl)amino]pentyl nitrate (MPN-2) inhibited PFKFB4 activity (FIG. 5B) and F2,6BP production (FIG. 5C). MPN-2 decreased the proliferation of a human cancer cell line, H460 NSCLC (FIG. 5D). Viable cells counted at 48 hours and at 72 hours. Pharmacokinetic analysis of intravenous and oral administration of MPN-2 determined that MPN-2 exhibits intravenous bioavailability. FIG. 5E shows the oral and intravenous pharmacokinetic properties of MPN-2 in CD-1 mice (N=3)

Example 7

Figure 6:
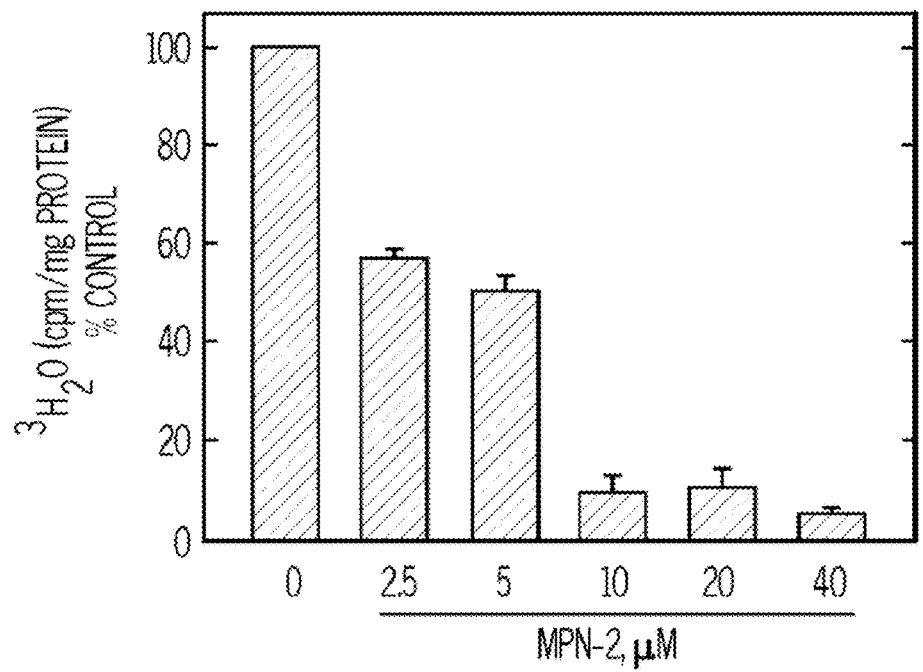
FIG. 6. MPN-2 causes decreased proliferation of cancer cells preceded by a reduction in intracellular glycolysis and ATP, decreased proliferation of cancer cells, and tumor growth in mice. Panels (A) and (B) show the results of H460 NSCLC cells treated with DMSO±the indicated concentrations of MPN-2. The effects on glycolysis (A) and ATP (B) were measured after 48 hours. Panel (C) shows that MPN-2 decreases the proliferation of MCF7, SK-BR-3, H460, and A549 cells exposed to DMSO±the indicated concentrations of MPN-2 after 24-72 hours (72 hours shown). Panel (D) shows daily tumor mass measurements of groups of 10 C57BL/6 mice that were implanted with LLC cells and, when tumors reached a mass of 150-200 mg, were randomized to daily administration of DMSO or 5MPN in DMSO at the indicated dose by intraperitoneal injection (10 mg/kg, for eleven days).
Figure 6:
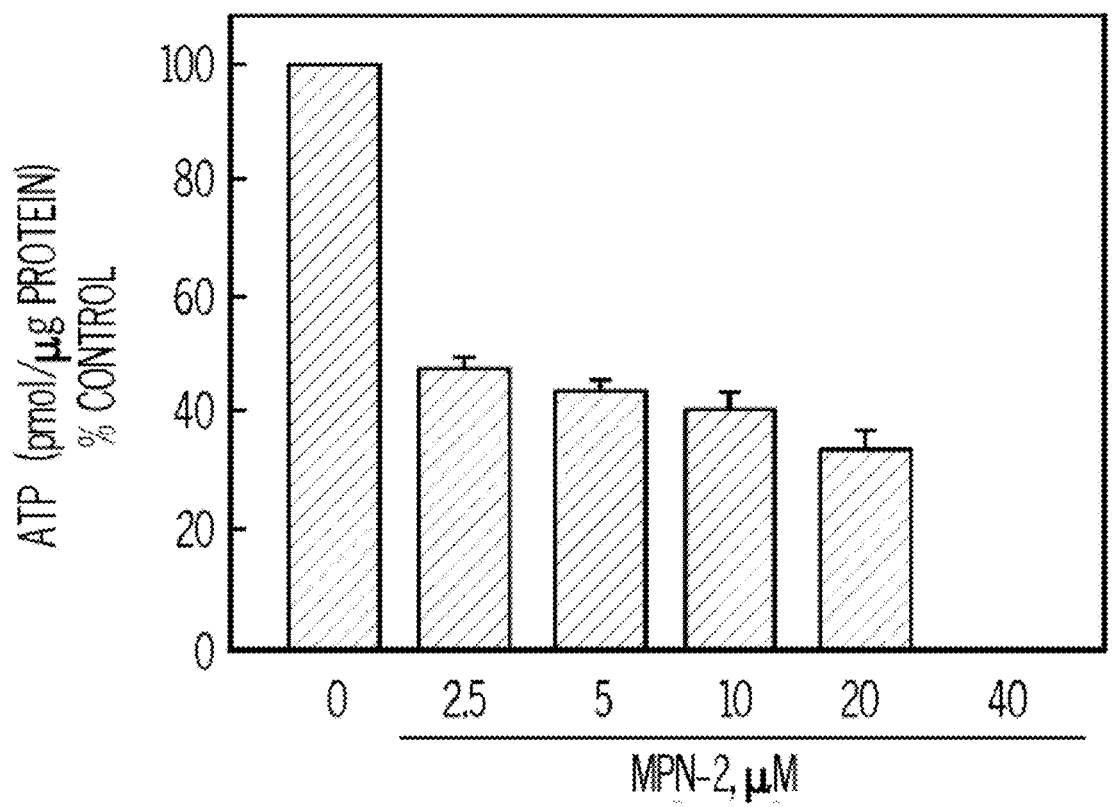
Figure 6:
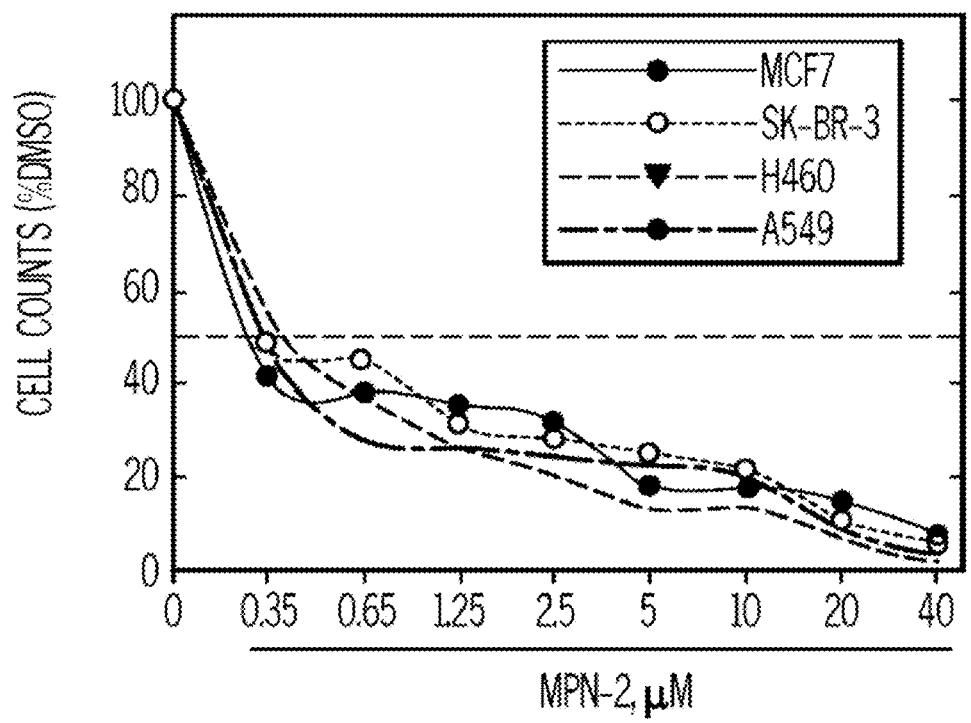
Figure 6:
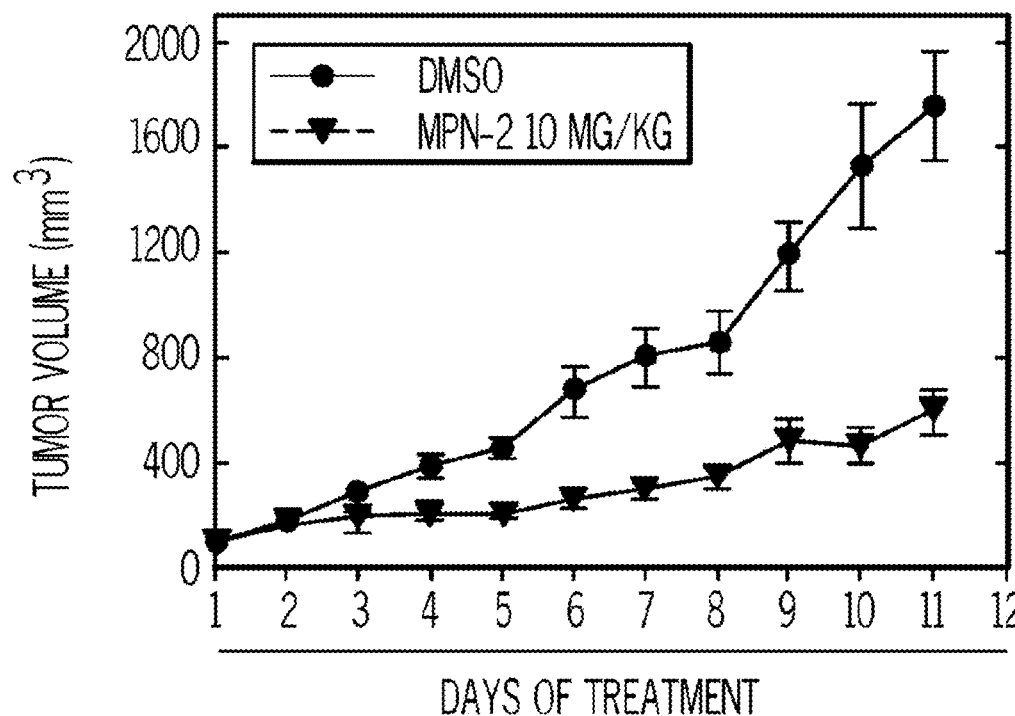

MPN-2 Causes Decreased Proliferation of Cancer Cells Preceded by a Reduction in Intracellular Glycolysis and ATP, Decreased Proliferation of Cancer Cells, and Tumor Growth in Mice Results:

MPN-2 decreased intracellular glycolysis (FIG. 6A) and ATP (FIG. 6B) production of H460 NSCLC cells treated with DMSO±the indicated concentrations of MPN-2. The effects on glycolysis (FIG. 6A) and ATP (FIG. 6B) were measured after 48 hours. Furthermore, MPN-2 decreased the proliferation of various cancer cell lines. FIG. 6C shows the decreased proliferation of MCF7, SK-BR-3, H460, and A549 cells exposed to DMSO±the indicated concentrations of MPN-2 after 24-72 hours (72 hours shown). Furthermore, it was determined that MPN-2 suppressed the growth of Lewis lung carcinomas grown in C57BL/6 mice (FIG. 6D). When tumors reached a mass of 150-200 mg, mice were randomized to daily administration of DMSO or 5MPN in DMSO at the indicated dose by intraperitoneal injection (10 mg/kg, for eleven days).

Example 8

Formula IV Compounds Decreased Proliferation of Cancer Cells

Results:

We also examined the effect of the compounds of Formula IV on the proliferation of H460 non-small cell lung cancer, H460. Formula IV compounds, specifically

Figure 7:
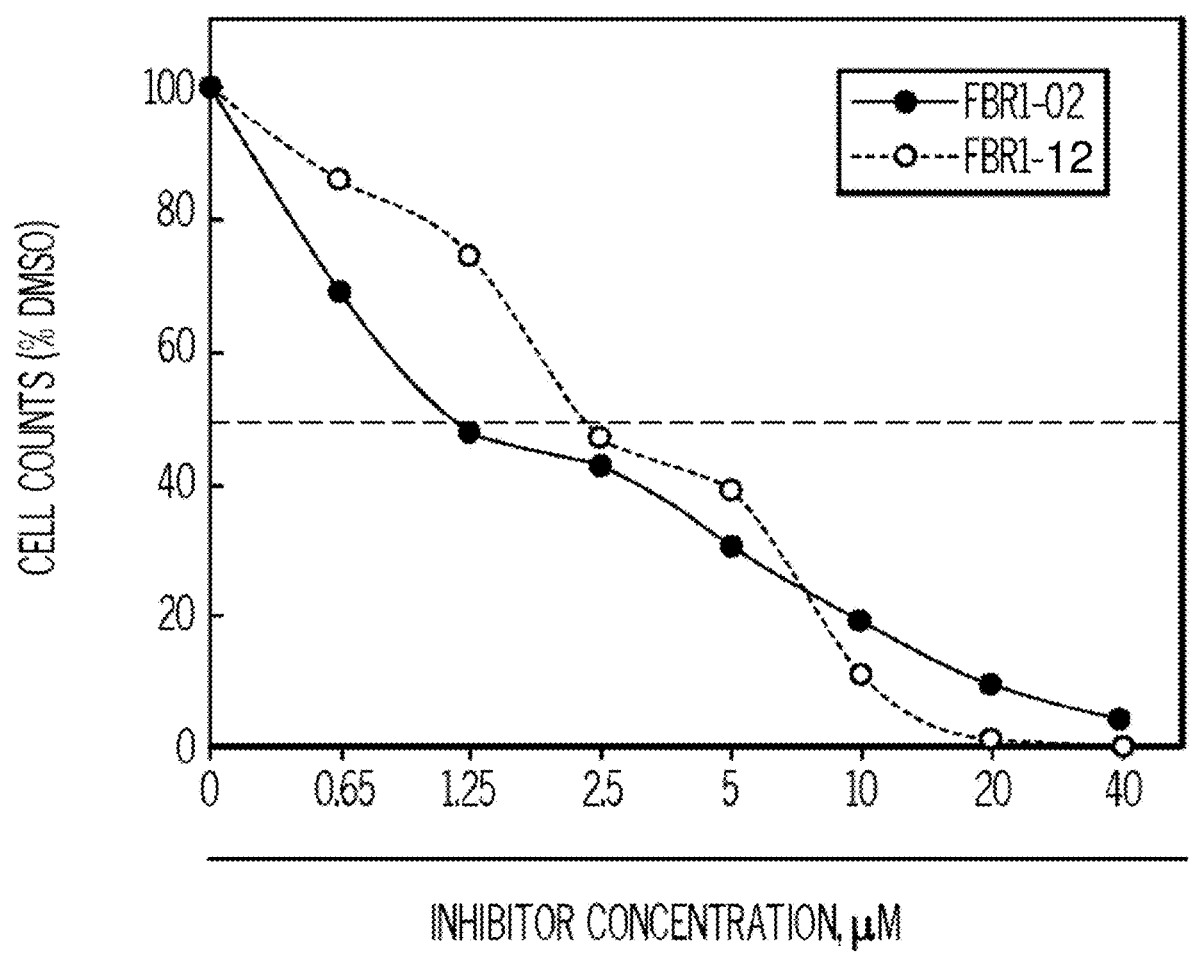
FIG. 7. Formula IV compounds decreased proliferation of cancer cells.

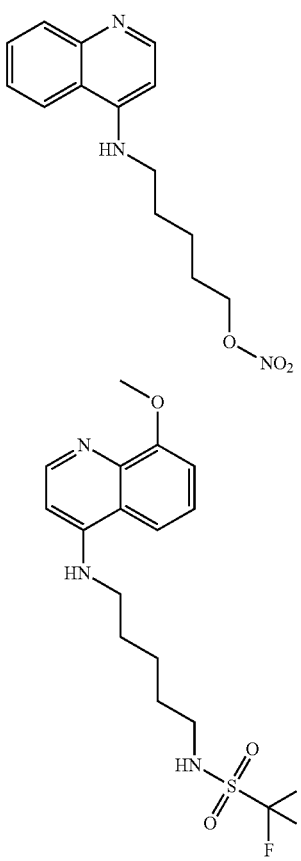

decreased the proliferation of the H460 NSCLC cells (FIG. 7).

Example 9

Dual PFKFB4 and PFKFB3 Inhibition with MPN-2 and PFK15, Respectively, Causes a Synergistic Increase in Cell Death Results:

We examined the effect of combination therapy of a PFKFB4 inhibitor and a PKFB3 inhibitor. FIG. 8 shows that simultaneous administration of MPN-2 (determined by the instant investigators to be a PFKFB4 inhibitor) and PFK15 (Tocris, a commercially available PFKFB3 inhibitor) synergistically increased cell death in vitro. Thus, combination therapy with PFK15 (and other PFKFB3 inhibitors) and the presently-disclosed small molecule antagonists of the kinase domain of PFKFB4 may be used to provide an effective chemotherapeutic regimen.

Example 10

Synthesis of the Small Molecule Antagonists of the Kinase Domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and Salts Thereof Referring to FIG. 9, the synthesis of some disclosed small molecule antagonists of the kinase domain of PFKFB4 (e.g., Formula (I), Formula (II), Formula (III), Formula (IV), Formula (V), Formula (VI), Formula (VII), Formula (VIII), Formula (IX), Formula (X), 5MPN, MPN-2, and salts thereof) began with the condensation of Meldrum's acid (1) with aniline 2 in the presence of trimethyl orthoformate to afford adduct 3 in excellent yield (GHOSH et al., "Discovery of 4-(4-(2-((5-Hydroxy-1,2,3,4-tetrahydronaphthalen-2-yl) (propyl)amino)ethyl)piperazin-1-yl)quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease" J. Med. Chem. (2010) Vol. 53, pp. 2114-2125). Cyclization was facilitated by heating 3 in diphenyl ether to produce 8-methoxyquinolin-4-ol (4) core, which was subsequently converted to chloride 5 by refluxing in phosphoryl chloride (Id.). The carbon linker was installed by heating chloride 5 with a commercially available primary amine (PEREZ et al., "N-Cinnamoylated Chloroquine Analogues as Dual-Stage Antimalarial Leads" J. Med. Chem. (2013) Vol. 56, pp. 556-567). In the final step, several conditions were surveyed for nitric acid ester formation and many were sluggish or produced multiple byproducts. Ultimately, treating alcohol 6 with concentrated nitric acid, acetic acid, and acetic anhydride in ethyl acetate produced the desired product (ZIAKAS et al. "Nitric oxide releasing derivatives of tolfenamic acid with anti-inflammatory activity and safe gastrointestinal profile" Bioorg. Med. Chem. (2005) Vol. 13, pp. 6485-6492.)

Still referring to FIG. 9, the synthesis is amendable to produce a library of derivatives. For example, the carbon linker can be altered by treating chloride 5 with a variety of nucleophiles. Furthermore, the primary alcohol of compound 6 can be functionalized with groups other than the nitric acid ester. Attempts were made to prepare the 2-methylquinoline salt by treating 7 with methyl iodide in acetonitrile. Decomposition was observed. In some instances, a salt may need to be prepared prior to the installation of the nitric acid ester.

Example 11

Some Synthetic Methods and Compound Characterization

All commercially purchased chemicals and solvents were used without further purification. All reactions were conducted under a nitrogen atmosphere in flame dried glassware. Reactions were monitored by thin-layer chromatography (TLC) on silica gel plates (Analtech, Uniplates GHLF, 0.25 mm with UV254) and were visualized with UV light (254 nm and 360 nm) or potassium permanganate stain. Isolated compounds were purified via flash chromatography on a Teledyne Isco Combiflash $R_f$ with prepacked silica gel columns eluted with an optimal gradient as described. All NMR spectra were recorded on an Agilent 400 MR spectrometer equipped with an OneProbe at 400 MHz for $^1H$, 376 MHz for $^{19}F$ and 100 MHz for $^{13}C$. Chemical shifts were recorded as δ values in parts per million (ppm) at 25° C. and either tetramethylsilane (TMS) or residue solvent was used as an internal standard. Coupling constants are reported in hertz (Hz) and splitting patterns are designated as s, singlet; d, doublet; t, triplet; q, quartet; m, multiplet. Analytical purity was determined by reverse-phase high-performance liquid chromatography (RP-HPLC) on an Agilent 1260 infinity equipped with a diode array (160-450 nm). The instrument was equipped with an Agilent Zobrax Extend C-18 column (1.8 m, 2.1×50 mm) with mobile phase consisting of mass spectrophotometry grade water (with 0.1% formic acid and 0.1% methanol) and acetonitrile (with 0.1% formic acid). The RP-HPLC method employed a linear gradient from 5%-100% acetonitrile at 0.3 mL/min over 15 mins with 4 μL injection volume. High-resolution MS were recorded on an Agilent 6224 time-of-flight detector connected to the HPLC system that utilized electrospray ionization.

Compound VIII was synthesized according to the following synthetic scheme.

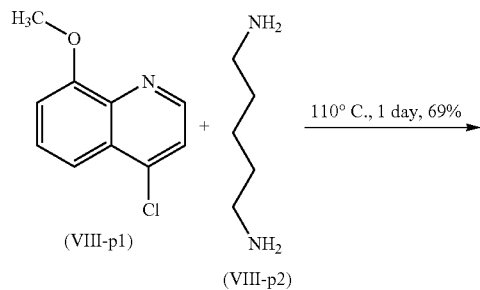

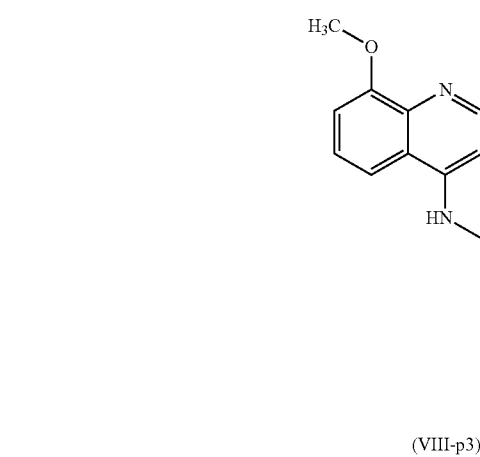

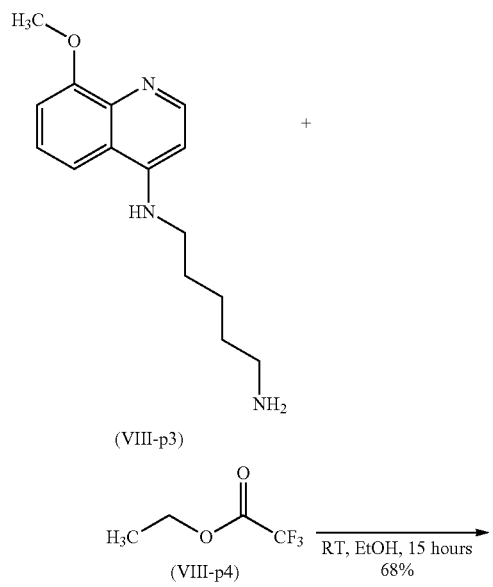

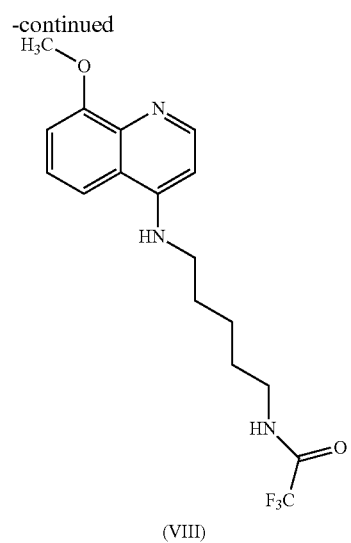

4-Chloro-8-methoxyquinoline (Formula (VIII-p1))

Formula (VIII-p1) was purchased (e.g., from MilliporeSigma (Order number: BBO000177-1G)) or prepared from 2-methoxyaniline using a modified literature procedure (GHOSH et al., "Discovery of 4-(4-(2-((5-Hydroxy-1,2,3,4-tetrahydronaphthalen-2-yl)(propyl)amino)ethyl)piperazin-1-yl)quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease." J. Med. Chem. (2010) Vol. 53, pp. 2114-2125, which is herein incorporated by reference in its entirety).

$N^1$-(8-methoxyquinolin-4-yl)pentane-1,5-diamine (Formula (VIII-p3))

A solution of 1.25 g (6.46 mmol) of Formula (II) in 2.0 mL of 1,5-diaminopentane (Formula (VIII-p2); purchased from TCI America (Order number: D0108)) was stirred at 110° C. for 24 hours. After cooling to room temperature, the solution was poured into 150 mL of ice water and then extracted three times with 150-mL portions of $CH_2Cl_2$. The combined organic layers were washed with water and brine, dried ($Na_2SO_4$) and concentrated in vacuo. The solid was chromatographed over silica gel (eluted with $CH_2Cl_2 \rightarrow 50\%$ MeOH) to afford 1.15 g (69%) of Formula (VIII-p3) as a tan solid. Alternatively or additionally, the solid can be purified by partially dissolving in ethyl acetate, sonicating for 5 mins and/or collecting the solid by filtration to afford semi pure product that is suitable for further use. $^1$H NMR (400 MHz, DMSO-$d_6$) δ 8.32 (d, J=5.2 Hz, 1H), 7.73 (dd, J=8.4, 0.8 Hz, 1H), 7.30 (td, J=8.4, 0.8 Hz, 1H), 7.05 (dd, J=8.0, 0.8 Hz, 1H), 6.99 (s, br, 1H), 6.44 (d, J=5.2 Hz, 1H), 3.88 (s, 3H), 3.23 (t, J=6.8 Hz, 2H), 2.54 (t, J=6.4 Hz, 2H), 1.65 (quint, J=7.2 Hz, 2H), 1.47-1.33 (m, 4H); $^{13}$C NMR (100.5 MHz, DMSO-$d_6$) δ 155.4, 149.7, 149.1, 140.2, 123.6, 119.6, 113.2, 108.0, 98.6, 55.5, 42.5, 41.5, 32.9, 27.8, 24.1. ESI-HRMS m/z: [M+H]$^+$ calcd for $C_{15}H_{22}N_3O$, 260.1757, found 260.1758.

2,2,2-trifluoro-N-(5-((8-methoxyquinolin-4-yl)amino)pentyl)acetamide (Formula (VIII))

To a solution of 1.1 g (4.24 mmol) of Formula (VIII-p3) in 40 mL of anhydrous ethanol was added 0.6 mL (660 mg, 4.7 mmol) of ethyl trifluoroacetate (Formula (VIII-p4); purchased from Oakwood Chemical (Order number: 001179)). The resulting solution stirred for 15 hours at room temperature and then was concentrated in vacuo. The product was chromatographed over silica gel (eluted with $CH_2Cl_2 \rightarrow 35\%$ MeOH) to afford 1.03 g (68%) of Formula (VIII) as a light grey, crystalline solid. $^1$H NMR (400 MHz, $CDCl_3$) δ 9.42 (t, J=5.2 Hz, 1H), 8.32 (d, J=6.0 Hz, 1H), 7.78 (dd, J=8.8, 1.2 Hz, 1H), 7.35 (t, J=8.0 Hz, 1H), 7.33 (s, br, 1H), 7.12 (d, J=7.2 Hz, 1H), 6.52 (d, J=5.6 Hz, 1H), 3.91 (s, 3H), 3.28 (q, J=6.4 Hz, 2H), 3.20 (q, J=6.4 Hz, 2H), 1.68 (quint, J=7.2 Hz, 2H), 1.55 (quint, J=7.2 Hz, 2H), 1.43-1.33 (m, 2H); $^{13}$C NMR (100.5 MHz, DMSO-$d_6$) δ 156.2 (q, J=35.9 Hz), 154.4, 150.6, 147.8, 138.4, 124.1, 119.3, 116.0 (q, J=288.2 Hz), 113.3, 108.7, 98.7, 55.7, 54.9, 42.4, 28.4, 27.4, 23.8; $^{19}$F NMR (376 MHz, DMSO-$d_6$) δ−74.4 (s, 3F); ESI-HRMS m/z: $[M+H]^+$ calcd for $C_{17}H_{21}F_3N_3O_2$, 356.1580, found 356.1570.

Example 12

Inhibiting PFKFB4 Activity by Formula (VIII) (Also Referred to as FBR1-12):

The efficacy of the compound Formula (VIII) in inhibiting the activity of the PFKFB4 enzyme was tested by examination of the effect of Formula (VIII) on the kinase activity of recombinant PFKFB4 enzyme in the ADP-Glo assay. FIG. 10 shows that Formula (VIII) inhibited the kinase activity of the PFKFB4 enzyme, and thereby indicating its ability to decrease the production of F26BP by PFKFB4.

Method: The efficacy of Formula (VIII) in inhibition of the kinase activity of the PFKFB4 enzyme was examined by exposing recombinant human PFKFB4 protein to Formula (VIII) in the ADP-Glo kinase assay (Promega) which measures ADP formed through a kinase reaction. Briefly, recombinant protein, ATP, substrate and Formula (VIII) were incubated together for the kinase reaction followed by the addition of ADP-Glo reagent, used to terminate the kinase reaction. Lastly, a kinase detection reagent was added to convert the newly formed ADP to ATP which was measured by a luciferase reaction. Data are shown in FIG. 10 as the decrease in luminescence caused by Formula (VIII) relative to DMSO.

Decrease in Cell Proliferation by Formula (VIII) (Also Referred to as FBR1-12):

The effect of increasing concentrations of Formula (VIII) on the proliferation of human cancer cells was examined in vitro. FIG. 11 shows that Formula (VIII) decreases the proliferation of human cancer cell lines in vitro with higher potency than 5MPN (5-[(8-methoxyquinolin-4-yl)amino] pentyl nitrate). Data in FIG. 11 are shown as the decrease in cell counts relative to the DMSO (vehicle) control.

Method: Cells were plated in 24 well plates and exposed to increasing concentrations of Formula (VIII). DMSO was used as a vehicle. After 24, 48 and 72 hours of exposure, cells were detached, and viable cells were counted by Trypan blue exclusion (representative counts at 48 hours shown).

Decrease in Fructose-2,6-Bisphosphate (F26BP) in Cells by Formula (VIII) (Also Referred to as FBR1-12):

The ability of Formula (VIII) to inhibit the activity of the PFKFB4 enzyme in cells was measured by examining the effect of the inhibitor on the levels of the product of the PFKFB4 enzyme, fructose-2,6-bisphosphate (F26BP). FIG. 12A and FIG. 12B (two independently run experiments) show that Formula (VIII) has a dose-dependent decrease in F26BP in cancer cells. Data in FIG. 12 are shown as the concentration of intracellular F26BP normalized to cellular protein concentration.

Method: In order to measure F26BP, cells were exposed to increasing concentrations of Formula (VIII) and were harvested, washed with PBS, lysed in NaOH/Tris acetate by heating at 80° C. and lysates neutralized to pH 7.2. F26BP content was measured using a coupled enzyme reaction following a modified method of Van Schaftingen (VAN SCHAFTINGEN et al, "A kinetic study of pyrophosphate: fructose-6-phosphate phosphotransferase from potato tubers. Application to a microassay of fructose 2,6-bisphosphate" Eur J Biochem. (1982) Vol. 129, No. 1, pp. 191-195), which is herein incorporated by reference in its entirety. The F26BP concentration was normalized to total cellular protein measured by the bicinchoninic acid assay (BCA, Thermo Scientific).

Decrease in Glycolysis in Cells by Formula (VIII) (Also Referred to as FBR1-12):

The effect of Formula (VIII) on the glycolytic pathway was examined to determine the ability of this inhibitor to decrease glycolysis secondary to its effect on PFKFB4-driven F26BP production. PFKFB4 produces F26BP which activates a rate-limiting enzyme of the glycolytic pathway, 6-phosphofructo-2-kinase (PFK-1). FIG. 13A and FIG. 13B (two independently run experiments) show that Formula (VIII) caused a dose-dependent decrease in glycolysis in cancer cells measured by the production of tritiated $H_2O$ ($^3H_2O$) in glycolysis through the enzyme enolase from 5-[$^3$H]glucose added to the medium. Data in FIG. 13A and FIG. 13B are shown as the production of $^3H_2O$ by Formula (VIII) relative to DMSO and normalized to protein concentration.

Method: To examine glycolysis, cells growing in 6-well plates were incubated in 500 µl of complete medium containing 1 µCi of 5-[$^3$H] glucose per well for 60 min in 5% $CO_2$ at 37° C. The medium was then collected and centrifuged to pellet any suspended cells. To separate the $^3H_2O$ formed via glycolysis from the 5-[$^3$H]glucose added to the medium, an evaporation technique in a sealed system was utilized. Briefly, 150 µl aliquots of medium were added to open tubes that were placed upright inside scintillation vials containing 1 ml of $H_2O$. The scintillation vials were sealed, and the $^3H_2O$ produced by glycolysis through enolase and released to the medium was allowed to equilibrate with the $H_2O$ in the outer vial for 48 h at 37° C. The amounts of $^3H_2O$ that had diffused into the surrounding $H_2O$ was measured on a Tri-Carb 2910 liquid scintillation analyzer (Perkin Elmer) and compared with $^3H_2O$ and 5-[$^3$H]glucose standards. Protein concentration was determined using the BCA assay and counts were normalized to protein concentration (previously described in CHESNEY et al., "Fructose-2,6-bisphosphate synthesis by 6-phosphofructo-2-kinase/fructose-2,6-bisphosphatase 4 (PFKFB4) is required for the glycolytic response to hypoxia and tumor growth" Oncotarget (2014) Vol. 5, No. 16, pp. 6670-6686, which is herein incorporated by reference in its entirety).

Decrease in ATP Production in Cells by Formula (VIII) (Also Referred to as FBR1-12):

The effect of Formula (VIII) on the production of ATP was examined as a measure of its effect on energy production by the glycolytic pathway. FIG. 14A and FIG. 14B (two independently run experiments) show that Formula (VIII) caused a dose-dependent decrease in the production of ATP by cancer cells.

Method: To measure ATP, cells were washed (while still adherent) with cold PBS, lysed with Passive Lysis Buffer (Molecular Probes, Invitrogen) added directly to the plates, and immediately harvested by scraping. The lysates were flash frozen (to −80° C.) and thawed (to 37° C.) once to accomplish complete lysis and then centrifuged to clear the lysates. Intracellular ATP levels were determined using a bioluminescence assay (Molecular Probes), utilizing luciferase and its substrate, D-luciferin and ATP values were calculated using an ATP standard curve. The ATP concentration was normalized to protein concentration that was estimated using the BCA assay.

Decrease in Anchorage Independent Growth in Cells by Formula (VIII) (Also Referred to as FBR1-12):

We examined the ability of Formula (VIII) to inhibit the anchorage independent growth of cancer cells in vitro as colonies in soft agar. Anchorage independent growth is an in-vitro surrogate for tumor growth and we found that Formula (VIII) inhibited the growth of cancer cells as soft agar colonies. Representative images are shown in FIG. 15A, and colonies formed were enumerated. The number of colonies formed in the presence of Formula (VIII) was compared with those formed in the presence of the vehicle, DMSO (FIG. 15B).

Method: Cancer cells were plated in soft agar and the effects of increasing concentrations of Formula (VIII) on anchorage independent growth was examined. Briefly, a feeder layer of 0.6% agarose (Agar Noble, Becton Dickinson) in RPMI with 10% fetal bovine serum was plated in 6 cm plates containing vehicle (DMSO) or increasing concentrations of Formula (VIII). $1 \times 10^4$ cells were re-suspended in 0.3% agarose in RPMI/10% serum containing DMSO or increasing concentrations of Formula (VIII) and plated on top of the feeder layer. Cells were allowed to grow at 37° C. in 5% $CO_2$ and agarose-containing media with DMSO+/−Formula (VIII) was replenished every 5 days until colonies became visible. Colonies were stained with MTT [3-(4,5-dimethylthiazol-2-yl)-2,5-diphenyl tetrazolium bromide] and counted in four random 1 $cm^2$ areas per plate under 40× magnification and enumerated.

Pharmacokinetic Profile of Formula (VIII) (Also Referred to as FBR1-12):

The pharmacokinetic profile of Formula (VIII) was determined in mice following IV and oral administration of Formula (VIII) (FIG. 16).

Method: The pharmacokinetic profile of Formula (VIII) was determined in male CD-1 mice dosed orally and IV with Formula (VIII)/Nine time points (n=3 per time point) were used to determine indicated PK parameters calculated using WinNonLin v5.0. Plasma samples were extracted using acetonitrile and analyzed by LC/MS-MS using a Waters XSELECT CSH C18 2.5 micron 50×2.1 mm column eluted with a biphasic mobile phase (0.1% formic acid in acetonitrile and water).

Formula (VIII) (Also Referred to as FBR1-12) Decreased the Growth of Tumors In Vivo:

The efficacy of Formula (VIII) in decreasing the growth of tumors in vivo was examined. Mice were implanted with Lewis lung carcinoma cells and after tumors were noted, dosed daily with DMSO±Formula (VIII) by gavage and tumor growth followed. FIG. 17 shows that oral Formula (VIII) administration decreased established tumor growth in a syngeneic mouse tumor model. Data shown as mean±SEM for each timepoint.

Method: C57BL/6 mice (Charles River) were implanted with $1 \times 10^6$ Lewis lung carcinoma cells subcutaneously and, after tumors developed, were followed by caliper measurements daily to quantify tumor mass using the formula: tumor mass=(length×width$^2$)/2. When tumors were ~150-200 mg, mice were randomized to daily oral DMSO±Formula (VIII) (n=10/group) at 40 mg/kg in 50 µL DMSO and tumor growth followed×9 days. (* signifies statistical significance)

Formula (VIII) (Also Referred to as FBR1-12) Decreased Tumor Glucose Uptake in Tumors In Vivo:

The efficacy of Formula (VIII) to decrease tumor glucose uptake was examined by positron emission tomography (PET) following $^{18}$F-fluoro-2-deoxy-glucose (FDG) injection. FIG. 18 shows that Formula (VIII) administration caused a decrease in tumor FDG uptake compared with vehicle.

Method: FDG-PET was conducted on tumor-bearing mice to determine acute effects of Formula (VIII) on glucose uptake. C57BL/6 mice (Charles River) with subcutaneous Lewis lung carcinoma tumors were injected intraperitoneally with 100 µCi of $^{18}$F-fluoro-2-deoxy-glucose under isoflurane anesthesia and subjected to a 15-minute static scan 45 minutes after tracer injection at baseline. Twenty-four hours later, the same animals were administered vehicle (DMSO) or Formula (VIII) (in DMSO, 40 mg/kg, POx1), and, after 60 minutes, FDG uptake determined by PET scan. Tumor/cerebellum ROI (regions of interest) were quantified, representative sagittal cuts from mice are shown with arrows showing the tumors on the animals. (* signifies statistical significance).

Example 13

FIG. 19A.

The efficacy of the compounds FB4-32 and FB4-35 in specifically inhibiting the activity of the PFKFB4 enzyme was tested by examination of their effect on the kinase activity of recombinant PFKFB4 enzyme in the ADP-Glo assay. Both compounds inhibited the kinase activity of the PFKFB4 enzyme thereby indicating their ability to decrease the production of fructose-2,6-bisphosphate (F26BP) by PFKFB4.

Method: The efficacy of FB4-32 and FB4-35 in inhibition of the kinase activity of the PFKFB4 enzyme was examined by exposing recombinant human PFKFB4 protein to FB4-32 and FB4-35 in the ADP-Glo kinase assay (Promega) which measures ADP formed through a kinase reaction. Briefly, recombinant protein, ATP, substrate and FB4-32 or FB4-35 were incubated together for the kinase reaction followed by the addition of ADP-Glo reagent to terminate the kinase reaction. Last, a kinase detection reagent was added to convert the newly formed ADP to ATP which was measured by a luciferase reaction. Data are shown as the decrease in luminescence caused by FB4-32 and FB4-35 relative to DMSO.

FIG. 19B.

The ability of FB4-32 and FB4-35 to inhibit the activity of the PFKFB4 enzyme in H460 cells was measured by examining the effect of FB4-32 or FB4-35 on the production of the product of the PFKFB4 enzyme, F26BP (effects at 2.5 µM are shown). We found that FB4-32 and FB4-35 caused a decrease in F26BP in human lung cancer cells (H460). Data are shown as the concentration of intracellular F26BP normalized to cellular protein concentration.

Method: In order to measure F26BP, H460 cells were exposed to increasing concentrations of the agents and were harvested, washed with PBS, lysed in NaOH/Tris acetate by heating at 80° C. and lysates neutralized to pH 7.2. F26BP content was measured using a coupled enzyme reaction following a modified method of Van Schaftingen et al. (Eur J Biochem. 1982; 129(1):191-195). The F26BP concentration was normalized to total cellular protein measured by the bicinchoninic acid assay (BCA, Thermo Scientific).

FIG. 19C.

The effect of FB4-32 and FB4-35 on the glycolytic pathway was examined to determine their ability to decrease glycolysis secondary to their effects on PFKFB4-driven F26BP production. PFKFB4 produces F26BP which activates a key rate-limiting enzyme of the glycolytic pathway, 6-phosphofructo-2-kinase (PFK-1). Both compounds caused a dose-dependent decrease in glycolysis in lung cancer cells (H460) measured by the production of tritiated $H_2O$ ($^3H_2O$) in glycolysis through the enzyme enolase from 5-[$^3H$] glucose added to the medium. Data are shown as the decrease in production of $^3H_2O$ by FB4-32 and FB4-35 relative to DMSO and normalized to protein concentration.

Method: To examine glycolysis, H460 cells growing in 6-well plates were incubated in 500 µl of complete medium containing 1 µCi of 5-[$^3H$] glucose per well for 60 min in 5% $CO_2$ at 37° C. The medium was then collected and centrifuged to pellet any suspended cells. To separate the $^3H_2O$ formed via glycolysis from the 5-[$^3H$]glucose added to the medium, an evaporation technique in a sealed system was utilized. Briefly, 150 µl aliquots of medium were added to open tubes that were placed upright inside scintillation vials containing 1 ml of $H_2O$. The scintillation vials were sealed, and the $^3H_2O$ produced by glycolysis through enolase and released to the medium was allowed to equilibrate with the $H_2O$ in the outer vial for 48 h at 37° C. The amounts of $^3H_2O$ that had diffused into the surrounding $H_2O$ was measured on a Tri-Carb 2910 liquid scintillation analyzer (Perkin Elmer) and compared with $^3H_2O$ and 5-[$^3H$]glucose standards. Protein concentration was determined using the BCA assay and counts were normalized to protein concentration (previously described in CHESNEY et al. Oncotarget. 2014; 5(16):6670-6686.)

FIG. 19D.

The effect of increasing concentrations of the several compounds including FB4-32 and FB4-35 on the proliferation of human lung cancer cells (H460) was examined in vitro. FB4-32 and FB4-35 decreased the proliferation of H460 cells in vitro with higher potency than 5MPN. Data are shown as the decrease in cell counts relative to the DMSO (vehicle) control.

Method: H460 cells were plated in 24 well plates and exposed to increasing concentrations of FB4-31 to FB4-36 and 5MPN. DMSO was used as a vehicle. After 24, 48 and 72 hours of exposure, cells were detached, and viable cells were counted by Trypan blue exclusion (representative counts at 72 hours shown).

Example 14

FIG. 20.

The pharmacokinetic profile of FB4-32 was determined in mice following IV and oral administration of FB4-32. FB4-32 was found to have oral bioavailability.

Method: The pharmacokinetic profile of FB4-32 was determined in mice dosed orally and IV with FB4-32. Nine time points (n=3 per time point) were used to determine indicated PK parameters calculated using WinNonLin v5.0. Plasma samples were extracted using acetonitrile and analyzed by LC/MS-MS using a PhenomexSynergi Polar-RP 4 micron 50×2.0 mm column eluted with a biphasic mobile phase (0.5% formic acid in acetonitrile and water).

Example 15

General Experimental:

All commercially purchased chemicals and solvents were used without further purification. All reactions were conducted under a nitrogen atmosphere in flame dried glassware. Reactions were monitored by thin-layer chromatography (TLC) on silica gel plates (Analtech, Uniplates GHLF, 0.25 mm with UV254) and were visualized with UV light (254 nm and 360 nm) or potassium permanganate stain. Isolated compounds were purified via flash chromatography on a Teledyne Isco Combiflash $R_f$ with prepacked silica gel columns eluted with an optimal gradient as described. All NMR spectra were recorded on an Agilent 400 MR spectrometer equipped with an OneProbe at 400 MHz for $^1H$, 376 MHz for $^{19}F$ and 100 MHz for $^{13}C$. Chemical shifts were recorded as δ values in parts per million (ppm) at 25° C. and either tetramethylsilane (TMS) or residue solvent was used as an internal standard. Coupling constants are reported in hertz (Hz) and splitting patterns are designated as s, singlet; d, doublet; t, triplet; q, quartet; quint, quintet; m, multiplet; br, broad. Analytical purity was determined by reverse-phase high-performance liquid chromatography (RP-HPLC) on an Agilent 1260 infinity equipped with a diode array (160-450 nm). The instrument was equipped with an Agilent Zobrax Extend C-18 column (1.8 m, 2.1×50 mm) with mobile phase consisting of mass spectrophotometry grade water (with 0.1% formic acid and 0.1% methanol) and acetonitrile (with 0.1% formic acid). The RP-HPLC method employed a linear gradient from 5%-100% acetonitrile at 0.3 mL/min over 15 mins with 4 mL injection volume. High-resolution MS were recorded on an Agilent 6224 time-of-flight detector connected to the HPLC system that utilized electrospray ionization.

Commercial Sources for Some Chemicals:

4-Chloro-8-methoxyquinoline: MilliporeSigma (order number: BBO0000177-1G). Alternatively, we also synthesized 4-Chloro-8-methoxyquinoline according to a modified procedure based on GHOSH et al., "Discovery of 4-(4-(2-((5-Hydroxy-1,2,3,4-tetrahydronaphthalen-2-yl)(propyl)amino)ethyl)piperazin-1-yl)quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease." *J. Med. Chem.* 2010, 53, 2114-2125.

1,5-diaminopentane: TCI America (order number: D0108)

ethyl trifluoroacetate: Oakwood Chemical (order number: 001179).

1,6-diaminohexane: Alfa Aesar (order number: A14212)

Bromoacetyl bromide: Alfa Aesar (order number: A19580)

trifluoromethanesulfonic anhydride: Beantown Chemical (order number: 214265-5G)

methyl difluoroacetate: Oakwood Chemical (order number: 006791)

1,4-diaminobutane: Alfa Aesar (order number: B21316)

4-chloroquinoline: Ark Pharm, Inc. (order number: AK-28421)

Anhydrous ethanol was purchased from MilliporeSigma and used without further purification.

Dichloromethane, chloroform and methanol was HPLC grade or better and was purchased from Thermo Fisher Scientific.

Scheme 1. Preparation of FB4-31.

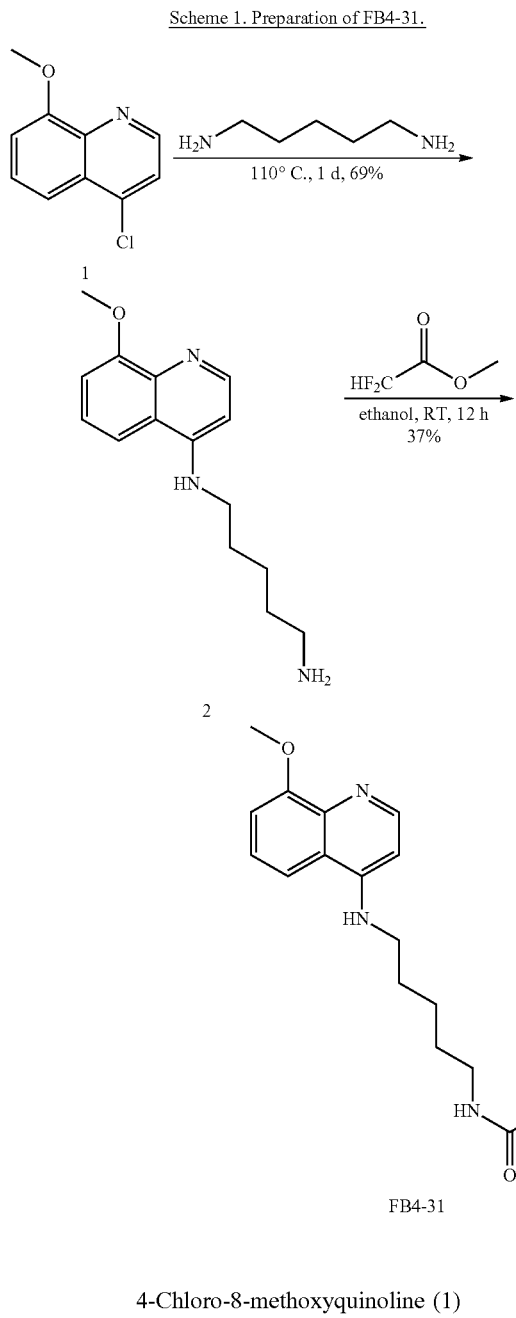

4-Chloro-8-methoxyquinoline (1)

Quinoline 1 is commercially available or can be prepared in three steps from 2-methoxyaniline by a modified literature procedure (as discussed above).

$N^1$-(8-Methoxyquinolin-4-yl)pentane-1,5-diamine (2)

A solution of 1.25 g (6.46 mmol) of quinoline 1 in 2.0 mL of 1,5-diaminopentane was stirred at 110° C. for 24 hours. After cooling to room temperature, the solution was poured into 150 mL of ice water and then extracted three times with 150-mL portions of $CH_2Cl_2$. The combined organic layers were washed with water and brine, dried ($Na_2SO_4$) and concentrated in vacuo. The crude solid was chromatographed over silica gel (eluted with $CH_2Cl_2 \rightarrow 50\%$ MeOH) to afford 1.15 g (69%) of 2 as a tan solid. Alternatively, the crude product can be purified by partially dissolving in ethyl acetate, sonicate for 5 mins and collect the solid by filtration to afford semi pure product that is suitable for further use: $^1$H NMR (400 MHz, DMSO-$d_6$) δ 8.32 (d, J=5.2 Hz, 1H), 7.73 (dd, J=8.4, 0.8 Hz, 1H), 7.30 (td, J=8.4, 0.8 Hz, 1H), 7.05 (dd, J=8.0, 0.8 Hz, 1H), 6.99 (s, br, 1H), 6.44 (d, J=5.2 Hz, 1H), 3.88 (s, 3H), 3.23 (t, J=6.8 Hz, 2H), 2.54 (t, J=6.4 Hz, 2H), 1.65 (quint, J=7.2 Hz, 2H), 1.47-1.33 (m, 4H); $^{13}$C NMR (100.5 MHz, DMSO-$d_6$) δ 155.4, 149.7, 149.1, 140.2, 123.6, 119.6, 113.2, 108.0, 98.6, 55.5, 42.5, 41.5, 32.9, 27.8, 24.1. ESI-HRMS m/z: $[M+H]^+$ calcd for $C_{15}H_{22}N_3O$, 260.1757, found 260.1758.

2,2-Difluoro-N-(5-((8-methoxyquinolin-4-yl)amino) pentyl)acetamide (FB4-31)

To a solution of 50 mg (0.19 mmol) of amine 2 in 2 mL of anhydrous ethanol was added 18 µL (23 mg, 0.21 mmol) of methyl difluoroacetate. The resulting solution stirred for 12 hours at room temperature and then was concentrated in vacuo. The crude product was chromatographed over silica gel (eluted with $CH_2Cl_2 \rightarrow 35\%$ MeOH) to afford 24 mg (37%) of FB4-31 as a light brown solid: $^1$H NMR (400 MHz, DMSO-$d_6$) δ 8.78 (t, br, J=5.6 Hz, 1H), 8.32 (d, J=5.6 Hz, 1H), 7.73 (dd, J=8.8, 1.2 Hz, 1H), 7.30 (t, J=8.4 Hz, 1H), 7.05 (dd, J=7.6, 0.8 Hz, 1H), 6.98 (t, br, J=5.2 Hz, 1H), 6.45 (d, J=1.2 Hz, 1H), 6.19 (t, $J_{H,F}$=54 Hz, 1H), 3.88 (s, 3H), 3.23 (q, J=6.8 Hz, 2H), 3.16 (q, J=6.8 Hz, 2H), 1.67 (quint, J=7.2 Hz, 2H), 1.52 (quint, J=7.2 Hz, 2H), 1.43-1.33 (m, 2H); $^{13}$C NMR (100.5 MHz, DMSO-$d_6$) δ 162.0 (t, J=25.0 Hz), 155.4, 149.7, 149.0, 140.1, 123.7, 119.6, 113.1, 108.6 (t, J=246.5 Hz), 108.0, 98.7, 55.5, 42.3, 38.4, 28.3, 27.4, 23.9; $^{19}$F NMR (376 MHz, DMSO-$d_6$) δ –125.6 (s, 1F), –125.8 (s, 1F); ESI-HRMS m/z: $[M+H]^+$ calcd for $C_{17}H_{22}F_2N_3O_2$, 338.1675, found 338.1684.

Scheme 2. Preparation of FB4-35.

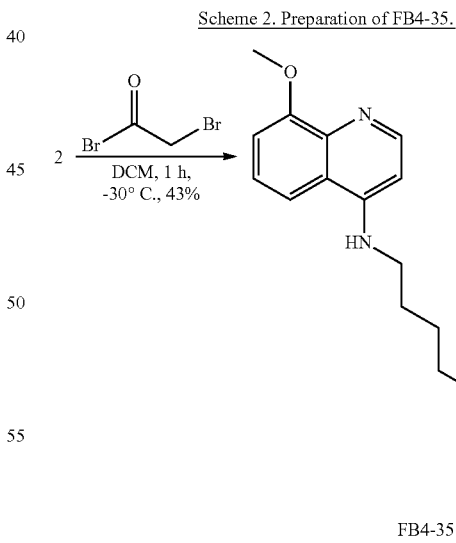

2-Bromo-N-(5-((8-methoxyquinolin-4-yl)amino) pentyl)acetamide (FB4-35)

To a solution of 50 mg (0.19 mmol) of amine 2 in 5 mL of dichloromethane was added at –30° C. dropwise 8 µL (19 mg, 0.096 mmol) of bromoacetyl bromide. After stirring for 1 h at −30° C., the mixture was concentrated in vacuo and the residue was chromatographed over silica gel (eluted with CH$_2$Cl$_2$→10% MeOH) to afford 16 mg (43%) of FB4-35 as an off-white solid: $^1$H NMR (400 MHz, DMSO-d$_6$) δ 8.56 (s, br, 1H), 8.32 (d, J=6.4 Hz, 1H), 8.27 (t, br, J=5.6 Hz, 1H), 7.95 (d, J=8.4 Hz, 1H), 7.55 (t, J=8.4 Hz, 1H), 7.39 (d, J=8.0 Hz, 1H), 6.76 (d, J=6.8 Hz, 1H), 4.02 (s, 3H), 3.81 (s, 2H), 3.38 (q, J=7.2 Hz, 2H), 3.09 (q, J=6.4 Hz, 2H), 1.69 (quint, J=7.2 Hz, 2H), 1.54-1.32 (m, 4H); ESI-HRMS m/z: [M+H]$^+$ calcd for C$_{17}$H$_{23}$BrN$_3$O$_2$, 380.0968, found 380.0983.

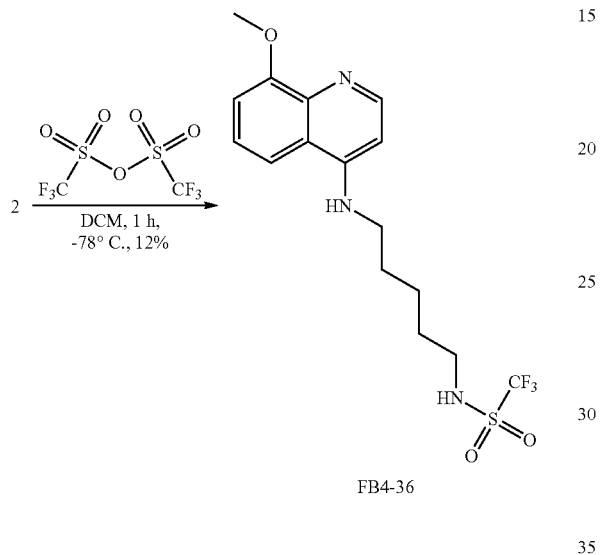

Scheme 3. Synthesis of FB4-36.

1,1,1-Trifluoro-N-(5-((8-methoxyquinolin-4-yl)amino)pentyl)methanesulfonamide (FB4-36)

To a solution of 75 mg (0.29 mmol) of amine 2 in 2 mL of dichloromethane was added dropwise at −78° C. a solution of 24 μL (41 mg, 0.14 mmol) of trifluoromethanesulfonic anhydride in 1 mL of dichloromethane. After stirring for 1 h at −78° C., the mixture was concentrated in vacuo and the residue was chromatographed over silica gel (eluted with CH$_2$Cl$_2$→20% MeOH) to afford 14 mg (12%) of FB4-36 as an light brown solid that contains residual trifluoromethanesulfonic acid: $^1$H NMR (400 MHz, DMSO-d$_6$) δ 8.99 (s, br, 1H), 8.31 (d, J=7.2 Hz, 1H), 7.99 (dd, J=8.4, 0.8 Hz, 1H), 7.63 (t, J=8.4 Hz, 1H), 7.49 (d, J=7.2 Hz, 1H), 6.85 (d, J=7.2 Hz, 1H), 4.07 (s, 3H), 3.49 (q, J=6.8 Hz, 2H), 3.15 (t, J=7.2 Hz, 2H), 1.69 (quint, J=7.2 Hz, 2H), 1.56 (quint, J=7.2 Hz, 2H), 1.46-1.38 (m, 2H); $^{13}$C NMR (100.5 MHz, DMSO-d$_6$) δ 155.0, 149.6, 142.1 (2C), 126.6, 117.5, 113.9, 112.1, 98.6, 56.6, 43.3, 42.9, 29.3, 27.0, 23.1; $^{19}$F NMR (376 MHz, DMSO-d$_6$) δ−77.4 (s, 3F); ESI-HRMS m/z: [M+H]$^+$ calcd for C$_{16}$H$_{21}$F3N$_3$O$_3$S, 392.1250, found 392.1248.

Scheme 4. Synthesis of FB4-32

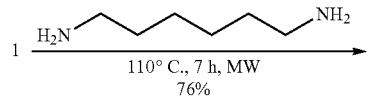

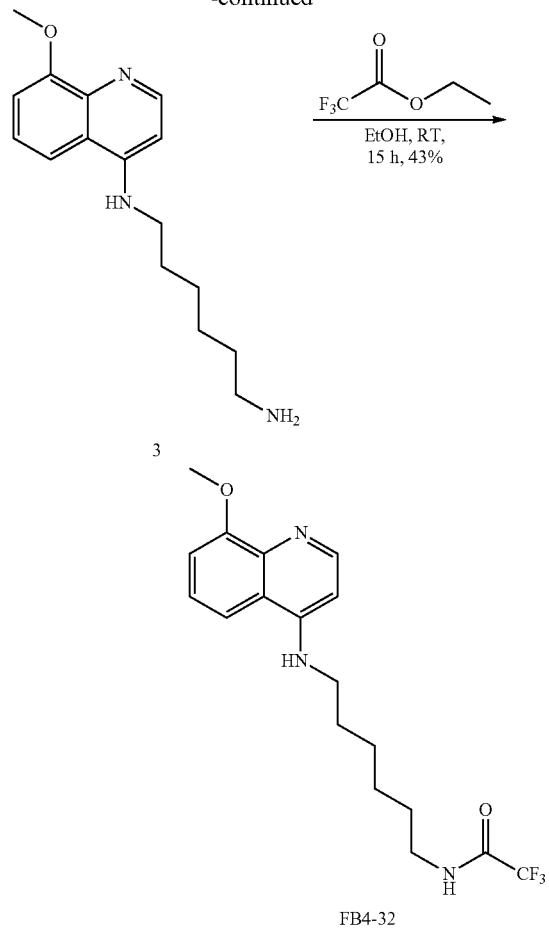

N$^1$-(8-Methoxyquinolin-4-yl)hexane-1,6-diamine (3)

A solution of 70 mg (0.36 mmol) of quinoline 1 in 0.4 mL of 1,6-diaminohexane was stirred at 110° C. for 7 hours via microwave irradiation. After cooling to room temperature, the solution was poured into 150 mL of ice water and then extracted three times with 150-mL portions of CH$_2$Cl$_2$. The combined organic layers were washed with water and brine, dried (Na$_2$SO$_4$) and concentrated in vacuo. The crude product was chromatographed over silica gel (eluted with CH$_2$Cl$_2$→50% MeOH) to afford 75 mg (76%) of 3 as a semi pure, tan oil that was suitable for use without further purification: ESI-HRMS m/z: [M+H]$^+$ calcd for C$_{16}$H$_{24}$N$_3$O, 274.1914, found 274.1914.

2,2,2-Trifluoro-N-(6-((8-methoxyquinolin-4-yl)amino)hexyl)acetamide (FB4-32)

To a solution of 70 mg (0.26 mmol) of amine 3 in 4 mL of anhydrous ethanol was added 50 μL (60 mg, 0.42 mmol) of ethyl trifluoroacetate. The resulting solution stirred for 15 hours at room temperature and then was concentrated in vacuo. The crude product was chromatographed over silica gel (eluted with CH$_2$Cl$_2$→35% MeOH) to afford 41 mg (43%) of FB4-32 as a light brown solid: $^1$H NMR (400 MHz, DMSO-d$_6$) δ 9.42 (t, br, J=6.0 Hz, 1H), 8.31 (d, J=6.0 Hz, 1H), 7.84 (dd, J=8.8, 1.2 Hz, 1H), 7.77 (s, br, 1H), 7.42 (td, J=8.4, 0.8 Hz, 1H), 7.21 (dd, J=8.0, 1.2 Hz, 1H), 6.59 (d, J=5.6 Hz, 1H), 3.95 (s, 3H), 3.33 (q, J=6.8 Hz, 2H), 3.18 (q, J=6.8 Hz, 2H), 1.66 (quint, J=7.2 Hz, 2H), 1.50 (quint, J=7.2 Hz, 2H), 1.44-1.27 (m, 4H); $^{13}$C NMR (100.5 MHz, DMSO-d$_6$) δ 157.1 (q, J=35.2 Hz), 154.2, 152.6, 147.4, 125.7, 116.9 (q, J=288.4 Hz), 119.8, 114.4, 110.5, 99.6, 56.8 (2C), 43.5, 29.1, 28.6, 27.1, 26.9; $^{19}$F NMR (376 MHz, DMSO-d$_6$) δ-74.4 (s, 3F); ESI-HRMS m/z: [M+H]$^+$ calcd for C$_{18}$H$_{23}$F3N$_3$O$_2$ 370.1737, found 370.1745.

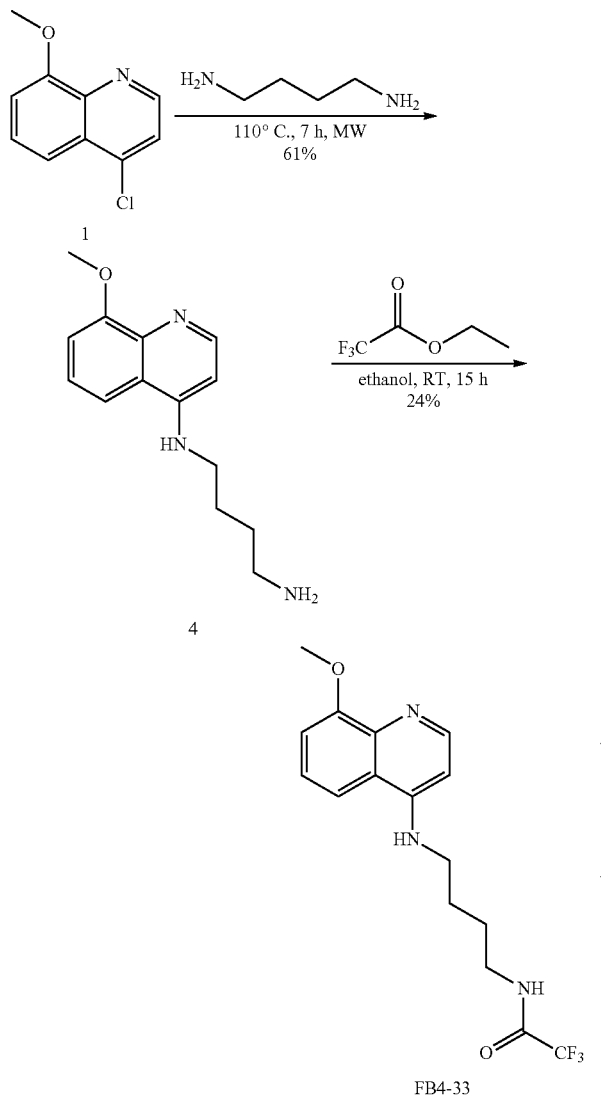

4

N$^1$-(8-Methoxyquinolin-4-yl)butane-1,4-diamine (4)

A solution of 70 mg (0.36 mmol) of quinoline 1 in 0.3 mL of 1,4-diaminobutane was stirred at 110° C. for 7 hours via microwave irradiation. After cooling to room temperature, residual diamine was partially removed by azeotropic distillation with 50 mL portions of chloroform (3 times) and drying under high vacuum. The residue was chromatographed over silica gel (eluted with CH$_2$Cl2→50% MeOH) to afford 54 mg (61%) of 4 as a semi pure, tan oil that was suitable for use without further purification:

ESI-HRMS m/z: [M+H]$^+$ calcd for C$_{14}$H$_{20}$N$_3$O, 246.1601, found 246.1601.

2,2,2-Trifluoro-N-(4-((8-methoxyquinolin-4-yl)amino)butyl)acetamide (FB4-33)

To a solution of 50 mg (0.20 mmol) of amine 4 in 3 mL of anhydrous ethanol was added 49 L (58 mg, 0.41 mmol) of ethyl trifluoroacetate. The resulting solution stirred for 15 hours at room temperature and then was concentrated in vacuo. The crude product was chromatographed over silica gel (eluted with CH$_2$Cl$_2$→35% MeOH) to afford 17 mg (24%) of FB4-33 as a light brown solid: $^1$H NMR (400 MHz, DMSO-d$_6$) δ 9.44 (s, br, 1H), 8.32 (d, J=5.2 Hz, 1H), 7.72 (dd, J=8.8, 1.2 Hz, 1H), 7.30 (dd, J=8.4, 8.0 Hz, 1H), 7.05 (dd, J=7.6, 0.8 Hz, 1H), 7.01 (t, br, J=5.6 Hz, 1H), 6.46 (d, J=5.2 Hz, 1H), 3.88 (s, 3H), 3.30-3.19 (m, 4H), 1.70-1.55 (m, 4H); $^{13}$C NMR (100.5 MHz, DMSO-d$_6$) δ 156.2 (q, J=35.7 Hz), 155.4, 149.7, 149.1, 140.2, 123.7, 119.6, 116.0 (q, J=288.2 Hz), 113.1, 108.0, 98.7, 55.5, 41.9, 39.0, 26.0, 25.1; $^{19}$F NMR (376 MHz, DMSO-d$_6$) δ-74.4 (s, 3F); ESI-HRMS m/z: [M+H]$^+$ calcd for C$_{16}$H$_{19}$F$_3$N$_3$O$_2$ 342.1424, found 342.1425.

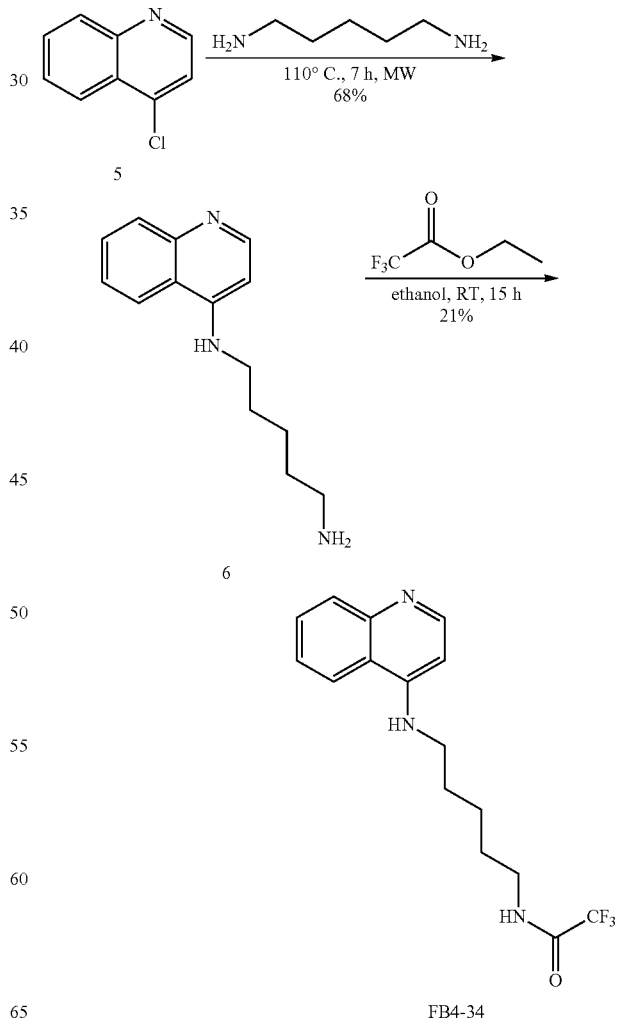

N$^1$-(Quinolin-4-yl)pentane-1,5-diamine (6)

A solution of 150 mg (0.917 mmol) of commercially available quinoline 5 in 0.3 mL of 1,5-diaminopentane was stirred at 110° C. for 7 hours via microwave irradiation. After cooling to room temperature, residual diamine was partially removed by azeotropic distillation with 50 mL portions of chloroform (3 times) and drying under high vacuum. The residue was chromatographed over silica gel (eluted with CH$_2$Cl$_2$→50% MeOH) to afford 142 mg (68%) of 6 as a semi pure, tan oil that was suitable for use without further purification: ESI-HRMS m/z: [M+H]$^+$ calcd for C$_{14}$H$_{20}$N$_3$, 230.1652, found 230.1655.

2,2,2-Trifluoro-N-(5-(quinolin-4-ylamino)pentyl) acetamide (FB4-34)

To a solution of 65 mg (0.28 mmol) of amine 6 in 2 mL of anhydrous ethanol was added 37 µL (44 mg, 0.31 mmol) of ethyl trifluoroacetate. The resulting solution stirred for 15 hours at room temperature and then was concentrated in vacuo. The crude product was chromatographed over silica gel (eluted with CH$_2$Cl$_2$→35% MeOH) to afford 19 mg (21%) of FB4-34 as a light brown solid: $^1$H NMR (400 MHz, DMSO-d$_6$) δ 9.42 (s, br, 1H), 8.37 (d, J=5.6 Hz, 1H), 8.21 (dd, J=8.4, 1.6 Hz, 1H), 7.76 (dd, J=8.4, 1.2 Hz, 1H), 7.60 (ddd, J=8.3, 6.8, 1.2 Hz, 1H), 7.40 (ddd, J=8.4, 6.8, 1.6 Hz, 1H), 7.18 (t, br, J=5.6 Hz, 1H), 6.44 (d, J=5.6 Hz, 1H), 3.26 (q, J=7.2 Hz, 2H), 3.20 (q, J=6.8 Hz, 2H), 1.68 (quint, J=7.2 Hz, 2H), 1.55 (quint, J=6.8 Hz, 2H), 1.43-1.35 (m, 2H); $^{13}$C NMR (100.5 MHz, DMSO-d$_6$) δ 156.2 (q, J=35.9 Hz), 150.4, 150.1, 147.9, 128.8, 128.7, 123.8, 121.7, 118.8, 116.0 (q, J=288.2 Hz), 98.1, 54.9, 42.3, 28.0, 27.4, 23.8; $^{19}$F NMR (376 MHz, DMSO-d$_6$) δ−74.4 (s, 3F); ESI-HRMS m/z: [M+H]$^+$ calcd for C$_{16}$H$_{19}$F$_3$N$_3$O, 326.1475, found 326.1471.

Example 16

Additional Embodiments

Embodiment 1

A method of treating cancer in a subject in need of treatment thereof, the method comprising administering to the subject an effective amount of a compound having the Formula (I):

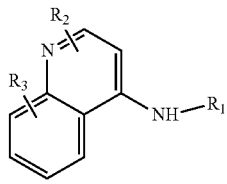

wherein:
R$^1$ is a C$_1$-C$_5$ alkyl nitrooxy;
R$_2$ can be present or absent, and when present is a C$_1$-C$_5$ alkyl;
R$_3$ can be present or absent, and when present is a C$_1$-C$_5$ alkoxy; and
wherein if R$_2$ is present and located on the nitrogen of the quinoline group, said nitrogen has a positive charge.

Embodiment 2

The method of embodiment 1, wherein the compound of Formula (I) is administered at a dosage effective for specifically inhibiting 6-phosphofructo-2-kinase/fructose-2,6-bisphophatase 4 (PFKFB4).

Embodiment 3

The method of embodiment 1, wherein the compound of Formula (I) is administered orally.

Embodiment 4

The method of embodiment 1, wherein the compound of Formula (I) is administered intravenously.

Embodiment 5

The method of embodiment 1, wherein the subject is substantially free of signs of toxicity.

Embodiment 6

The method of embodiment 1, wherein the subject is a mammal.

Embodiment 7

The method of embodiment 1, wherein the cancer is selected from breast cancer, lung cancer, colon cancer, and prostate cancer.

Embodiment 8

The method of embodiment 1, further comprising administering to the subject one or more additional therapeutic compounds.

Embodiment 9

The method of embodiment 9, wherein the one or more additional therapeutic compounds comprises one or more of a PFKFB3 inhibitor, a PFKFB2 inhibitor, and a PFKFB1 inhibitor.

Embodiment 10

A method of inhibiting PFKFB4 in a cell, the method comprising contacting the cell with an effective amount of a compound having the Formula (I):

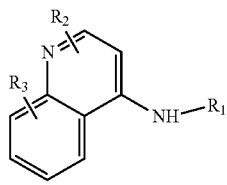

wherein:
R$_1$ is a C$_1$-C$_5$ alkyl nitrooxy;
R$_2$ can be present or absent, and when present is a C$_1$-C$_5$ alkyl;

$R_3$ can be present or absent, and when present is a $C_1$-$C_5$ alkoxy; and wherein if $R_2$ is present and located on the nitrogen of the quinoline group, said nitrogen has a positive charge.

Embodiment 11

The method of embodiment 10, wherein PFKFB4 is specifically inhibited.

Embodiment 12

The method of embodiment 10, wherein the cell is a mammalian cell.

Embodiment 13

The method of embodiment 10, wherein the cell is a cancer cell.

Embodiment 14

The method of embodiment 10, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 15

A method of inhibiting PFKFB4 in a subject, the method comprising administering to the subject an effective amount of a compound having the Formula (I):

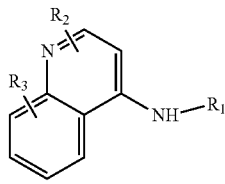

(I)

wherein:
$R^1$ is a $C_1$-$C_5$ alkyl nitrooxy;
$R_2$ can be present or absent, and when present is a $C_1$-$C_5$ alkyl;
$R_3$ can be present or absent, and when present is a $C_1$-$C_5$ alkoxy; and
wherein if $R_2$ is present and located on the nitrogen of the quinoline group, said nitrogen has a positive charge.

Embodiment 16

The method of embodiment 15, wherein the compound of Formula (I) is administered at a dosage effective for specifically inhibiting PFKFB4.

Embodiment 17

The method of embodiment 15, wherein the compound of Formula (I) is administered orally.

Embodiment 18

The method of embodiment 15, wherein the compound of Formula (I) is administered intravenously.

Embodiment 19

The method of embodiment 15, wherein the subject remains substantially free of signs of toxicity.

Embodiment 20

A method of reducing glycolytic flux in a cell, the method comprising contacting the cell with an effective amount of a compound having the Formula (I):

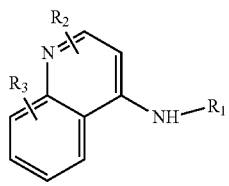

(I)

wherein:
$R_1$ is a $C_1$-$C_5$ alkyl nitrooxy;
$R_2$ can be present or absent, and when present is a $C_1$-$C_5$ alkyl;
$R_3$ can be present or absent, and when present is a $C_1$-$C_5$ alkoxy; and
wherein if $R_2$ is present and located on the nitrogen of the quinoline group, said nitrogen has a positive charge.

Embodiment 21

The method of embodiment 20, wherein the cell is a mammalian cell.

Embodiment 22

The method of embodiment 20, wherein the cell is a cancer cell.

Embodiment 23

The method of embodiment 20, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 24

A method of reducing proliferative capacity of a cell, the method comprising contacting the cell with an effective amount of a compound having the Formula (I):

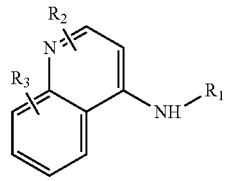

(I)

wherein:
$R_1$ is a $C_1$-$C_5$ alkyl nitrooxy;
$R_2$ can be present or absent, and when present is a $C_1$-$C_5$ alkyl;

Embodiment 25

The method of embodiment 24, wherein the cell is contacted with the compound of Formula (I) at a dosage effective for specifically inhibiting PFKFB4.

Embodiment 26

The method of embodiment 24, wherein the cell is a mammalian cell.

Embodiment 27

The method of embodiment 24, wherein the cell is a cancer cell.

Embodiment 28

The method of embodiment 24, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 29

A method of reducing fructose-2,6-bisphosphate (F2,6BP) in a cell, the method comprising contacting the cell with an effective amount of a compound having the Formula (I):

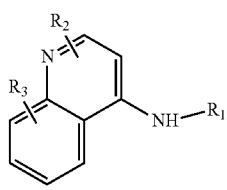

(I)

wherein:
$R_1$ is a $C_1$-$C_5$ alkyl nitrooxy;
$R_2$ can be present or absent, and when present is a $C_1$-$C_5$ alkyl;
$R_3$ can be present or absent, and when present is a $C_1$-$C_5$ alkoxy; and
wherein if $R_2$ is present and located on the nitrogen of the quinoline group, said nitrogen has a positive charge.

Embodiment 30

The method of embodiment 29, wherein the cell is a mammalian cell.

Embodiment 31

The method of embodiment 29, wherein the cell is a cancer cell.

Embodiment 32

A pharmaceutical composition comprising an effective amount of a compound having the Formula (I):

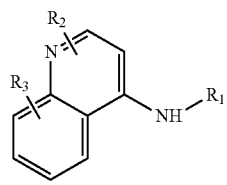

(I)

wherein:
$R_1$ is a $C_1$-$C_5$ alkyl nitrooxy;
$R_2$ can be present or absent, and when present is a $C_1$-$C_5$ alkyl;
$R_3$ can be present or absent, and when present is a $C_1$-$C_5$ alkoxy;
wherein if $R_2$ is present and located on the nitrogen of the quinoline group, said nitrogen has a positive charge;
and at least one pharmaceutical excipient.

Embodiment 33

The pharmaceutical composition of embodiment 32, wherein an effective amount of the compound of Formula (I) is an amount that specifically inhibits PFKFB4.

Embodiment 34

The pharmaceutical composition of embodiment 32, wherein the pharmaceutical composition is formulated for oral administration.

Embodiment 35

The pharmaceutical composition of embodiment 32, wherein the pharmaceutical composition is formulated for intravenous administration.

Embodiment 36

The pharmaceutical composition of embodiment 32, further comprising one or more additional therapeutic agents.

Embodiment 37

A method of treating cancer in a subject in need of treatment thereof, the method comprising administering to the subject an effective amount of a compound having the Formula (II):

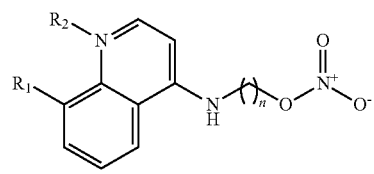

(II)

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge.

Embodiment 38

The method of embodiment 37, wherein the compound of Formula (II) is administered at a dosage effective for specifically inhibiting 6-phosphofructo-2-kinase/fructose-2,6-bisphophatase 4 (PFKFB4).

Embodiment 39

The method of embodiment 37, wherein the compound of Formula (II) is administered orally.

Embodiment 40

The method of embodiment 37, wherein the compound of Formula (II) is administered intravenously.

Embodiment 41

The method of embodiment 37, wherein the subject is substantially free of signs of toxicity.

Embodiment 42

The method of embodiment 37, wherein the subject is a mammal.

Embodiment 43

The method of embodiment 37, wherein the cancer is selected from breast cancer, lung cancer, colon cancer, and prostate cancer.

Embodiment 44

The method of embodiment 37, further comprising administering to the subject one or more additional therapeutic compounds.

Embodiment 45

The method of embodiment 44, wherein the one or more additional therapeutic compounds comprises one or more of a PFKFB3 inhibitor, a PFKFB2 inhibitor, and a PFKFB1 inhibitor.

Embodiment 46

A method of inhibiting PFKFB4 in a cell, the method comprising contacting the cell with an effective amount of a compound having the Formula (II):

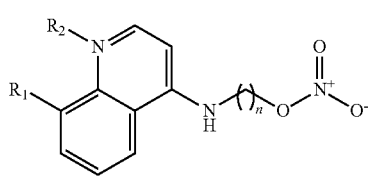

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge.

Embodiment 47

The method of embodiment 46, wherein PFKFB4 is specifically inhibited.

Embodiment 48

The method of embodiment 46, wherein the cell is a mammalian cell.

Embodiment 49

The method of embodiment 46, wherein the cell is a cancer cell.

Embodiment 50

The method of embodiment 46, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 51

A method of inhibiting PFKFB4 in a subject, the method comprising administering to the subject an effective amount of a compound having the Formula (II):

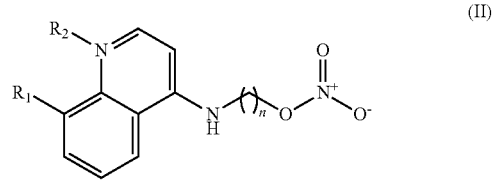

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge.

Embodiment 52

The method of embodiment 51, wherein the compound of Formula (II) is administered at a dosage effective for specifically inhibiting PFKFB4.

Embodiment 53

The method of embodiment 51, wherein the compound of Formula (II) is administered orally.

Embodiment 54

The method of embodiment 51, wherein the compound of Formula (II) is administered intravenously.

Embodiment 55

The method of embodiment 51, wherein the subject remains substantially free of signs of toxicity.

Embodiment 56

A method of reducing glycolytic flux in a cell, the method comprising contacting the cell with an effective amount of a compound having the Formula (II):

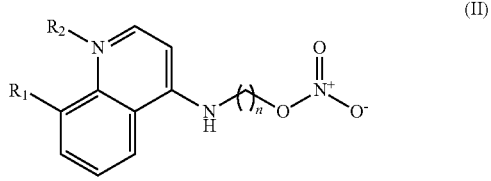

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge.

Embodiment 57

The method of embodiment 56, wherein the cell is a mammalian cell.

Embodiment 58

The method of embodiment 56, wherein the cell is a cancer cell.

Embodiment 59

The method of embodiment 56, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 60

A method of reducing proliferative capacity of a cell, the method comprising contacting the cell with an effective amount of a compound having the Formula (II):

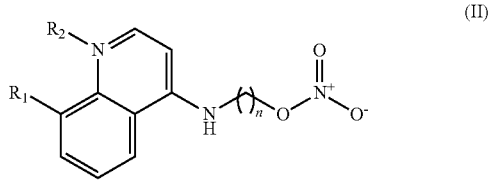

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge.

Embodiment 61

The method of embodiment 61, wherein the cell is contacted with the compound of Formula (II) at a dosage effective for specifically inhibiting PFKFB4.

Embodiment 62

The method of embodiment 61, wherein the cell is a mammalian cell.

Embodiment 63

The method of embodiment 61, wherein the cell is a cancer cell.

Embodiment 64

The method of embodiment 61, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 65

A method of reducing fructose-2,6-bisphosphate (F2,6BP) in a cell, the method comprising contacting the cell with an effective amount of a compound having the Formula (II):

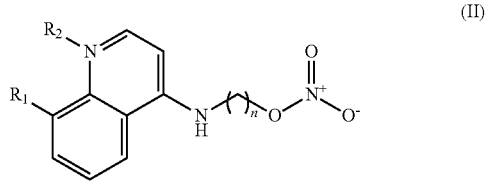

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge.

Embodiment 66

The method of embodiment 65, wherein the cell is a mammalian cell.

Embodiment 67

The method of embodiment 65, wherein the cell is a cancer cell.

Embodiment 68

A pharmaceutical composition comprising an effective amount of a compound having the Formula (II):

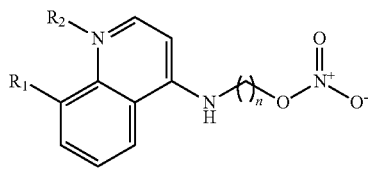

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge;
and at least one pharmaceutical excipient.

Embodiment 69

The pharmaceutical composition of embodiment 68, wherein an effective amount of the compound of Formula (II) is an amount that specifically inhibits PFKFB4.

Embodiment 70

The pharmaceutical composition of embodiment 68, wherein the pharmaceutical composition is formulated for oral administration.

Embodiment 71

The pharmaceutical composition of embodiment 68, wherein the pharmaceutical composition is formulated for intravenous administration.

Embodiment 72

A method of treating cancer in a subject in need of treatment thereof, the method comprising administering to the subject an effective amount of a compound having the Formula (III):

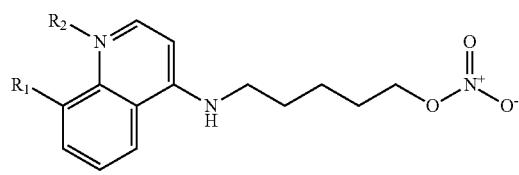

wherein:
$R_1$ can be present or absent, and when present is a $C_1$-$C_5$ alkoxy;
$R_2$ can be present or absent, and when present is a $C_1$-$C_5$ alkyl; and
wherein if $R_2$ is present, the nitrogen of the quinoline group has a positive charge.

Embodiment 73

The method of embodiment 72, wherein the compound of Formula (III) is administered at a dosage effective for specifically inhibiting 6-phosphofructo-2-kinase/fructose-2, 6-bisphophatase 4 (PFKFB4).

Embodiment 74

The method of embodiment 72, wherein the compound of Formula (III) is administered orally.

Embodiment 75

The method of embodiment 72, wherein the compound of Formula (III) is administered intravenously.

Embodiment 76

The method of embodiment 72, wherein the subject is substantially free of signs of toxicity.

Embodiment 77

The method of embodiment 72, wherein the subject is a mammal.

Embodiment 78

The method of embodiment 72, wherein the cancer is selected from breast cancer, lung cancer, colon cancer, and prostate cancer.

Embodiment 79

The method of embodiment 72, further comprising administering to the subject one or more additional therapeutic compounds.

Embodiment 80

The method of embodiment 79, wherein the one or more additional therapeutic compounds comprises one or more of a PFKFB3 inhibitor, a PFKFB2 inhibitor, and a PFKFB1 inhibitor.

Embodiment 81

A method of inhibiting PFKFB4 in a cell, the method comprising contacting the cell with an effective amount of a compound having the Formula (III):

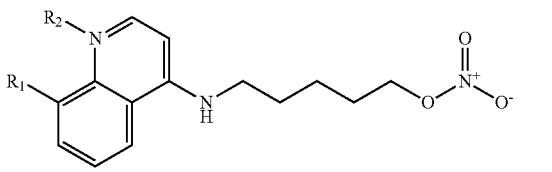

wherein:
$R_1$ can be present or absent, and when present is a $C_1$-$C_5$ alkoxy;
$R_2$ can be present or absent, and when present is a $C_1$-$C_5$ alkyl; and wherein if $R_2$ is present, the nitrogen of the quinoline group has a positive charge.

Embodiment 82

The method of embodiment 81, wherein PFKFB4 is specifically inhibited.

Embodiment 83

The method of embodiment 81, wherein the cell is a mammalian cell.

Embodiment 84

The method of embodiment 81, wherein the cell is a cancer cell.

Embodiment 85

The method of embodiment 81, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 86

A method of inhibiting PFKFB4 in a subject, the method comprising administering to the subject an effective amount of a compound having the Formula (III):

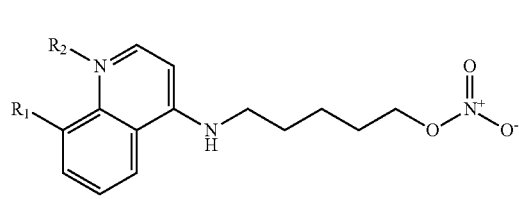

wherein:
$R_1$ can be present or absent, and when present is a $C_1$-$C_5$ alkoxy;
$R_2$ can be present or absent, and when present is a $C_1$-$C_5$ alkyl; and
wherein if $R_2$ is present, the nitrogen of the quinoline group has a positive charge.

Embodiment 87

The method of embodiment 86, wherein the compound of Formula (III) is administered at a dosage effective for specifically inhibiting PFKFB4.

Embodiment 88

The method of embodiment 86, wherein the compound of Formula (III) is administered orally.

Embodiment 89

The method of embodiment 86, wherein the compound of Formula (III) is administered intravenously.

Embodiment 90

The method of embodiment 86, wherein the subject remains substantially free of signs of toxicity.

Embodiment 91

A method of reducing glycolytic flux in a cell, the method comprising contacting the cell with an effective amount of the compound having the Formula (III):

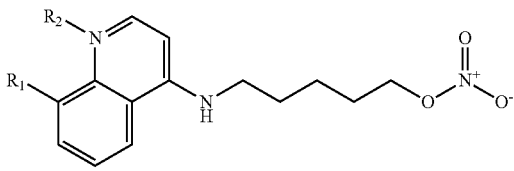

wherein:
$R_1$ can be present or absent, and when present is a $C_1$-$C_5$ alkoxy;
$R_2$ can be present or absent, and when present is a $C_1$-$C_5$ alkyl; and
wherein if $R_2$ is present, the nitrogen of the quinoline group has a positive charge.

Embodiment 92

The method of embodiment 91, wherein the cell is a mammalian cell.

Embodiment 93

The method of embodiment 91, wherein the cell is a cancer cell.

Embodiment 94

The method of embodiment 91, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 95

A method of reducing proliferative capacity of a cell, the method comprising contacting the cell with an effective amount of a compound having the Formula (III):

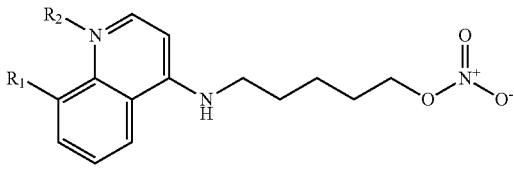

wherein:
$R_1$ can be present or absent, and when present is a $C_1$-$C_5$ alkoxy;
$R_2$ can be present or absent, and when present is a $C_1$-$C_5$ alkyl; and wherein if $R_2$ is present, the nitrogen of the quinoline group has a positive charge.

Embodiment 96

The method of embodiment 95, wherein the cell is contacted with the compound of Formula (III) at a dosage effective for specifically inhibiting PFKFB4.

Embodiment 97

The method of embodiment 95, wherein the cell is a mammalian cell.

Embodiment 98

The method of embodiment 95, wherein the cell is a cancer cell.

Embodiment 99

The method of embodiment 95, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 100

A method of reducing fructose-2,6-bisphosphate (F2,6BP) in a cell, the method comprising contacting the cell with an effective amount of a compound having the Formula (III):

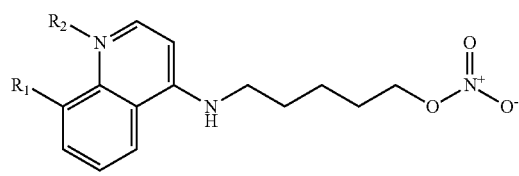

(III)

wherein:
$R_1$ can be present or absent, and when present is a $C_1$-$C_5$ alkoxy;
$R_2$ can be present or absent, and when present is a $C_1$-$C_5$ alkyl; and
wherein if $R_2$ is present, the nitrogen of the quinoline group has a positive charge.

Embodiment 101

The method of embodiment 100, wherein the cell is a mammalian cell.

Embodiment 102

The method of embodiment 100, wherein the cell is a cancer cell.

Embodiment 103

A pharmaceutical composition comprising an effective amount of a compound having the Formula (III):

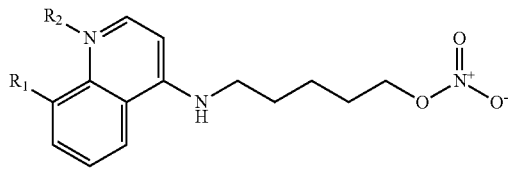

(III)

wherein:
$R_1$ can be present or absent, and when present is a $C_1$-$C_5$ alkoxy;
$R_2$ can be present or absent, and when present is a $C_1$-$C_5$ alkyl; and
wherein if $R_2$ is present, the nitrogen of the quinoline group has a positive charge;
and at least one pharmaceutical excipient.

Embodiment 104

The pharmaceutical composition of embodiment 103, wherein an effective amount of the compound of Formula (III) is an amount that specifically inhibits PFKFB4.

Embodiment 105

The pharmaceutical composition of embodiment 103, wherein the pharmaceutical composition is formulated for oral administration.

Embodiment 106

The pharmaceutical composition of embodiment 103, wherein the pharmaceutical composition is formulated for intravenous administration.

Embodiment 107

A method of treating cancer in a subject in need of treatment thereof, the method comprising administering to the subject an effective amount of 5-[(8-methoxyquinolin-4-yl)amino]pentyl nitrate (5MPN).

Embodiment 108

The method of embodiment 107, wherein 5MPN is administered at a dosage effective for specifically inhibiting 6-phosphofructo-2-kinase/fructose-2,6-bisphophatase 4 (PFKFB4).

Embodiment 109

The method of embodiment 107, wherein 5MPN is administered orally.

Embodiment 110

The method of embodiment 107, wherein the 5MPN is administered intravenously.

Embodiment 111

The method of embodiment 107, wherein the subject is substantially free of signs of toxicity.

Embodiment 112

The method of embodiment 107, wherein the subject is a mammal.

Embodiment 113

The method of embodiment 107, wherein the cancer is selected from breast cancer, lung cancer, colon cancer, and prostate cancer.

Embodiment 114

The method of embodiment 107, further comprising administering to the subject one or more additional therapeutic compounds.

Embodiment 115

The method of embodiment 114, wherein the one or more additional therapeutic compounds comprises one or more of a PFKFB3 inhibitor, a PFKFB2 inhibitor, and a PFKFB1 inhibitor.

Embodiment 116

A method of inhibiting PFKFB4 in a cell, the method comprising contacting the cell with an effective amount of 5MPN.

Embodiment 117

The method of embodiment 116, wherein PFKFB4 is specifically inhibited.

Embodiment 118

The method of embodiment 116, wherein the cell is a mammalian cell.

Embodiment 119

The method of embodiment 116, wherein the cell is a cancer cell.

Embodiment 120

The method of embodiment 116, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 121

A method of inhibiting PFKFB4 in a subject, the method comprising administering to the subject an effective amount of 5MPN.

Embodiment 122

The method of embodiment 121, wherein 5MPN is administered at a dosage effective for specifically inhibiting PFKFB4.

Embodiment 123

The method of embodiment 121, wherein 5MPN is administered orally.

Embodiment 124

The method of embodiment 121, wherein the 5MPN is administered intravenously.

Embodiment 125

The method of embodiment 121, wherein the subject remains substantially free of signs of toxicity.

Embodiment 126

A method of reducing glycolytic flux in a cell, the method comprising contacting the cell with an effective amount of 5MPN.

Embodiment 127

The method of embodiment 126, wherein the cell is a mammalian cell.

Embodiment 128

The method of embodiment 126, wherein the cell is a cancer cell.

Embodiment 129

The method of embodiment 126, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 130

A method of reducing proliferative capacity of a cell, the method comprising contacting the cell with an effective amount of 5MPN.

Embodiment 131

The method of embodiment 130, wherein the cell is contacted with 5MPN at a dosage effective for specifically inhibiting PFKFB4.

Embodiment 132

The method of embodiment 130, wherein the cell is a mammalian cell.

Embodiment 133

The method of embodiment 130, wherein the cell is a cancer cell.

Embodiment 134

The method of embodiment 130, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 135

A method of reducing fructose-2,6-bisphosphate (F2, 6BP) in a cell, the method comprising contacting the cell with an effective amount of 5MPN.

Embodiment 136

The method of embodiment 135, wherein the cell is a mammalian cell.

Embodiment 137

The method of embodiment 135, wherein the cell is a cancer cell.

Embodiment 138

A pharmaceutical composition comprising an effective amount of 5MPN, and at least one pharmaceutical excipient.

Embodiment 139

The pharmaceutical composition of embodiment 138, wherein an effective amount of 5MPN is an amount that specifically inhibits PFKFB4.

Embodiment 140

The pharmaceutical composition of embodiment 138, wherein the pharmaceutical composition is formulated for oral administration.

Embodiment 141

The pharmaceutical composition of embodiment 138, wherein the pharmaceutical composition is formulated for intravenous administration.

Embodiment 142

The pharmaceutical composition of embodiment 138, further comprising one or more additional therapeutic agents.

Embodiment 143

A method of treating cancer in a subject in need of treatment thereof, the method comprising administering to the subject an effective amount of 5-[(8-methoxy-2-methylquinolin-1-ium-4-yl)amino]pentyl nitrate (MPN-2).

Embodiment 144

The method of embodiment 143, wherein MPN-2 is administered at a dosage effective for specifically inhibiting 6-phosphofructo-2-kinase/fructose-2,6-bisphophatase 4 (PFKFB4).

Embodiment 145

The method of embodiment 143, wherein MPN-2 is administered orally.

Embodiment 146

The method of embodiment 143, wherein the MPN-2 is administered intravenously.

Embodiment 147

The method of embodiment 143, wherein the subject is substantially free of signs of toxicity.

Embodiment 148

The method of embodiment 143, wherein the subject is a mammal.

Embodiment 149

The method of embodiment 143, wherein the cancer is selected from breast cancer, lung cancer, colon cancer, and prostate cancer.

Embodiment 150

The method of embodiment 143, further comprising administering to the subject one or more additional therapeutic compounds.

Embodiment 151

The method of embodiment 150, wherein the one or more additional therapeutic compounds comprises one or more of a PFKFB3 inhibitor, a PFKFB2 inhibitor, and a PFKFB1 inhibitor.

Embodiment 152

A method of inhibiting PFKFB4 in a cell, the method comprising contacting the cell with an effective amount of MPN-2.

Embodiment 153

The method of embodiment 152, wherein PFKFB4 is specifically inhibited.

Embodiment 154

The method of embodiment 152, wherein the cell is a mammalian cell.

Embodiment 155

The method of embodiment 152, wherein the cell is a cancer cell.

Embodiment 156

The method of embodiment 152, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 157

A method of inhibiting PFKFB4 in a subject, the method comprising administering to the subject an effective amount of MPN-2.

Embodiment 158

The method of embodiment 157, wherein MPN-2 is administered at a dosage effective for specifically inhibiting PFKFB4.

Embodiment 159

The method of embodiment 157, wherein MPN-2 is administered orally.

Embodiment 160

The method of embodiment 157, wherein the MPN-2 is administered intravenously.

Embodiment 161

The method of embodiment 157, wherein the subject remains substantially free of signs of toxicity.

Embodiment 162

A method of reducing glycolytic flux in a cell, the method comprising contacting the cell with an effective amount of MPN-2.

Embodiment 163

The method of embodiment 162, wherein the cell is a mammalian cell.

Embodiment 164

The method of embodiment 162, wherein the cell is a cancer cell.

Embodiment 165

The method of embodiment 162, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 166

A method of reducing proliferative capacity of a cell, the method comprising contacting the cell with an effective amount of MPN-2.

Embodiment 167

The method of embodiment 166, wherein the cell is contacted with MPN-2 at a dosage effective for specifically inhibiting PFKFB4.

Embodiment 168

The method of embodiment 166, wherein the cell is a mammalian cell.

Embodiment 169

The method of embodiment 166, wherein the cell is a cancer cell.

Embodiment 170

The method of embodiment 166, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 171

A method of reducing fructose-2,6-bisphosphate (F2, 6BP) in a cell, the method comprising contacting the cell with an effective amount of MPN-2.

Embodiment 172

The method of embodiment 171, wherein the cell is a mammalian cell.

Embodiment 173

The method of embodiment 171, wherein the cell is a cancer cell.

Embodiment 174

A pharmaceutical composition comprising an effective amount of MPN-2, and at least one pharmaceutical excipient.

Embodiment 175

The pharmaceutical composition of embodiment 174, wherein an effective amount of MPN-2 is an amount that specifically inhibits PFKFB4.

Embodiment 176

The pharmaceutical composition of embodiment 174, wherein the pharmaceutical composition is formulated for oral administration.

Embodiment 177

The pharmaceutical composition of embodiment 174, wherein the pharmaceutical composition is formulated for intravenous administration.

Embodiment 178

The pharmaceutical composition of embodiment 174, further comprising one or more additional therapeutic agents.

Embodiment 179

The pharmaceutical composition of embodiment 178, wherein the one or more additional therapeutic compounds comprises one or more of a PFKFB3 inhibitor, a PFKFB2 inhibitor, and a PFKFB1 inhibitor.

Embodiment 180

A method of treating cancer in a subject in need of treatment thereof, the method comprising administering to the subject an effective amount of a compound having the Formula (IV):

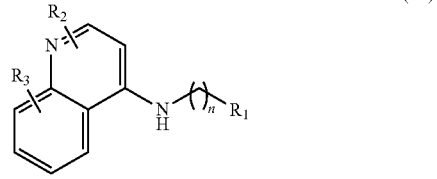

(IV)

wherein:

n is 1-6;

R$_1$ is carboxylic acid, methyl sulfamide, carboxylic acid methyl ester, hydroxide, nitrate, or tert-butyl carbamate;

R$_2$ can be present or absent, and when present is a C$_1$-C$_5$ alkyl;

R$_3$ can be present or absent, and when present is a C$_1$-C$_5$ alkoxy, cloride, or hydrogen; and wherein if R$_2$ is present and located on the nitrogen of the quinoline group, said nitrogen has a positive charge.

Embodiment 181

The method of embodiment 180, wherein the compound of Formula (IV) is administered at a dosage effective for specifically inhibiting 6-phosphofructo-2-kinase/fructose-2,6-bisphophatase 4 (PFKFB4).

Embodiment 182

The method of embodiment 180, wherein the compound of Formula (IV) is administered orally.

Embodiment 183

The method of embodiment 180, wherein the compound of Formula (IV) is administered intravenously.

Embodiment 184

The method of embodiment 180, wherein the subject is substantially free of signs of toxicity.

Embodiment 185

The method of embodiment 180, wherein the subject is a mammal.

Embodiment 186

The method of embodiment 180, wherein the cancer is selected from breast cancer, lung cancer, colon cancer, and prostate cancer.

Embodiment 187

The method of embodiment 180, further comprising administering to the subject one or more additional therapeutic compounds.

Embodiment 188

The method of embodiment 187, wherein the one or more additional therapeutic compounds comprises one or more of a PFKFB3 inhibitor, a PFKFB2 inhibitor, and a PFKFB1 inhibitor.

Embodiment 189

A method of inhibiting PFKFB4 in a cell, the method comprising contacting the cell with an effective amount of a compound having the Formula (IV):

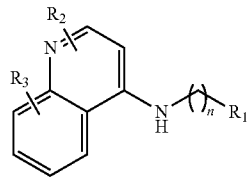
(IV)

wherein:

n is 1-6;

R$_1$ is carboxylic acid, methyl sulfamide, carboxylic acid methyl ester, hydroxide, nitrate, or tert-butyl carbamate;

R$_2$ can be present or absent, and when present is a C$_1$-C$_5$ alkyl;

R$_3$ can be present or absent, and when present is a C$_1$-C$_5$ alkoxy, cloride, or hydrogen; and wherein if R$_2$ is present and located on the nitrogen of the quinoline group, said nitrogen has a positive charge.

Embodiment 190

The method of embodiment 189, wherein PFKFB4 is specifically inhibited.

Embodiment 191

The method of embodiment 189, wherein the cell is a mammalian cell.

Embodiment 192

The method of embodiment 189, wherein the cell is a cancer cell.

Embodiment 193

The method of embodiment 189, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 194

A method of inhibiting PFKFB4 in a subject, the method comprising administering to the subject an effective amount of a compound having the Formula (IV):

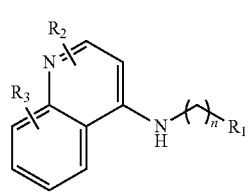
(IV)

wherein:

n is 1-6;

R$_1$ is carboxylic acid, methyl sulfamide, carboxylic acid methyl ester, hydroxide, nitrate, or tert-butyl carbamate;

R$_2$ can be present or absent, and when present is a C$_1$-C$_5$ alkyl;

R$_3$ can be present or absent, and when present is a C$_1$-C$_5$ alkoxy, cloride, or hydrogen; and wherein if $R_2$ is present and located on the nitrogen of the quinoline group, said nitrogen has a positive charge.

Embodiment 195

The method of embodiment 194, wherein the compound of Formula (IV) is administered at a dosage effective for specifically inhibiting PFKFB4.

Embodiment 196

The method of embodiment 194, wherein the compound of Formula (IV) is administered orally.

Embodiment 197

The method of embodiment 194, wherein the compound of Formula (IV) is administered intravenously.

Embodiment 198

The method of embodiment 194, wherein the subject remains substantially free of signs of toxicity.

Embodiment 199

A method of reducing glycolytic flux in a cell, the method comprising contacting the cell with an effective amount of the compound having the Formula (IV):

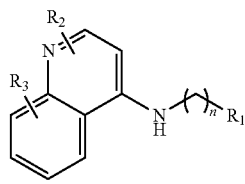

(IV)

wherein:
n is 1-6;
$R_1$ is carboxylic acid, methyl sulfamide, carboxylic acid methyl ester, hydroxide, nitrate, or tert-butyl carbamate;
$R_2$ can be present or absent, and when present is a $C_1$-$C_5$ alkyl;
$R_3$ can be present or absent, and when present is a $C_1$-$C_5$ alkoxy, cloride, or hydrogen; and
wherein if $R_2$ is present and located on the nitrogen of the quinoline group, said nitrogen has a positive charge.

Embodiment 200

The method of embodiment 199, wherein the cell is a mammalian cell.

Embodiment 201

The method of embodiment 199, wherein the cell is a cancer cell.

Embodiment 202

The method of embodiment 199, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 203

A method of reducing proliferative capacity of a cell, the method comprising contacting the cell with an effective amount of a compound having the Formula (IV):

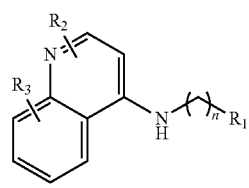

(IV)

wherein:
n is 1-6;
$R_1$ is carboxylic acid, methyl sulfamide, carboxylic acid methyl ester, hydroxide, nitrate, or tert-butyl carbamate;
$R_2$ can be present or absent, and when present is a $C_1$-$C_5$ alkyl;
$R_3$ can be present or absent, and when present is a $C_1$-$C_5$ alkoxy, cloride, or hydrogen; and
wherein if $R_2$ is present and located on the nitrogen of the quinoline group, said nitrogen has a positive charge.

Embodiment 204

The method of embodiment 203, wherein the cell is contacted with the compound of Formula (III) at a dosage effective for specifically inhibiting PFKFB4.

Embodiment 205

The method of embodiment 203, wherein the cell is a mammalian cell.

Embodiment 206

The method of embodiment 203, wherein the cell is a cancer cell.

Embodiment 207

The method of embodiment 203, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 208

A method of reducing fructose-2,6-bisphosphate (F2,6BP) in a cell, the method comprising contacting the cell with an effective amount of a compound having the Formula (IV):

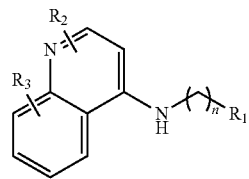

(IV)

wherein:

n is 1-6;

$R_1$ is carboxylic acid, methyl sulfamide, carboxylic acid methyl ester, hydroxide, nitrate, or tert-butyl carbamate;

$R_2$ can be present or absent, and when present is a $C_1$-$C_5$ alkyl;

$R_3$ can be present or absent, and when present is a $C_1$-$C_5$ alkoxy, cloride, or hydrogen; and wherein if $R_2$ is present and located on the nitrogen of the quinoline group, said nitrogen has a positive charge.

Embodiment 209

The method of embodiment 208, wherein the cell is a mammalian cell.

Embodiment 210

The method of embodiment 208, wherein the cell is a cancer cell.

Embodiment 211

A pharmaceutical composition comprising an effective amount of a compound having the Formula (IV)

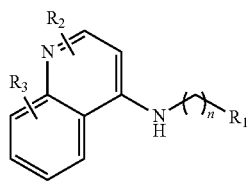

(IV)

wherein:

n is 1-6;

$R_1$ is carboxylic acid, methyl sulfamide, carboxylic acid methyl ester, hydroxide, nitrate, or tert-butyl carbamate;

$R_2$ can be present or absent, and when present is a $C_1$-$C_5$ alkyl;

$R_3$ can be present or absent, and when present is a $C_1$-$C_5$ alkoxy, cloride, or hydrogen; and wherein if $R_2$ is present and located on the nitrogen of the quinoline group, said nitrogen has a positive charge;

and at least one pharmaceutical excipient.

Embodiment 212

The pharmaceutical composition of embodiment 211, wherein an effective amount of the compound of Formula (IV) is an amount that specifically inhibits PFKFB4.

Embodiment 213

The pharmaceutical composition of embodiment 211, wherein the pharmaceutical composition is formulated for oral administration.

Embodiment 214

The pharmaceutical composition of embodiment 211, wherein the pharmaceutical composition is formulated for intravenous administration.

Embodiment 215

A method of treating cancer in a subject in need of treatment thereof, the method comprising administering to the subject an effective amount of a compound having the Formula (V):

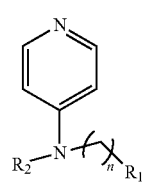

(V)

wherein:

n is 1-6;

$R_1$ nitrate; and $R_2$ is a hydrogen or nitrogen dioxide.

Embodiment 216

The method of embodiment 215, wherein the compound of Formula (V) is administered at a dosage effective for specifically inhibiting 6-phosphofructo-2-kinase/fructose-2, 6-bisphophatase 4 (PFKFB4).

Embodiment 217

The method of embodiment 215, wherein the compound of Formula (V) is administered orally.

Embodiment 218

The method of embodiment 215, wherein the compound of Formula (V) is administered intravenously.

Embodiment 219

The method of embodiment 215, wherein the subject is substantially free of signs of toxicity.

Embodiment 220

The method of embodiment 215, wherein the subject is a mammal.

Embodiment 221

The method of embodiment 215, wherein the cancer is selected from breast cancer, lung cancer, colon cancer, and prostate cancer.

Embodiment 222

The method of embodiment 215, further comprising administering to the subject one or more additional therapeutic compounds.

Embodiment 223

The method of embodiment 222, wherein the one or more additional therapeutic compounds comprises one or more of a PFKFB3 inhibitor, a PFKFB2 inhibitor, and a PFKFB1 inhibitor.

Embodiment 224

A method of inhibiting PFKFB4 in a cell, the method comprising contacting the cell with an effective amount of a compound having the Formula (V):

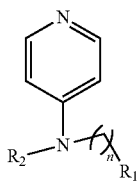

(V)

wherein:
n is 1-6;
$R_1$ nitrate; and
$R_2$ is a hydrogen or nitrogen dioxide.

Embodiment 225

The method of embodiment 224, wherein PFKFB4 is specifically inhibited.

Embodiment 226

The method of embodiment 224, wherein the cell is a mammalian cell.

Embodiment 227

The method of embodiment 224, wherein the cell is a cancer cell.

Embodiment 228

The method of embodiment 224, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 229

A method of inhibiting PFKFB4 in a subject, the method comprising administering to the subject an effective amount of a compound having the Formula (V):

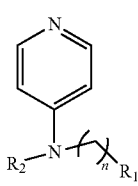

(V)

wherein:
n is 1-6;
$R_1$ nitrate; and
$R_2$ is a hydrogen or nitrogen dioxide.

Embodiment 230

The method of embodiment 229, wherein the compound of Formula (V) is administered at a dosage effective for specifically inhibiting PFKFB4.

Embodiment 231

The method of embodiment 229, wherein the compound of Formula (V) is administered orally.

Embodiment 232

The method of embodiment 229, wherein the compound of Formula (V) is administered intravenously.

Embodiment 233

The method of embodiment 229, wherein the subject remains substantially free of signs of toxicity.

Embodiment 234

A method of reducing glycolytic flux in a cell, the method comprising contacting the cell with an effective amount of the compound having the Formula (V):

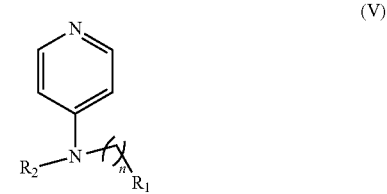

(V)

wherein:
n is 1-6;
$R_1$ nitrate; and
$R_2$ is a hydrogen or nitrogen dioxide.

Embodiment 235

The method of embodiment 234, wherein the cell is a mammalian cell.

Embodiment 236

The method of embodiment 234, wherein the cell is a cancer cell.

Embodiment 237

The method of embodiment 234, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 238

A method of reducing proliferative capacity of a cell, the method comprising contacting the cell with an effective amount of a compound having the Formula (V):

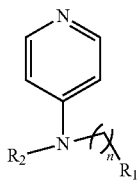

(V)

wherein:
n is 1-6;
R₁ nitrate; and
R₂ is a hydrogen or nitrogen dioxide.

Embodiment 239

The method of embodiment 238, wherein the cell is contacted with the compound of Formula (V) at a dosage effective for specifically inhibiting PFKFB4.

Embodiment 240

The method of embodiment 238, wherein the cell is a mammalian cell.

Embodiment 241

The method of embodiment 238, wherein the cell is a cancer cell.

Embodiment 242

The method of embodiment 238, wherein the cell is derived from a cell line comprising H460, H1299, H441, H522, DAOY, D283, SKBR3, JURKAT, B16F10, A549, MDA-MB-231, LNCaP, HCT116, or LLC cell lines.

Embodiment 243

A method of reducing fructose-2,6-bisphosphate (F2, 6BP) in a cell, the method comprising contacting the cell with an effective amount of a compound having the Formula (V):

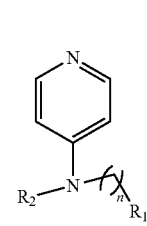

(V)

wherein:
n is 1-6;
R₁ nitrate; and
R₂ is a hydrogen or nitrogen dioxide.

Embodiment 244

The method of embodiment 243, wherein the cell is a mammalian cell.

Embodiment 245

The method of embodiment 243, wherein the cell is a cancer cell.

Embodiment 246

A pharmaceutical composition comprising an effective amount of a compound having the Formula (V):

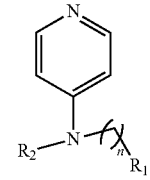

(V)

wherein:
n is 1-6;
R₁ nitrate; and
R₂ is a hydrogen or nitrogen dioxide;
and at least one pharmaceutical excipient.

Embodiment 247

The pharmaceutical composition of embodiment 246, wherein an effective amount of the compound of Formula (V) is an amount that specifically inhibits PFKFB4.

Embodiment 248

The pharmaceutical composition of embodiment 246, wherein the pharmaceutical composition is formulated for oral administration.

Embodiment 249

The pharmaceutical composition of embodiment 246, wherein the pharmaceutical composition is formulated for intravenous administration.

Embodiment 250

A compound having the Formula (IV):

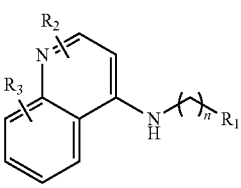

(IV)

wherein:
n is 1-6;
R₁ is carboxylic acid, methyl sulfamide, carboxylic acid methyl ester, hydroxide, nitrate, or tert-butyl carbamate;
R₂ can be present or absent, and when present is a $C_1$-$C_5$ alkyl;
R₃ can be present or absent, and when present is a $C_1$-$C_5$ alkoxy, cloride, or hydrogen; and wherein if R₂ is present and located on the nitrogen of the quinoline group, said nitrogen has a positive charge.
Embodiment 251
The compound of embodiment 250, wherein the compound of is selected from the group consisting of:
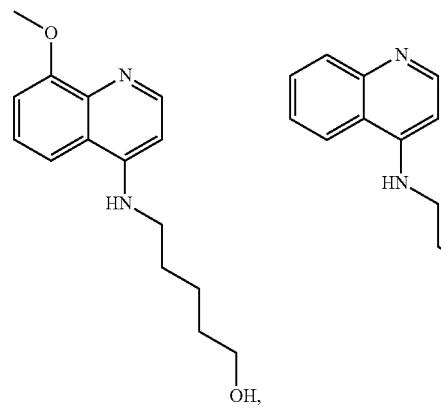
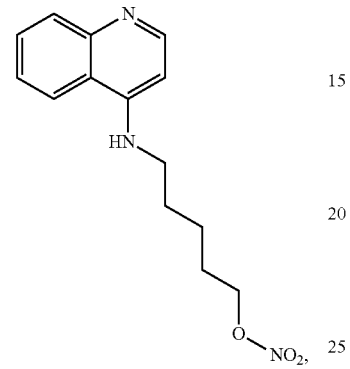
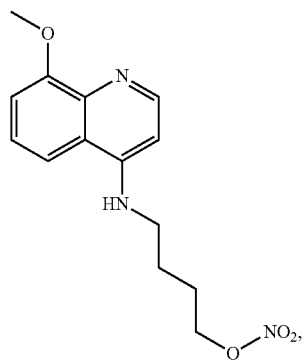
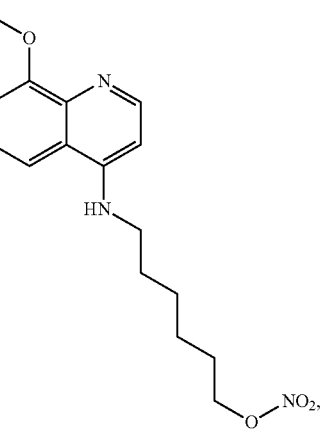
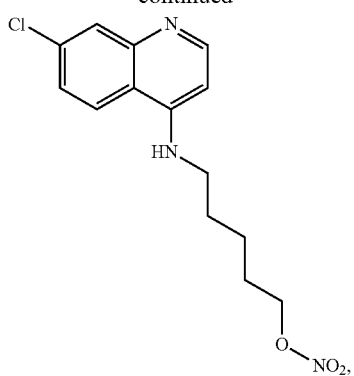
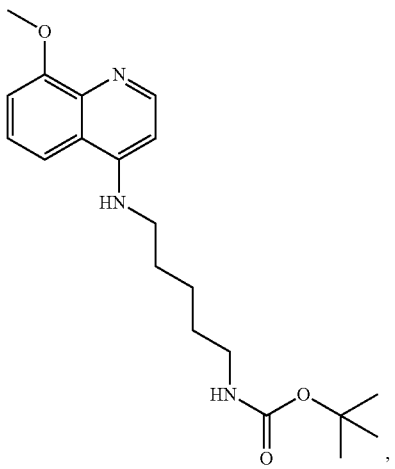

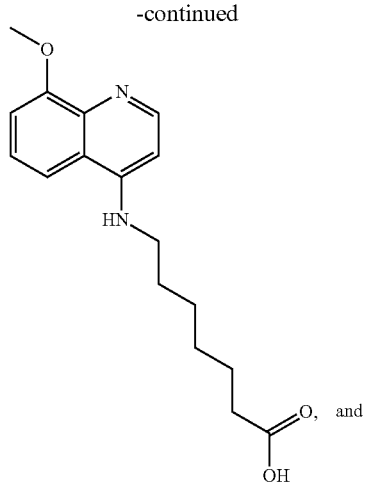
O, and
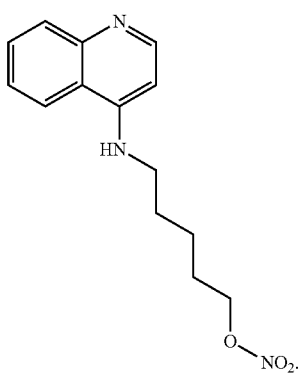 [SMILES: O=[N+]([O-])OCCCCCNc1ccnc2ccccc12]
Embodiment 254
The compound of embodiment 251, wherein the compound of is
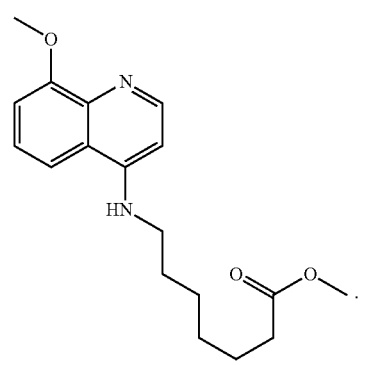
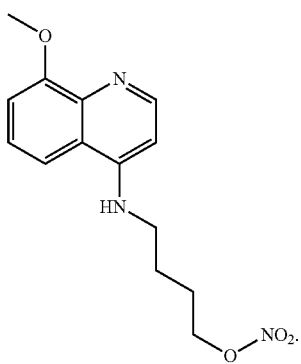 [SMILES: COc1cccc2c(NCCCCO[N+](=O)[O-])ccnc12]
Embodiment 252
Embodiment 255
The compound of embodiment 251, wherein the compound of is
The compound of embodiment 251, wherein the compound of is
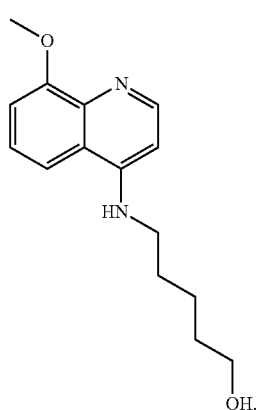 [SMILES: COc1cccc2c(NCCCCCO)ccnc12]
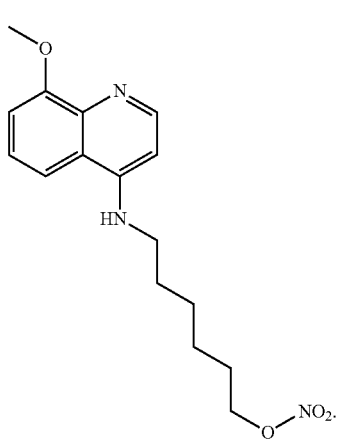 [SMILES: COc1cccc2c(NCCCCCCO[N+](=O)[O-])ccnc12]
Embodiment 253
Embodiment 256
The compound of embodiment 251, wherein the compound of is
The compound of embodiment 251, wherein the compound of is

Embodiment 257

The compound of embodiment 251, wherein the compound of is

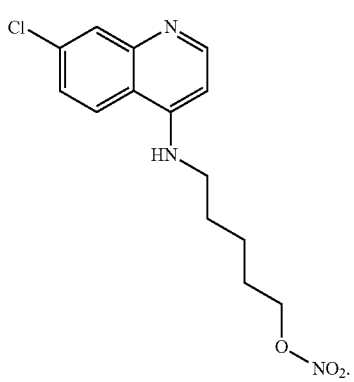 [SMILES: O=[N+]([O-])OCCCCCNc1ccnc2cc(Cl)ccc12]

Embodiment 258

The compound of embodiment 251, wherein the compound of is

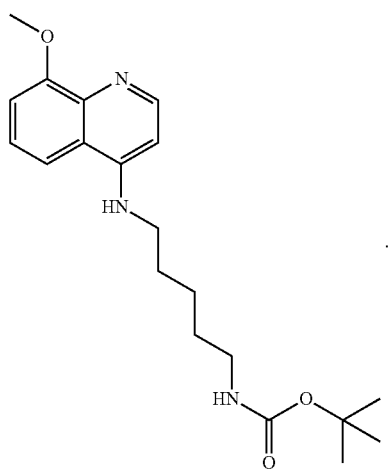 [SMILES: COc1cccc2c(NCCCCCNC(=O)OC(C)(C)C)ccnc12]

Embodiment 259

The compound of embodiment 251, wherein the compound of is

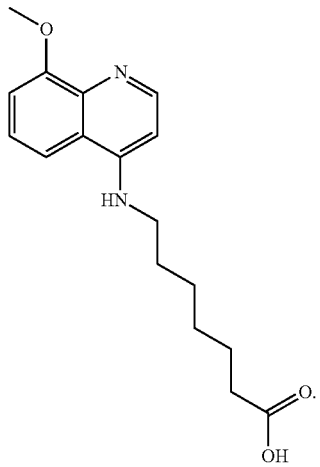

Embodiment 260

The compound of embodiment 251, wherein the compound of is

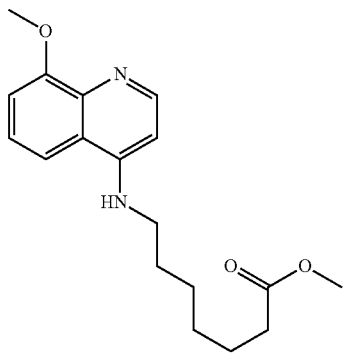

Embodiment 261

A compound having the Formula (V):

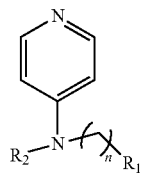
(V)

wherein:
n is 1-6;
$R_1$ nitrate; and
$R_2$ is a hydrogen or nitrogen dioxide.

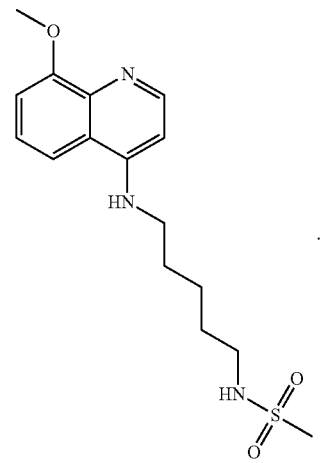 [SMILES: COc1cccc2c(NCCCCCNS(C)(=O)=O)ccnc12]

Embodiment 262

The compound of embodiment 261, wherein the compound of is selected from the group consisting of:

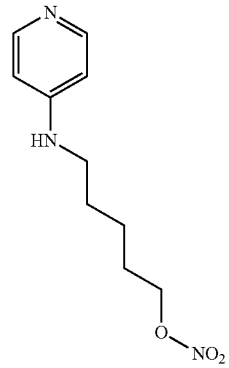 and 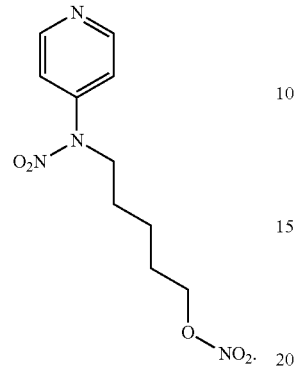

Embodiment 263

The compound of embodiment 262, wherein the compound of is

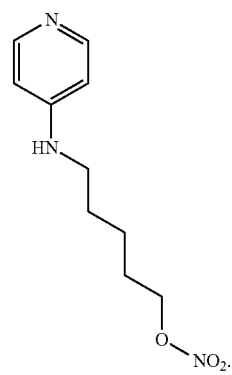 [SMILES: O=[N+]([O-])OCCCCCNc1ccncc1]

Embodiment 264

The compound of embodiment 262, wherein the compound of is

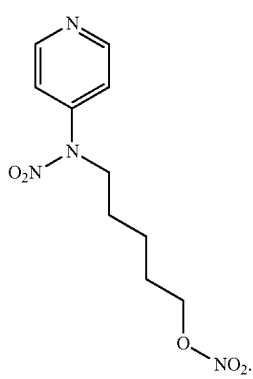 [SMILES: O=[N+]([O-])OCCCCCN(c1ccncc1)[N+](=O)[O-]]

Embodiment 265

A compound selected from Formula (VIII)

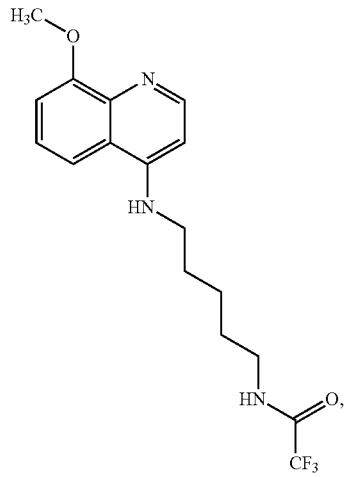

salts, optical isomers, geometric isomers, salts of isomers, and derivatives thereof.

Embodiment 266

The compound of Embodiment 265, wherein the compound is a salt of Formula (VIII).

Embodiment 267

The compound of Embodiment 265 or Embodiment 266, wherein the compound is Formula (VIII).

Embodiment 268

A composition comprising the compound of any of Embodiments 265-267.

Embodiment 269

The composition of Embodiment 268, wherein the amount of the compound is from about 0.0001% (by weight total composition) to about 99%.

Embodiment 270

The composition of Embodiment 268 or Embodiment 269, further comprising a formulary ingredient, an adjuvant, or a carrier.

Embodiment 271

A pharmaceutical composition comprising the compound of any of Embodiments 265-267.

Embodiment 272

The pharmaceutical composition of Embodiment 271, wherein the amount of the compound is from about 0.0001% (by weight total composition) to about 50%.

Embodiment 273

The pharmaceutical composition of Embodiment 271 or Embodiment 272, further comprising a formulary ingredient, an adjuvant, or a carrier.

Embodiment 274

A method for providing an animal with a compound comprising one or more administrations of one or more compositions comprising the compound of any of Embodiments 265-267, wherein the compositions may be the same or different if there is more than one administration.

Embodiment 275

The method of Embodiment 274, wherein at least one of the one or more compositions further comprises a formulary ingredient.

Embodiment 276

The method of Embodiment 274 or Embodiment 275, wherein at least one of the one or more compositions comprises the composition of any of Embodiments 268-270 or the pharmaceutical composition of any of Embodiments 271-273.

Embodiment 277

The method of any of Embodiments 274-276, wherein at least one of the one or more administrations comprises parenteral administration, mucosal administration, intravenous administration, subcutaneous administration, topical administration, intradermal administration, oral administration, sublingual administration, intranasal administration, or intramuscular administration.

Embodiment 278

The method of any of Embodiments 274-277, wherein if there is more than one administration at least one composition used for at least one administration is different from the composition of at least one other administration.

Embodiment 279

The method of any of Embodiments 274-278, wherein the compound of at least one of the one or more compositions is administered to the animal in an amount of from about 0.01 mg/kg animal body weight to about 150 mg/kg animal body weight.

Embodiment 280

The method of any of Embodiments 274-279, wherein the animal is a human, a rodent, or a primate.

Embodiment 281

A method for treating an animal for a disease, comprising one or more administrations of one or more compositions comprising the compound of any of Embodiments 265-267, wherein the compositions may be the same or different if there is more than one administration.

Embodiment 282

The method of Embodiment 281, wherein at least one of the one or more compositions further comprises a formulary ingredient.

Embodiment 283

The method of Embodiment 281 or Embodiment 282, wherein at least one of the one or more compositions comprises the composition of any of Embodiments 4-6 or the pharmaceutical composition of any of Embodiments 7-9.

Embodiment 284

The method of any of Embodiments 281-283, wherein at least one of the one or more administrations comprises parenteral administration, mucosal administration, intravenous administration, subcutaneous administration, topical administration, intradermal administration, oral administration, sublingual administration, intranasal administration, or intramuscular administration.

Embodiment 285

The method of any of Embodiments 281-284, wherein if there is more than one administration at least one composition used for at least one administration is different from the composition of at least one other administration.

Embodiment 286

The method of any of Embodiments 281-285, wherein the compound of at least one of the one or more compositions is administered to the animal in an amount of from about 0.005 mg/kg animal body weight to about 150 mg/kg animal body weight.

Embodiment 287

The method of any of Embodiments 281-286, wherein the animal is a human, a rodent, or a primate.

Embodiment 288

The method of any of Embodiments 281-287, wherein the animal is in need of the treatment.

Embodiment 289

The method of any of Embodiments 281-288, wherein the method is for treating cancer.

Embodiment 290

The method of any of Embodiments 281-289, wherein the method is for treating acute lymphoblastic leukemia, astrocytoma, basal cell carcinoma, bladder cancer, bone marrow cancer, brain cancer, brain tumors, childhood brain tumors, breast cancer, chronic lymphocytic leukemia (CLL), CNS cancer, glioblastoma, glioblastoma multiforme, gliosarcoma, astrocytoma, colon cancer, colorectal cancer, colon cancer, rectal cancer, endometrial cancer, gastric cancer, glioblastoma, glioblastoma multiforme, glioma, gliosarcoma, hepatocellular carcinoma, kidney cancer, renal cancer, leukemia, liver cancer, lung cancer, non-small cell lung cancer, lymphoma, melanoma, cutaneous malignant melanoma, melanoma tumorigenesis, malignancies, hematological malignancies, malignant nerve sheath tumors, medulloblastoma, meningioma, multiple myeloma, nasopharyngeal carcinoma, neuroblastoma, non-Hodgkin lymphoma, diffuse large B-cell lymphoma, non-small cell lung cancer, oral cancer, ovarian cancer, pancreatic cancer, pancreatic ductal adenocarcinoma, prostate cancer, rectal cancer, renal cancer, renal cell carcinoma, rhabdomyosarcoma, squamous cell carcinoma, head and neck squamous cell carcinoma, stomach cancer, thyroid cancer, uterine cancer, cancers that can result in metastasis, cancers resulting from metastasis, or cancerous tumors thereof.

Embodiment 291

The method of any of Embodiments 281-290, wherein the method is for treating breast cancer, childhood brain tumors, hematological malignancies, leukemia, melanoma, lung cancer, colon cancer, prostate cancer, or cancerous tumors thereof.

Embodiment 292

The method of any of Embodiments 281-291, wherein the method is for treating breast cancer, childhood brain tumors, hematological malignancies, leukemia, melanoma, lung cancer, colon cancer, or prostate cancer.

Embodiment 293

A method of inhibiting PFKFB4 in a cell, the method comprising contacting the cell with the compound of any of Embodiments 265-267.

Embodiment 294

The method of Embodiment 293 wherein PFKFB4 is specifically inhibited.

Embodiment 295

The method of Embodiment 293 or Embodiment 294, wherein the cell is a mammalian cell.

Embodiment 296

The method of any of Embodiments 293-295, wherein the cell is a cancer cell.

Embodiment 297

The method of any of Embodiments 293-296, wherein the cell is H460, H1299, H441, H522, DAOY, D283, SKBR3, Jurkat, B16F10, A549, MDA-MB-231, LNCaP, HCT116, or LLC cell line.

Embodiment 298

A method of inhibiting PFKFB4 in a subject, the method comprising administering to the subject an effective amount of the compound of any of Embodiments 265-267.

Embodiment 299

The method of Embodiment 298, wherein the compound is administered at a dosage effective for specifically inhibiting PFKFB4.

Embodiment 300

The method of Embodiment 298 or Embodiment 299, wherein the compound is administered orally or administered intravenously.

Embodiment 301

The method of any of Embodiments 298-300, wherein the subject has cancer.

Embodiment 302

The method of any of Embodiments 298-301, wherein the subject has breast cancer, childhood brain tumors, hematological malignancies, leukemia, melanoma, lung cancer, colon cancer, prostate cancer, or cancerous tumors thereof.

Embodiment 303

The method of any of Embodiments 298-302, wherein the method treats cancer in the subject.

Embodiment 304

The method of any of Embodiments 298-303, wherein the method treats breast cancer, childhood brain tumors, hematological malignancies, leukemia, melanoma, lung cancer, colon cancer, prostate cancer, or cancerous tumors thereof, in the subject.

Embodiment 305

The method of any of Embodiments 298-304, wherein the subject remains substantially free of signs of toxicity.

Embodiment 306

A method of reducing glycolytic flux in a cell, the method comprising contacting the cell with an effective amount of the compound of any of Embodiments 265-267.

Embodiment 307

The method of Embodiment 306, wherein the cell is a mammalian cell.

Embodiment 308

The method of Embodiment 306 or Embodiment 307, wherein the cell is a cancer cell.

Embodiment 309

The method of any of Embodiments 306-308, wherein the cell is H460, H1299, H441, H522, DAOY, D283, SKBR3, Jurkat, B16F10, A549, MDA-MB-231, LNCaP, HCT116, or LLC cell line.

Embodiment 310

A method of reducing proliferative capacity of a cell, the method comprising contacting the cell with an effective amount of the compound of any of Embodiments 265-267.

Embodiment 311

The method of Embodiment 310, wherein the cell is contacted with the compound at a dosage effective for specifically inhibiting PFKFB4.

Embodiment 312

The method of Embodiment 310 or Embodiment 311, wherein the cell is a mammalian cell.

Embodiment 313

The method of any of Embodiments 310-312, wherein the cell is a cancer cell.

Embodiment 314

The method of any of Embodiments 310-313, wherein the cell is H460, H1299, H441, H522, DAOY, D283, SKBR3, Jurkat, B16F10, A549, MDA-MB-231, LNCaP, HCT116, or LLC cell line.

Embodiment 315

A method of reducing fructose-2,6-bisphosphate (F2, 6BP) in a cell, the method comprising contacting the cell with an effective amount of the compound of any of Embodiments 265-267.

Embodiment 316

The method of Embodiment 315, wherein the cell is a mammalian cell.

Embodiment 317

The method of Embodiment 315 or Embodiment 316, wherein the cell is a cancer cell.

Embodiment 318

A method for preparing a compound of any of Embodiments 265-267, the method comprising,
(a) reacting a compound of Formula (VIII-p1) with a compound of Formula (VIII-p2) to result in a mixture comprising a compound of Formula (VIII-p3);
(b) reacting a compound of Formula (VIII-p3) with a compound of Formula (VIII-p4); and;
(c) recovering the compound of any of Embodiments 265-267,
wherein Formula (VIII-p1) is

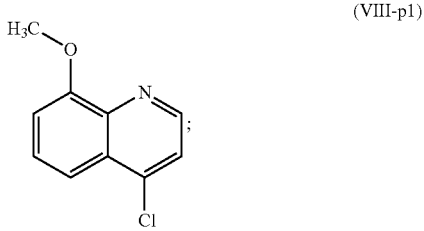

(VIII-p1)

Formula (VIII-p2) is

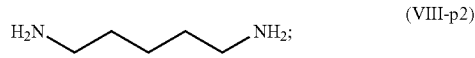

(VIII-p2)

Formula (VIII-p3) is

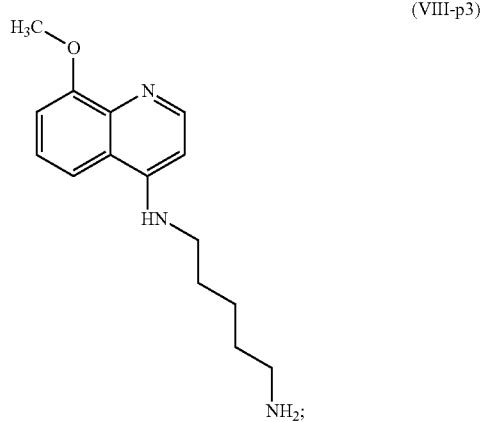 [SMILES: COc1cccc2c(NCCCCCN)ccnc12]

(VIII-p3)

and
Formula (VIII-p4) is

(VIII-p4)

Embodiment 319

The method of Embodiment 318, wherein the method is for preparing Formula (VIII).

All documents cited are incorporated herein by reference; the citation of any document is not to be construed as an admission that it is prior art with respect to the present invention.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising"

means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

The invention claimed is:

1. A compound selected from

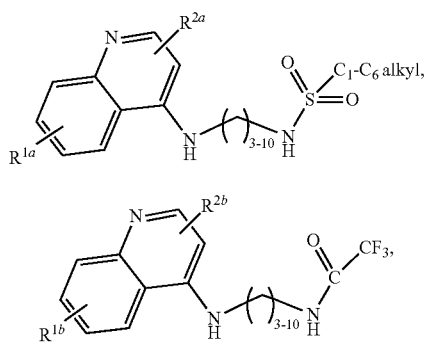

a salt of (IXa) or (IXb), an optical isomer of (IXa) or (IXb), a geometric isomer of (IXa) or (IXb), and a salt of an isomer of (IXa) or (IXb), wherein
  $R^{1a}$ is H or $C_1$-$C_7$ alkoxy;
  $R^{2a}$ is H or $C_3$-$C_8$ alkyl;
  $R^{1b}$ is H, $C_1$-$C_7$ alkoxy, or halogen; and
  $R^{2b}$ is H or $C_1$-$C_8$ alkyl.

2. The compound of claim 1, wherein the compound is selected from

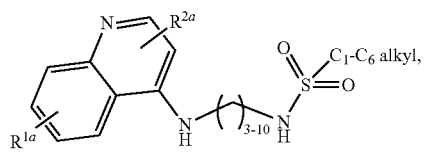

a salt of (IXa), an optical isomer of (IXa), a geometric isomer of (IXa), and a salt of an isomer of (IXa), wherein
  $R^{1a}$ is H or $C_1$-$C_7$ alkoxy; and
  $R^{2a}$ is H or $C_3$-$C_8$ alkyl.

3. The compound of claim 1, wherein the compound is selected from

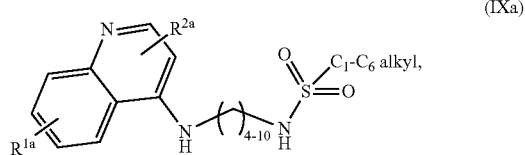

a salt of (IXa), an optical isomer of (IXa), a geometric isomer of (IXa), and a salt of an isomer of (IXa), wherein
  $R^{1a}$ is H or $C_1$-$C_7$ alkoxy; and
  $R^{2a}$ is H or $C_4$-$C_8$ alkyl.

4. The compound of claim 1, wherein the compound is selected from

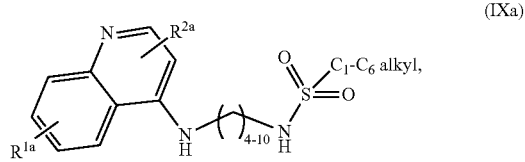

a salt of (IXa), an optical isomer of (IXa), a geometric isomer of (IXa), and a salt of an isomer of (IXa), wherein
  $R^{1a}$ is H or $C_1$-$C_7$ alkoxy; and
  $R^{2a}$ is H or $C_5$-$C_8$ alkyl.

5. The compound of claim 1, wherein the compound is selected from

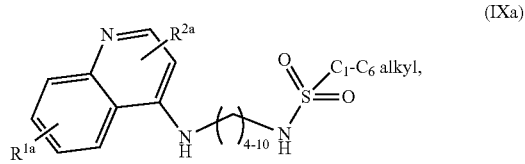

a salt of (IXa), an optical isomer of (IXa), a geometric isomer of (IXa), and a salt of an isomer of (IXa), wherein
  $R^{1a}$ is H or $C_1$-$C_7$ alkoxy; and
  $R^{2a}$ is H.

6. The compound of claim 1, wherein the compound is selected from

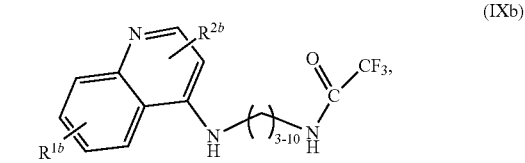

a salt of (IXb), an optical isomer of (IXb), a geometric isomer of (IXb), and a salt of an isomer of (IXb), wherein
  $R^{1b}$ is H, $C_1$-$C_7$ alkoxy, or halogen; and
  $R^{2b}$ is H or $C_1$-$C_8$ alkyl.

7. The compound of claim 1, wherein the compound is

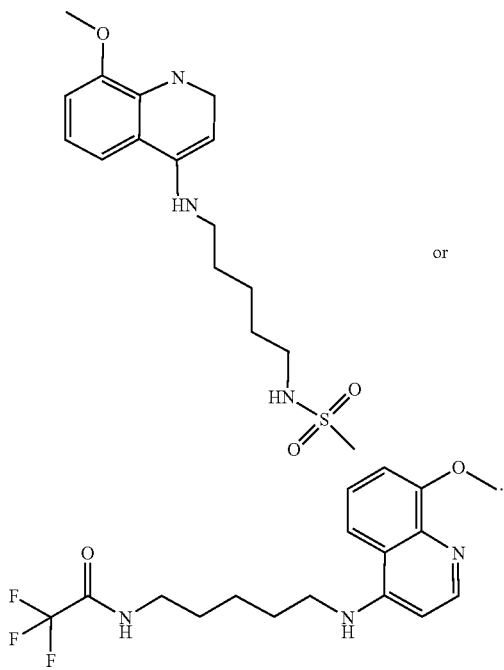

or

8. A composition comprising the compound of claim 1.

9. The composition of claim 8, wherein the amount of the compound is from about 0.0001% (by weight total composition) to about 99%.

10. The composition of claim 8, further comprising a formulary ingredient, an adjuvant, or a carrier.

11. A pharmaceutical composition comprising the compound of claim 1.

12. The pharmaceutical composition of claim 11, wherein the amount of the compound is from about 0.0001% (by weight total composition) to about 50%.

13. The pharmaceutical composition of claim 11, further comprising a formulary ingredient, an adjuvant, or a carrier.

14. A method of treating cancer in a subject in need of treatment thereof, the method comprising administering to the subject an effective amount of (a) a compound of claim 1, (b) a composition comprising a compound of (a), or (c) a pharmaceutical composition comprising a compound of (a); wherein the cancer is breast cancer, lung cancer, colon cancer, or prostate cancer.

15. The method of claim 14, wherein the administration is at a dosage effective for specifically inhibiting 6-phosphofructo-2-kinase/fructose-2,6-bisphophatase 4 (PFKFB4).

16. The method of claim 14, wherein the administration is administered orally or intravenously.

17. The method of claim 14, wherein the subject is substantially free of signs of toxicity.

18. The method of claim 14, wherein the subject is a mammal.

19. The method of claim 14, further comprising administering to the subject one or more additional therapeutic compounds.

20. The method of claim 19, wherein the one or more additional therapeutic compounds comprises one or more of a PFKFB3 inhibitor, a PFKFB2 inhibitor, or a PFKFB1 inhibitor.

21. A method of inhibiting PFKFB4 in a subject, the method comprising administering to the subject (a) a compound of claim 1, (b) a composition comprising a compound of (a), or (c) a pharmaceutical composition comprising a compound of (a).

22. The method of claim 21, wherein the administering is at a dosage effective for specifically inhibiting PFKFB4.

23. The method of claim 21, wherein the administering is orally or intravenously.

24. The method of claim 21, wherein the subject remains substantially free of signs of toxicity.

* * * * *